United States Patent
Shen et al.

(10) Patent No.: US 10,196,623 B2
(45) Date of Patent: *Feb. 5, 2019

(54) INTEIN-MODIFIED ENZYMES, THEIR PRODUCTION AND INDUSTRIAL APPLICATION

(71) Applicant: Agrivida, Inc., Medford, MA (US)

(72) Inventors: Binzhang Shen, Boston, MA (US); Gabor Lazar, Belmont, MA (US); Humberto de la Vega, Revere, MA (US); James Apgar, Newton, MA (US); Philip Lessard, Framingham, MA (US); R. Michael Raab, Arlington, MA (US)

(73) Assignee: AGRIVIDA, INC., Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/002,280

(22) Filed: Jan. 20, 2016

(65) Prior Publication Data

US 2016/0186157 A1 Jun. 30, 2016

Related U.S. Application Data

(60) Division of application No. 13/777,166, filed on Feb. 26, 2013, now Pat. No. 9,303,250, which is a continuation of application No. 12/590,444, filed on Nov. 6, 2009, now Pat. No. 8,420,387.

(51) Int. Cl.
| | |
|---|---|
| *C12N 9/24* | (2006.01) |
| *C12N 15/82* | (2006.01) |
| *C12N 9/42* | (2006.01) |

(52) U.S. Cl.
CPC .......... *C12N 9/2482* (2013.01); *C12N 9/248* (2013.01); *C12N 9/2437* (2013.01); *C12N 15/8216* (2013.01); *C12N 15/8241* (2013.01); *C12N 15/8246* (2013.01); *C12Y 302/01004* (2013.01); *C12Y 302/01008* (2013.01)

(58) Field of Classification Search
None
See application file for complete search history.

(56) References Cited

U.S. PATENT DOCUMENTS

| | | | |
|---|---|---|---|
| 5,496,714 A | 3/1996 | Comb et al. | |
| 5,654,184 A | 8/1997 | Curtiss et al. | |
| 5,780,708 A | 7/1998 | Lundquist et al. | |
| 5,834,247 A | 11/1998 | Comb et al. | |
| 5,981,835 A | 11/1999 | Austin-Phillips et al. | |
| 6,013,863 A | 1/2000 | Lundquist et al. | |
| 6,022,846 A | 2/2000 | Van Ooijen et al. | |
| 6,160,208 A | 12/2000 | Lundquist et al. | |
| 6,395,966 B1 | 5/2002 | Mumm et al. | |
| 6,531,316 B1 | 3/2003 | Lassner | |
| 6,800,792 B1 | 10/2004 | Howard et al. | |
| 6,858,775 B1 | 2/2005 | Xu et al. | |
| 7,102,057 B2 | 9/2006 | Lanahan et al. | |
| 7,550,263 B2 | 6/2009 | Meade et al. | |
| 7,709,697 B2 | 5/2010 | Raab | |
| 8,420,387 B2 | 4/2013 | Shen et al. | |
| 2002/0138878 A1 | 9/2002 | Sticklen et al. | |
| 2003/0131376 A1 | 7/2003 | Okubara et al. | |
| 2003/0159182 A1 | 8/2003 | Tackaberry et al. | |
| 2003/0167533 A1 | 9/2003 | Yadav et al. | |
| 2003/0233675 A1 | 12/2003 | Cao et al. | |
| 2004/0096938 A1 | 5/2004 | Xu et al. | |
| 2005/0125860 A1* | 6/2005 | Raab .................. | C12N 15/8216 800/298 |
| 2007/0192900 A1 | 8/2007 | Sticklen | |
| 2008/0115243 A1 | 5/2008 | Raab et al. | |
| 2009/0155238 A1 | 6/2009 | Weiner et al. | |
| 2011/0053195 A1 | 3/2011 | Bauer et al. | |

FOREIGN PATENT DOCUMENTS

| | | |
|---|---|---|
| EP | 0602899 A2 | 6/1994 |
| WO | 97/01642 A1 | 1/1997 |
| WO | 9736995 A1 | 10/1997 |
| WO | 98/021348 A1 | 5/1998 |
| WO | 00/36093 A2 | 6/2000 |
| WO | 00/52155 A2 | 9/2000 |
| WO | 00/071701 A1 | 11/2000 |
| WO | 01/059091 A2 | 8/2001 |
| WO | 03/050265 A2 | 6/2003 |
| WO | 03/056904 A2 | 6/2003 |

(Continued)

OTHER PUBLICATIONS

Morris et al 1998 Appl. Envrion. Microbiol. 64:1759-1765.*
Perler 2002 Nuc. Acids Res. 30:383-384.*
Tokuda et al 1999 Biochim. Biophys. Acta 1447:146-159, alignment provided.*
Zeidler et al., "Temperature-sensitive control of protein activity by conditionally splicing inteins," Nature Biotechnology, vol. 22, No. 7, Jul. 2004, 871-876.
Sijmons, P.C., et al., Production of Correctly Processed Human Serum Albumin in Transgenic Plants, Biotechnology, vol. 8, Mar. 1990, pp. 217-221.
Smeekens, et al., "Protein Transport into and Within Chloroplasts," Trends in Biochemical Sciences, vol. 15, Feb. 1990, pp. 73-76.
Smith et al., (1997B) Complete genome sequence of Methanobacterium thermoautotrophicum deltaH: functional analysis and comparative genomics. J Bacteriol 179(22): 7135-55. PubMed ID: 9371463.

(Continued)

*Primary Examiner* — Brent T Page
(74) *Attorney, Agent, or Firm* — Volpe and Koenig, P.C.

(57) ABSTRACT

A method of predicting an intein insertion site in a protein that will lead to a switching phenotype is provided. The method includes identifying a plurality of C/T/S sites within the protein; selecting from the plurality of C/T/S/sites those that are ranked 0.75 or higher by a support vector machine, within ten angstroms of the active site of the protein, and at or near a loop-β-sheet junction or a loop-α-helix junction. A method of controlling protein activity and hosts including proteins with controlled activity are also provided. Also, intein modified proteins and plants containing intein modified proteins are provided.

17 Claims, 48 Drawing Sheets
(8 of 48 Drawing Sheet(s) Filed in Color)
Specification includes a Sequence Listing.

(56) References Cited

FOREIGN PATENT DOCUMENTS

| WO | 2005096804 A2 | 10/2005 |
|---|---|---|
| WO | 07/146944 | 12/2007 |
| WO | 2007146944 A2 | 12/2007 |

OTHER PUBLICATIONS

Southworth et al., (1998) Control of protein splicing by intein fragment reassembly. Embo J 17(4): 918-26. PubMed ID: 9463370.

Southworth et al., (1999) Purification of proteins fused to either the amino or carboxy terminus of the Mycobacterium xenopi gyrase A intein. Biotechniques 27(1): 110-4, 116, 118-20. PubMed ID: 10407673.

Southworth et al., (2000) An alternative protein splicing mechanism for inteins lacking an N-terminal nucleophile. Embo J 19(18): 5019-26. PubMed ID: 10990465.

Sreenath, H.K., et al., "Production of Ethanol from Wood Hydrolyzate by Yeasts," Bioresource Technology, vol. 72, No. 3, 2000, pp. 253-260.

Staub, J.M., et al., "High-Yield Production of a Human Therapeutic Protein in Tobacco Chloroplasts," Nature Biotechnology, vol. 18, Mar. 2000, pp. 333-338.

Stoddard et al., (1998) Breaking up is hard to do. Nat Struct Biol 5(1): 3-5. PubMed ID: 9437416.

Sun et al., "Protein trans-Splicing to Produce Herbicide-Resistant Acetolactate Synthase," Applied and Environmental Microbiology, vol. 67, No. 3, pp. 1025-1029 (Mar. 2001).

Tague, B.W., et al., "A Short Domain of the Plant Vacuolar Protein Phytohemagglutinin Targets Invertase to the Yeast Vacuole," The Plant Cell, vol. 2, Jun. 1990, pp. 533-546.

Takagi et al., (1997) Characterization of DNA polymerase from *Pyrococcus* sp. strain KOD1 and its application to PCR. Appl Environ Microbiol 63(11): 4504-10. PubMed ID: 9361436.

Taylor, F., et al., "Dry-Grind Process for Fuel Ethanol by Continuous Fermentation and Stripping," Biotechnology Progress, vol. 16, 2000. pp. 541-547.

Telenti et al., (1997) The Mycobacterium xenopi GyrA protein splicing element: characterization of a minimal intein. J Bacteriol 179(20): 6378-82. PubMed ID: 9335286.

Tingey, S.V., et al., "Glutamine Synthetase Genes of Pea Encode Distinct Polypeptides Which are Differentially Expressed in Leaves, Roots and Nodules," The EMBO Journal, vol. 6, No. 1, 1987, pp. 1-9.

Ulgen, K.O., et. al., "Bioconversion of Starch Into Ethanol by a Recombinant *Saccharomyces cerevisiae* Strain YPG-AB," Process Biochemistry, vol. 37, 2002, pp. 1157-1168.

UNIPROT, P77853_DICTH, pp. 1-4 (Feb. 1, 1997).

Van Den Broeck, G., et al., Targeting of a Foreign Protein to Chloroplasts by Fusions to the Transmit Peptide from the Small Subunit of Ribulose 1,5-Bisphosphate Carboxylase, Nature, vol. 313, Ksmistu 1985, pp. 358-363.

Von Heijne, G., "Towards a Comparative Anatomy of N-Terminal Topogenic Protein Sequences," Journal of Molecular Biology, vol. 189, 1986, pp. 239-242.

Wallace, "The Curious Case of Protein Splicing: Mechanistic Insights Suggested by Protein Semisynthesis," Protein Science, vol. 2, pp. 697-705 (1993).

Wang et al., "Identification of an Unusual Intein in Chloroplast ClpP Protease of Chlamydomonas Eugametos" May 2, 1997, Journal of Biological Chemistry, vol. 272, No. 18, pp. 11869-11873.

Wenzler, H.C., et al., "Analysis of a Chimeric Class-I Patatin-GUS Gene in Transgenic Potato Plants: High-Level Expression in Tubers and Sucrose-Inducible Expressions in Cultured Leaf and Stem Explants," Plant Molecular Biology, vol. 12, 1989, pp. 41-50.

Wood, D. W., et al., "Optimized Single-Step Affinity Purification with a Self-Cleaving Intein Applied to Human Acidic Fibroblast Growth Factor," Biotechnology Progress, vol. 16, 2000, pp. 1055-1063.

Xie et al., Accession No. Q2P9Q1 (2006).

Xie et al., Accession No. AM181054 (2006).

Xu, M., et al., "In Vitro Protein Splicing of Purified Precursor and the Identification of Branched Intermediate," Cell, vol. 75, Dec. 31, 1993, pp. 1371-1377.

Xu et al., (1994) Protein splicing: an analysis of the branched intermediate and its resolution by succinimide formation. Embo J 13(23): 5517-22. PubMed ID: 7988548.

Xu, M., et al., "The Mechanism of Protein Splicing in its Modulation by Mutation," The EMBO Journal, vol. 15, No. 19, 1996, pp. 5146-5153.

Yamazaki et al., (1998) Segmental isotope labeling for protein NMR using peptide splicing. J. Am. Chem. Soc. 120: 5591-5592.

Yang, et al., "Intein-mediated assembly of a functional .beta.-glucuronidase in transgenic plants," PNAS, vol. 100, No. 6, pp. 3513-3518 (2003).

Ziegler M.T. et al., "Accumulation of Thermostable Endo-1,4-.beta.-D-Glucanase in the Apoplast of *Arabidposis thaliana* Leaves," Molecular Breeding, vol. 6, 2000, pp. 37-46.

Altintas, M. M., et al, "Improvement of Ethanol Production from Starch by Recombinant Yeast Through Manipulation of Environmental Factors," Enzyme and Microbial Technology, vol. 31, No. 5, 2002, pp. 640-647.

Aspegren, K., et al., "Secretion of Heat-Stable Fungal .beta.-Glucanase from Transgenic, Suspension-Cultured Barley Cells," Molecular Breeding, 1995, pp. 91-99.

Birch, R.G., Plant Transformation: Problems and Strategies for Practical Application, Annual Review of Plant Physiology and Plant Molecular Biology, vol. 48, Jun. 1997, pp. 297-326.

Bird, C.R., et al., The Tomato Polygalacturonase Gene and Ripening-Specific Expressions in Transgenic Plants, Plant Molecular Biology, 1988, pp. 651-662.

Brederode, F.T., et al., Complete Nucleotide Sequence of Alfalfa Mosaic Virus RNA 4, Nucleic Acids Research, vol. 8, No. 10, 1980, pp. 2213-2223.

Broothaerts, W., et al., "Gene Transfer to Plants by Diverse Species of Bacteria," Nature, vol. 433, Feb. 2005, pp. 629-633/.

Bult et al., (1996) Complete genome sequence of the methanogenic archaeon, Methanococcus jannaschii. Science 273(5278): 1058-73. PubMed ID: 8688087.

Cambon-Bonavita et al., (2000) Cloning, expression, and characterization of DNA polymerase I from the hyperthermophilic archaea Thermococcus fumicolans. Extremophiles 4(4): 215-25. PubMed ID: 10972190.

Cameron, D.C., et al., "Metabolic Engineering of Propanediol Pathways," Biotechnology Progress, 1998, pp. 116-125.

Chen et al., "Herbicide Resistance from a Divided EPSPS Protein: The Split Synechocystis DnaE Intein as an In Vivo Affinity Domain", Gene: An International Journal of Genes and Genomes, vol. 263, pp. 39-48 (2001).

Chen et al., (2000) Protein splicing in the absence of an intein penultimate histidine. J Biol Chem 275(27): 20431-5. PubMed ID: 10770923.

Cheon, B.Y., et al., "Ovexpression of Human Erythropoietin (EPO) Affects Plant Morphologies: Retarded Vegetative Growth in Tobacco and Male Sterility in Tobacco and *Arabidopsis*," Transgenic Research, 2004, pp. 541-549.

Chih-Ching, C., et al., "Establishment of an Efficient Medium for Anther Culture of Rice Through Comparative Experiments on the Nitrogen Sources," Scientia Sinica, vol. 18, No. 3, 1975, pp. 659-668.

Chin et al., Protein trans-splicing in transgenic plant chloroplast: Reconstruction of herbicide resistance from split genes, PNAS, vol. 100, No. 8, pp. 4510-4515 (2003).

Chong et al., "Modulation of Protein Splicing of the *Saccharomyces cerevisiae* Vacuolar Membrane ATPase Intein," The Journal of Biological Chemistry, vol. 273, No. 17, pp. 10567-10577. (Apr. 24, 1998).

Chong, et al. ., "Single-column purification of free recombinant proteins using a self-cleavable affinity tag derived from a protein splicing element", Gene: An International Journal of Genes Genomes, vol. 192, pp. 271-281 (1997).

Chute et al., (1998) A topA intein in Pyrococcus furiosus and its relatedness to the r-gyr intein of Methanococcus iannaschii. Gene 210(1): 85-92. PubMed ID: 9524230.

(56) References Cited

OTHER PUBLICATIONS

Clarke, Neil D., "A Proposed Mechanism for the Self-Splicing of Proteins," Proceedings of the National Academy of Science, USA, vol. 91, pp. 11084-11088, Nov. 1994.
Coruzzi G. et al., "Tissue-Specific and Light-Regulated Expression of Pea Nuclear Gene Coding the Small Subunit of Ribulose-1, 5-Bisphosphate Carboxylase," The EMBO Journal, 1984, 1671-1679.
Dai, Z., et al., "Expression of Acidothermus Cellulolyticus Endoglucanase E1 in Transgenic Tobacco: Biochemical Characteristics and Physiological Effects," Transgenic Research, 2000, pp. 43-54.
Dai, Z. et al., "Improved Plant-Based Production of E1 Endoglucanase Using Potato: Expression Optimization and Tissue Targeting," Molecular Breeding, 2000, pp. 277-285.
Dale, Bruce E., "Biobased Industrial Products: Bioprocess Engineering When Costs Really Count," Biotechnology Progress, 1999, pp. 775-776.
Dalgaard et al., (1997) Statistical modeling, phylogenetic analysis and structure prediction of a protein splicing domain common to inteins and hedgehog proteins. J Comput Biol 4(2): 193-214. PubMed ID: 9228618.
Davis, E., et al., "Novel Structure of the recA Locus of Mycobacterium Tuberculosis Implies Processing of the Gene Product," Journal of Bacteriology, vol. 173, No. 18, Sep. 1991, pp. 5653-5662.
Davis, E., et al., "Protein Splicing in the Maturation of M. Tuberculosis RecA Protein: A Mechanism for Tolerating a Novel Class of Intervening Sequence," Cell Press, vol. 71, Oct. 16, 1992, pp. 201-210.
Davis et al., "Protein Splicing: The Lengths Some Proteins Will Go To" 1995, Antonie van Leeuwenhoek, vol. 67, pp. 131-137.
Deckert et al., (1998) The complete genome of the hyperthermophilic bacterium *Aquifex aeolicus*. Nature. 392(6674): 353-8. PubMed ID: 9537320.
Derbyshire, et al., "Lightning Strikes Twice: Intron-Intein Coincidence," Proceedings of the National Academy of Science, USA, vol. 95, pp. 1356-1357, Feb. 17, 1998.
Evans, et al., "Semisynthesis of Cytotoxic Proteins Using a Modified Protein Splicing Element," Protein Science, vol. 7: pp. 2256-2264 (1998).
Evans et al., (1999) The in vitro ligation of bacterially expressed proteins using an intein from Methanobacterium thermoautotrophicum. J Biol Chem 274(7): 3923-6. PubMed ID: 9933578.
Gangopadhyay, J.P., et. al., "In Vitro Splicing of Erythropoietin by the Mycobacterium Tuberculosis RecA Intein Without Substituting Amino Acids at the Splice Junctions," Biochimica et Biophysica Acta, vol. 1619, (2003), pp. 193-200.
Genschik et al., (1997) The human RNA 3'-terminal phosphate cyclase is a member of a new family of proteins conserved in Eucarya, Bacteria and Archaea. Embo J. 16(10): 2955-67. PubMed ID: 9184239.
Genschik et al., (1998) Characterization of the *Escherichia coli* RNA 3'-terminal phosphate cyclase and its sigma54-regulated operon. J Biol Chem. 273(39): 25516-26. PubMed ID: 9738023.
Gimble, "Invasion of a Multitude of Genetic Niches by Mobile Endonuclease Genes" Feb. 8, 2000, FEMS Microbiology Letters, vol. 185, pp. 99-107.
Gordon-Kamm, et al., "Transformation of Maize Cells and Regeneration of Fertile Transgenic Plants," The Plant Cell, vol. 2, pp. 603-618, Jul. 1990.
Guilley, H., et al., "Transcription of Cauliflower Mosaic Virus DNA: Detection of Promoter Sequences, and Characterization of Transcripts," Cell, vol. 30, Oct. 1982, pp. 763-773.
Gupta, P.K., et al., "Shoot Multiplication from Mature Trees of Douglas Fir and Sugar Pine," Plant Cell Reports, vol. 4, 1985, pp. 177-179.
Hashimoto et al., (2000) Crystallographic study of intein homing endonuclease II encoded in the archaeal DNA polymerase gene. Acta Crystallogr D Biol Crystallogr 56 ((Pt 9)): 1185-6. PubMed ID: 10957641.

Hashimoto et al., (2001) Crystal structure of DNA polymerase from hyperthermophilic archaeon Pyrococcus kodakaraensis KOD1. J Mol Biol 306(3): 469-77. PubMed ID: 11178906.
Higgins, T.J.V., Synthesis and Regulation of Major Proteins in Seeds, Annual Review of Plant Physiology, 1984, pp. 191-221.
Hirata, R., et al., "Molecular Structure of a Gene, VMA1, Encoding the Catalytic Subunit of Fl.sup.+-Translocating Adenosine Triphosphatase fro Vacuolar Membranes of *Saccharomyces cerevisiae*," The Journal of Biological Chemistry, vol. 265, No. 12, Apr. 25, 1990, pp. 6826-6733.
Hodges et al., (1992) Protein splicing removes intervening sequences in an archaea DNA polymerase. Nucleic Acids Res 20(23): 6153-7. PubMed ID: 1475179.
Hood, E.E., et al., "Commercial Production of Avidin from Transgenic Maize: Characterization of Transformant, Production, Processing, Extraction and Purification," Molecular Breeding, 1997, pp. 291-306.
Horsch, R.B., et al, "A Simple and General Method for Transferring Genes into Plants," Science, Mar. 1985, pp. 1229-1231.
Ichiyanagi et al., (2000) Crystal structure of an archaeal intein-encoded homing endonuclease PI-PfuI. J Mol Biol 300 (4): 889-901. PubMed ID: 10891276.
Ingram, L.O., et al., "Enteric Bacterial Catalysts for Fuel Ethanol Production," Biotechnology Progress, 1999, pp. 856-866.
Kane, P.M., et. al., "Protein Splicing Converts the Yeast TFP1 Gene Product to the 69-kD Subunit of the Vacuolar H+-Adenosine Triphosphatase," Science, New Series, vol. 250, No. 4981, Nov. 2, 1990, pp. 651-657.
Kawarabayasi et al., (1998) Complete sequence and gene organization of the genome of a hyper-thermophilic archaebacterium, *Pyrococcus horikoshii* OT3. DNA Res 5(2): 55-76. PubMed ID: 9679194.
Kawarabayasi et al., (1998B) Complete sequence and gene organization of the genome of a hyper-thermophilic archaebacterium, *Pyrococcus horikoshii* OT3 (supplement). DNA Res. 5(2): 147-55. PubMed ID: 9679203.
Kawarabayasi et al., (1999) Complete genome sequence of an aerobic hyper-thermophilic crenarchaeon, Aeropyrum pernix K1. DNA Res. 6(2): 83-101, 145-52. PubMed ID: 10382966.
Kawarabayasi, Y. (2001) Genome of Pyrococcus horikoshii OT3. Methods Enzymol. 330: 124-34. PubMed ID: 11210494.
Kawashima et al., (1999) Determination of the complete genomic DNA sequence of Thermoplasma volvanium GSS1. Proc. Jpn. Acad 75: 213-218.
Klabunde et al., (1998) Crystal structure of GyrA intein from Mycobacterium xenopi reveals structural basis of protein splicing. Nat Struct Biol 5(1): 31-6. PubMed ID: 9437427.
Klein, T.M., et al., "High-Velocity Microprojectiles for Delivering Nucleic Acids Into Living Cells," Nature, vol. 327, May 1987, pp. 70-73.
Komori et al., (1999) PI-PfuI and PI-PfuII, intein-coded homing endonucleases from Pyrococcus furiosus. I. Purification and identification of the homing-type endonuclease activities. Nucleic Acids Res 27(21): 4167-74. PubMed ID: 10518607.
Komori et al., (1999B) PI-PfuI and PI-PfuII, intein-coded homing endonucleases from Pyrococcus furiosus. II. Characterization of the binding and cleavage abilities by site-directed mutagenesis. Nucleic Acids Res 27(21): 4175-82. PubMed ID: 10518608.
Lai et al., "Structural Characterization of Human Erythropoietin." The Journal of Biological Chemistry, vol. 261, pp. 3116-3121, Mar. 5, 1986.
Latif, F., et al., "Production of Ethanol and Xylitol from Corn Cobs by Yeasts," Bioresource Technology, vol. 77, 2001, pp. 57-63.
Lecompte et al., (2001) Genome evolution at the genus level: comparison of three complete genomes of hyperthermophilic archaea. Genome Res. 11(6): 981-93.. PubMed ID: 11381026.
Liu et al., (1997) A DnaB intein in Rhodothermus marinus: indication of recent intein homing across remotely related organisms. Proc Natl Acad Sci U S A 94(15): 7851-6. PubMed ID: 9223276.
Lynd, L.R., et al., "Biocommodity Engineering," Biotechnology Progress, vol. 15, 1999, pp. 777-791.

(56) References Cited

OTHER PUBLICATIONS

Maeder et al., (1999) Divergence of the hyperthermophilic archaea Pyrococcus furiosus and P. horikoshii inferred from complete genomic sequences. Genetics 152(4): 1299-305. PubMed ID: 10430560.

Mansfield, S.D., et al., "Substrate and Enzyme Characteristics that Limit Cellulose Hydrolysis," Biotechnology Progress, vol. 15, 1999, pp. 804-816.

Matsumoto, S., et al., "Characterization of Human Glycoprotein (Erythropoietin) Produced in Cultured Tobacco Cells," Plant Molecular Biology, 1995, pp. 1163-1172.

Montvalvo-Rodriguez, R., et al., "Autohydrolysis of Plant Polysaccharides Using Transgenic Hyperthermophilic Enzymes," Biotechnology and Bioengineering, vol. 2, 2000, pp. 151-159.

Morassutti et al., "Production of a Recombinant Antimicrobial Peptide in Transgenic Plants Using a Modified VMA Intein Expression System," FEBS Letters, vol. 519, Nos. 1-3, pp. 141-146 (Apr. 2002).

Morris et al., "Cloning of the xynB Gene from Dictyoglomus thermophilum Rt46B1 and Action of the Gene Product on Kraft Pulp," Applied and Environmental Microbiology, vol. 64, No. 5, pp. 1759-1765 (May 1998).

Murashige, T., et al., "A Revised Medium for Rapid Growth and Bio Assays with Tobacco Tissue Cultures," Physiologia Plantarum, vol. 15, pp. 473-497 (1962).

Ng et al., (2000) Genome sequence of *Halobacterium* species NRC-1. Proc Natl Acad Sci U S A. 97(22): 12176-81. PubMed ID: 11016950.

Niehaus et al., (1997) Cloning and characterisation of a thermostable alpha-DNA polymerase from the hyperthermophilic archaeon *Thermococcus* sp. TY. Gene 204(1-2): 153-8. PubMed ID: 9434178.

Nishioka et al., (1998) Characterization of two intein homing endonucleases encoded in the DNA polymerase gene of Pyrococcus kodakaraensis strain KOD1. Nucleic Acids Res 26(19): 4409-12. PubMed ID: 9742242.

Office Action from Ukrainian Application No. a 2012 06712, with English translation, dated Nov. 10, 2014, 11 pages.

Office Action from U.S. Appl. No. 13/508,234 dated Jan. 5, 2015, 29 pages.

Office Action from U.S. Appl. No. 13/508,156 dated Jan. 13, 2015, 31 pages.

Olsson, L., et al., "Fermentation of lignocellulosic Hydrolysates for Ethanol Production," Enzyme and Microbial Technology, vol. 18, 1996, pp. 312-331.

Otomo et al., (1999) Improved segmental isotope labeling of proteins and application to a larger protein. J Biomol NMR 14(2): 105-14. PubMed ID: 10427740.

Otomo et al., (1999B) NMR observation of selected segments in a larger protein: central-segment isotope labeling through intein-mediated ligation. Biochemistry 38(49): 16040-4. PubMed ID: 10587426.

Parsons, T.J., et al., "Transformation of Poplar by Agrobacterium Tumefaciens," Biotechnology, vol. 4, Jun. 1986, pp. 533-536.

Perler, et al. (1997) Compilation and analysis of intein sequences. Nucleic Acids Res 25(6): 1087-93. PubMed ID: 3092614.

Perler, "InBase: the Intein Database" Aug. 31, 2001, Nucleic Acids Research, vol. 30, No. 1. pp. 383-384.

Perler et al., (1992) Intervening sequences in an Archaea DNA polymerase gene. Proc Natl Acad Sci U S A. 89(12): 5577-81. PubMed ID: 1608969.

Perler, F.B., et al., "Protein Splicing Elements; Inteins and Exteins—A Definition of Terms and Recommended Nomenclature", Nucleic Acids Research, vol. 22, No. 7, Feb. 24, 1993, pp. 1125-1127.

Pietrokovski, "Conserved Sequence Features of Inteins (Protein Introns) and Their Use in Identifying New Inteins and Related Proteins" Aug. 10, 1994, Protein Science, vol. 3, pp. 2340-2350.

Pietrokovski, S. (1998) Modular organization of inteins and C-terminal autocatalytic domains. Protein Sci 7(1): 64-71. PubMed ID: 9514260.

Poirier, Yves, "Green Chemistry Yields a Better Plastic," Nature Biotechnology, vol. 17, Oct. 1999, pp. 960-961.

Riera et al., (1997) Ribonucleotide reductase in the archaeon Pyrococcus furiosus: a critical enzyme in the evolution of DNA genomes?. Proc Natl Acad Sci U S A 94(2): 475-8. PubMed ID: 9012808.

Rocha-Sosa, M., et al., "Both Developmental and Metabolic Signals Activate the Promoter of a Class I Patatin Gene," The EMBO Journal, vol. 8, No. 1, 1989, pp. 23-29.

Ruepp et al., (2000) The genome sequence of the thermoacidophilic scavenger Thermoplasma acidophilum. Nature. 407(6803): 508-13. PubMed ID: 11029001.

Ryan, Al., et al., Genomic Sequence of a 12S Seed Storage Protein from Oilseed Rape, Nucleic Acids Research, vol. 17, No. 9, 1989, p. 3584.

Sakon et al., Accession No. Gun1_ACIC1 (1996).

Saves et al., (2000) Inteins of Thermococcus fumicolans DNA polymerase are endonucleases with distinct enzymatic behaviors. J Biol Chem 275(4): 2335-41. PubMed ID: 10644683.

Saves et al., (2000C) The Thy pol-2 intein of Thermococcus hydrothermalis is an isoschizomer of PI-Tlil and PI-Tfull endonucleases. Nucleic Acids Res 28(21): 4391-6. PubMed ID: 11058140.

Schreier, P.H., et al., ,,The Use of Nuclear-Encoded Sequences to Direct the Light-Regulated Synthesis and Transport of a Foreign Protein into Plant Chloroplasts, The EMBO Journal, vol. 4, No. 1, 1985, pp. 25-32.

Senejani et al., (2001) The intein of the Thermoplasma A-ATPase A subunit: structure, evolution and expression in *E. coli*. BMC Biochem 2: 13. PubMed ID: 11722801.

Shao et al., (1995) Protein splicing: characterization of the aminosuccinimide residue at the carboxyl terminus of the excised intervening sequence. Biochemistry 34(34): 10844-50. PubMed ID: 7662664.

Shao et al., (1996) Protein splicing: evidence for an N—O acyl rearrangement as the initial step in the splicing process. Biochemistry 35(12): 3810-5. PubMed ID: 8620003.

Shen et al., (2001) Invariant Asp-1122 and Asp-1124 are essential residues for polymerization catalysis of family D DNA polymerase from Pyrococcus horikoshii. J Biol Chem 276(29): 27376-83. PubMed ID: 11319225.

Shimamoto, K., et al., Fertile Transgenic Rice Plants Regenerated from Transformed Protoplasts, Nature, vol. 338, Mar. 1989, pp. 274-276.

Shingledecker et al., "Reactivity of the Cysteine Residues in the Protein Splicing Active Center of the Mycobacterium Tuberculosis RecA intein" Mar. 1, 2000, Archives of biochemistry and biophysics, vol. 375, No. 1, pp. 138-144.

Jensen, L.G. et al. "Transgenic Barley Expressing a Protein-Engineered, Thermostable (1,3-1,4)-β-Glucanase During Germination" (1996) Proc. Natl. Acad. Sci. 93: 3487-3491.

Herber, K. et al. "Apoplastic Expression of the Xylanase and β(1-3,1-4) Glucanase Domains of the xyn D Gene from Ruminococcus flavefaciens Leads to Functional Polypeptides in Transgenic Tobacco Plants" (1996) Molecular Breeding 2: 81-87.

\* cited by examiner

INTEIN-MODIFIED ENZYMES, THEIR PRODUCTION AND INDUSTRIAL APPLICATION

REFERENCE TO RELATED APPLICATIONS

This application is a divisional of U.S. application Ser. No. 13/777,166, filed Feb. 26, 2013, which was a continuation of U.S. application Ser. No. 12/590,444, filed Nov. 6, 2009, and issued on Apr. 16, 2013 as U.S. Pat. No. 8,420,387, all of which are incorporated herein by reference as if fully set forth.

The sequence listing titled "Sequence Listing," which was filed as part of this application, was created on Jan. 20, 2016, and had a file size of 7,439,923 bytes is incorporated herein by reference as if fully set forth.

The substitute sequence listing titled "Substitute Sequence Listing" filed Mar. 14, 2016 having a file size of 7,438,993 bytes, and created on Mar. 14, 2013, is incorporated herein by reference as if fully set forth.

The substitute sequence listing titled "Substitute Sequence Listing" filed Mar. 14, 2016 having a file size of 7,438,993 bytes, and created on Mar. 214, 2013, is incorporated herein by reference as if fully set forth.

FIELD OF INVENTION

The invention relates to controlling the activity of proteins.

BACKGROUND

Many proteins have useful characteristics but in certain settings a protein can be difficult to use. For example, hydrolytic enzymes have important industrial and agricultural applications, but their expression and production may be associated with undesirable phenotypic effects in some expression hosts. For example, cell wall degrading enzymes, which include cellulases, xylanases, ligninases, esterases, peroxidases, and other hydrolytic enzymes, are often associated with detrimental effects on growth, physiological, and agronomic performance when expressed in plants. Xylanases are enzymes that catalyze the hydrolysis of beta-1,4-xylan, a linear polysaccharide component of hemicellulose contained in plant cell walls Cellulases are enzymes that catalyze either the internal or terminal hydrolysis of glucose polymers linked by beta-1,4-D-glycosidic bonds contained in cellulose, cellulose strains with different degrees of polymerization, and cellobiose. Based on these activities, expression of a xylanase or a cellulase in a plant may lead to undesirable degradation of plant components. Some enzymes may also be poorly expressed in microbial hosts, due to their hydrolytic activity.

SUMMARY

In an aspect, the invention relates to an intein modified protein. The intein modified protein includes a target protein and an intein inserted into the target protein at a site i) immediately prior to a cysteine, threonine, or serine residue of the target protein, ii) within ten angstroms from an active site of the target protein, and iii) within 10 amino acids of a loop-β-sheet junction or within 10 amino acids of a loop-α-helix junction of the target protein. The target protein is a xylanase or a cellulase.

In another aspect, the invention relates to an intein modified protein having at least 90% identity to an amino acid sequence selected from the group consisting of SEQ ID NOS: 1692-1695, 1698, 1719, 1732, 1739-1742, 1745-1750, 1753-1766, 1768-1769, 1772-1773.

In another aspect, the invention relates to a transgenic plant including an expression construct encoding an intein modified protein. The intein modified protein encoded by the expression construct includes a target protein and an intein inserted into the target protein at a site i) immediately prior to a cysteine, threonine, or serine residue of the target protein, ii) within ten angstroms from an active site of the target protein, and iii) within 10 amino acids of a loop-α-sheet junction or within 10 amino acids of a loop-β-helix junction of the target protein. The target protein is a xylanase or a cellulase.

In another aspect, the invention relates to a transgenic plant including an expression construct encoding an intein modified protein having at least 90% identity to an amino acid sequence selected from the group consisting of SEQ ID NOS: 1692-1695, 1698, 1719, 1732, 1739-1742, 1745-1750, 1753-1766, 1768-1769, 1772-1773.

In another aspect, the invention relates to a method of making an intein modified protein. The method includes (a) identifying a plurality of cysteine, serine or threonine sites within the protein, whether native or introduced, and (b) carrying out at least one of steps (i) to (iv): (i) analyzing the local sequence of each of the plurality of cysteine, serine or threonine sites with a support vector machine; (ii) identifying an active site of the protein, wherein a respective distance separates the active site and each of the plurality of cysteine, serine or threonine sites, and identifying the respective distance between the active site and each of the plurality of cysteine, serine or threonine sites; and (iii) identifying a secondary structure of the protein at each of the plurality of cysteine, serine or threonine sites. The method also includes (c) inserting an intein into the protein at a site immediately before at least one of the cysteine, serine or threonine sites that is in a position selected from at least one of the group consisting of i) one of the plurality of cysteine, serine or threonine sites ranked 0.75 or higher by the support vector machine, ii) one of the plurality of cysteine, serine or threonine sites within ten angstroms of the active site and iii) one of the plurality of cysteine, serine or threonine sites within ten amino acids from a loop-β-sheet junction or one of the plurality of cysteine, serine or threonine sites within ten amino acids from a loop-α-helix junction.

In another aspect, the invention relates to an expression construct comprising a nucleic acid having a sequence with at least 90% identity to the sequence of SEQ ID NO: 1.

In another aspect, the invention relates to a mutant intein comprising an amino acid sequence having 90% identity to a sequence selected from the group consisting of SEQ ID NOS: 92-103, 1675, 1678-1681, 1689, 1691, 1700-1708, and 1710.

BRIEF DESCRIPTION OF THE DRAWINGS

The patent or application file contains at least one color drawing or photograph as a drawing executed in color. Copies of this patent or patent application publication with color drawing(s) will be provided by the Office upon request and payment of the necessary fee.

The following detailed description of the preferred embodiments will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIG. 3A illustrates a western blot showing the P77853-Tth-S158-2 protein (SEQ ID No. 1672) in that was preheat treated at 37° C. (panel 2, left lane) or 55° C. (panel 2, right lane) for four hours. Also shown are lanes containing protein from the empty vector control (VCT) and wild-type P77853 protein (P77) that was preheat treated in the same manner.

FIG. 3B illustrates a western blot showing the P77853-Tth-S158-4 protein (SEQ ID No. 1673) that was preheat treated at 37° C. (panel 4, left lane) or 55° C. (panel 4, right lane) for four hours. Also shown are lanes containing protein from the empty vector control (VCT) and wild-type P77853 protein (P77) that was preheat treated in the same manner.

FIG. 3C illustrates a western blot showing the P77853-Tth-S158-7 protein (SEQ ID No. 1674) that was preheat treated at 37° C. (panel 7, left lane) and 55° C. (panel 7, middle lane) for four hours, and 70° C. for one hour (panel 7, right lane). Also shown are lanes containing protein from the empty vector control (VCT) and wild-type P77853 protein (P77).

FIG. 3D illustrates a western blot showing the P77853-Tth-S158-19 protein (SEQ ID No. 1675) that was preheat treated at 37° C. (panel 19, left lane) or 55° C. (panel 19, middle lane) for four hours, and 70° C. for one hour (panel 19, left lane). Also shown are lanes containing protein from the empty vector control (VCT) and wild-type P77853 protein (P77).

FIG. 3E illustrates a western blot showing the P77853-Tth-S158-20 protein (SEQ ID No. 1676) that was preheat treated at 37° C. (panel 20, left lane) or 55° C. (panel 20, middle lane) for four hours, and 70° C. for one hour (panel 20, right lane). Also shown are lanes containing protein from the empty vector control (VCT) and wild-type P77853 protein (P77).

FIG. 3F illustrates a western blot showing the P77853-Tth-S158-21 protein (SEQ ID No. 1677) that was preheat treated at 37° C. (panel 21, left lane) or 70° C. (panel 21, right lane) for one hour. Also shown are lanes containing protein from the empty vector control (VCT) and wild-type P77853 protein (P77) that was preheat treated in the same manner.

FIG. 3G illustrates a western blot showing the P77853-Tth-S158-25 protein (SEQ ID No. 1678) that was preheat treated at 37° C. (panel 25, left lane) or 70° C. (panel 25, right lane) for one hour. Also shown are lanes containing protein from the empty vector control (VCT) and wild-type P77853 protein (P77) that was preheat treated in the same manner.

FIG. 3H illustrates a western blot showing the P77853-Tth-S158-38 protein (SEQ ID No. 1679) that was preheat treated at 37° C. (panel 38, left lane) or 55° C. (panel 38, right) for four hours. Also shown are lanes containing protein from the empty vector control (VCT) and wild-type P77853 protein (P77) that was preheat treated in the same manner.

FIG. 3I illustrates a western blot showing the P77853-Tth-S158-39 protein (SEQ ID No. 1680) that was preheat treated at 37° C. (panel 39, left lane) or 55° C. (panel 39, middle lane) for four hours, and 70° C. for one hour (panel 39, right lane). Also shown are lanes containing protein from the empty vector control (VCT) and wild-type P77853 protein (P77).

FIG. 3J illustrates a western blot showing the P77853-Tth-S158-42 protein (SEQ ID No. 1681) that was preheat treated at 37° C. (panel 42, left lane) or 55° C. (panel 42, middle lane) for four hours, and 70° C. for one hour (panel 42, right lane). Also shown are lanes containing protein from the empty vector control (VCT) and wild-type P77853 protein.

FIG. 3K illustrates a western blot showing the P77853-Tth-S158-138 protein (SEQ ID No. 1691) that was preheat treated at 37° C. (left lane) or 59° C. (second from left lane) for four hours. Also shown are lanes containing protein from the empty vector control (VCT) and wild-type P77853 protein (P77853).

FIG. 3L illustrates a western blot showing the P77853-Tth-T134-1 protein (SEQ ID No. 1629) (panel 1), P77853-Tth-T134-2 protein (SEQ ID No. 1630) (panel 2), P77853-Tth-T134-3 protein (SEQ ID No. 1631) (panel 3), P77853-Tth-T134-9 protein (SEQ ID No. 1632) (panel 9), P77853-Tth-T134-91 protein (SEQ ID No. 1644) (panel 91), P77853-Tth-T134-48 protein (SEQ ID No. 38) (panel 48), P77853-Tth-T134-80 protein (SEQ ID No. 1640) (panel 80), and P77853-Tth-T134-95 protein (SEQ ID No. 1645) (panel 95) that were preheat treated at 37° C. (left lane in each of the before mentioned panels) and 70° C. (right lane in each of the before mentioned panels) for one hour. Also shown are lanes containing protein from the empty vector control (VCT) and wild-type P77853 protein (P77) that was preheat treated in the same manner. The phenotype of each protein is given above its corresponding lanes.

FIG. 4A illustrates a western blot analysis for S158-19 Tth intein-modified P77853 xylanase (SEQ ID NO: 1675). Protein samples were incubated at 59° C. for different amounts of time (0, 1, 2, 3, 4, and 6 hours). The empty vector (V) and wild-type P77853 control (P) samples are shown on the far right along with a molecular weight ladder. The grayed out middle area is to cover lanes that contained other samples.

FIG. 4B illustrates a western blot analysis for S158-30-103 Tth intein-modified P77853 xylanase (SEQ ID NO: 1701). Protein samples were incubated at either 37° C., 50° C., 59° C., and 65° C. for different amounts of time (1, 2, 3, 4, and 6 hours) as indicated. The empty vector (V) and wild-type P77853 control (P) samples are shown on the far right along with a molecular weight ladder.

FIG. 4C illustrates a western blot analysis for T134-100-101 Tth intein-modified P77853 xylanase (SEQ ID NO: 1711). Protein samples were incubated at either 37° C., 50° C., 59° C., and 65° C. for different amounts of time (1, 2, 4, 6, and 17 hours) as indicated. The empty vector (V) and wild-type P77853 control (P) samples are shown on the far right along with a molecular weight ladder.

DETAILED DESCRIPTION OF THE PREFERRED EMBODIMENTS

Figure 1:
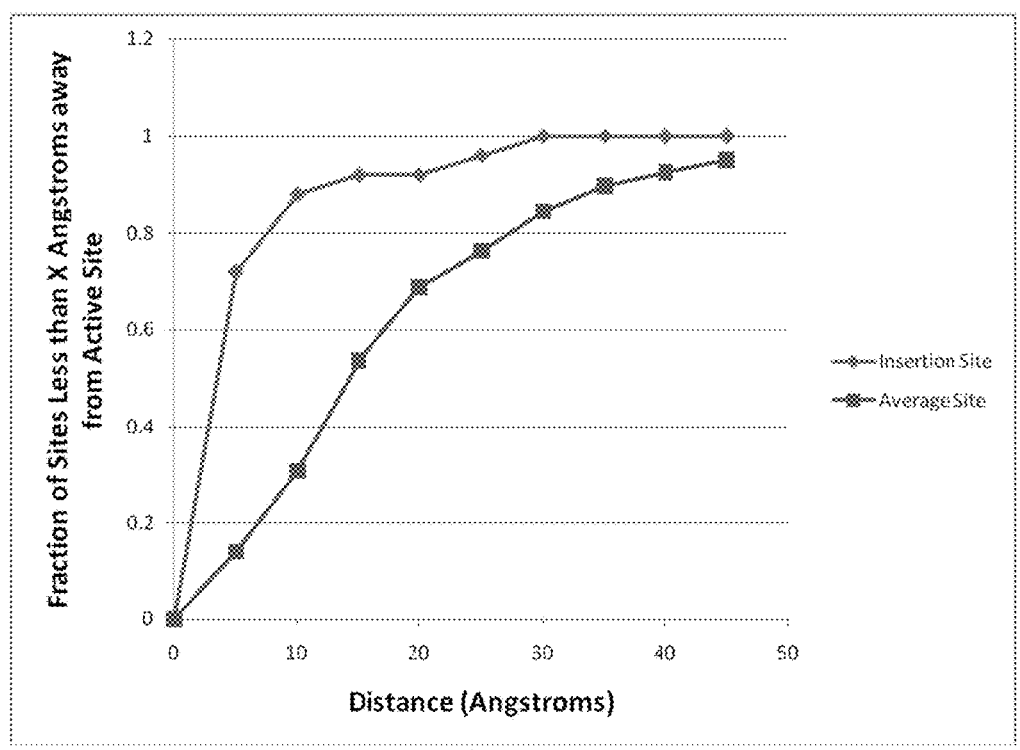
FIG. 1 illustrates intein insertion site distance from a protein active site₀. Diamonds indicated insertion sites and squares indicate other C/S/T sites where no intein is inserted.

Unless defined otherwise, all technical and scientific terms used herein have the meaning commonly understood by a person skilled in the art to which this invention belongs. The methods of the embodiments herein may be substituted or combined with other screening and treatment methods known to those of skill in the art.

As used herein, "extein," refers to the portion of an intein modified protein that is not part of the intein.

As used herein, "amino terminal extein," "N-terminal extein" or "N-extein" are synonymous and refer to an extein that is positioned prior to the N-terminal residue of the intein. The carboxy terminus of an amino terminal extein, N-terminal extein or N-extein is fused to the amino terminus of the intein in an assembled intein modified protein.

As used herein, "carboxy terminal extein," "C-terminal extein," or "C-extein" are synonymous and refer to an extein that is positioned after to the C-terminal residue of the intein. The amino terminus of a carboxy terminal extein, C-terminal extein or C-extein is fused to the carboxy terminus of the intein in an assembled intein modified protein.

As used herein, "target protein" is a protein in which an intein is inserted or that is a candidate for insertion of an intein. Prior to intein insertion, respective portions of the target protein may be referred to as an extein, amino terminal extein, or carboxy terminal extein based on the intended insertion site.

A "target protein" can be an enzyme, and the term "target enzyme" means a "target protein" that is an enzyme.

As used herein, "permissive" or "P" refers to intein modification where the intein modified protein retains function after intein insertion, or the intein is cleaved or spliced from the protein to leave extein or ligated protein with function.

As used herein, "non-permissive" or "NP" refers to intein modification where the intein modified protein has reduced function after intein insertion.

As used herein, "temperature-sensitive" refers to an intein modification where the intein modified protein has greater function after exposure to the temperature or range of temperatures, or the intein is spliced from the protein to leave extein or ligated protein with greater function after exposure to the temperature or range of temperatures.

As used herein, "switching" refers to an activity change of an intein modified protein in response to a physical or chemical condition change. An intein modification that results in a "switching" or "switcher" intein-modified protein is non-permissive prior to the change in condition and permissive after the change in condition. Switching may occur based on the presence of the intein, cleavage of the intein from an extein, or cleavage and ligation of the intein.

As used herein, "temperature-sensitive switcher splicer" or "TSP," refers to an intein modified protein where intein splices in response to an induction temperature or a temperature range. The intein modified protein may be non-permissive prior to exposure to temperatures other than the induction temperature or temperature range and permissive after exposure to the induction temperature or temperature range.

"Isolated nucleic acid," "isolated polynucleotide," "isolated oligonucleotide," "isolated DNA," or "isolated RNA" as used herein refers to a nucleic acid, polynucleotide, oligonucleotide, DNA, or RNA separated from the organism from which it originates or from the naturally occurring genome, location, or molecules with which it is normally associated, or is a nucleic acid that was made through a synthetic process.

"Isolated protein," "isolated polypeptide," "isolated oligopeptide," or "isolated peptide" as used herein refers to a protein, polypeptide, oligopeptide or peptide separated from the organism from which it originates or from the naturally occurring location, or molecules with which it is normally associated.

As used herein, "variant" refers to a molecule that retains a biological activity that is the same or substantially similar to that of the original sequence. The variant may be from the same or different species or be a synthetic sequence based on a natural or prior molecule.

Nucleic acids, nucleotide sequences, proteins or amino acid sequences referred to herein can be isolated, purified, synthesized chemically, or produced through recombinant DNA technology. All of these methods are well known in the art.

As used herein, "operably linked" refers to the association of two or more biomolecules in a configuration relative to one another such that the normal function of the biomolecules can be performed. In relation to nucleotide sequences, "operably linked" refers to the association of two or more nucleic acid sequences, by means of enzymatic ligation or otherwise, in a configuration relative to one another such that the normal function of the sequences can be performed. For example, the nucleotide sequence encoding a presequence or secretory leader is operably linked to a nucleotide sequence for a polypeptide if it is expressed as a preprotein that participates in the secretion of the polypeptide; a promoter or enhancer is operably linked to a coding sequence if it affects the transcription of the coding sequence; and a ribosome binding site is operably linked to a coding sequence if it is positioned so as to facilitate translation of the sequence.

Isolated proteins with controlled activity, isolated nucleic acids that encode the isolated proteins, methods of determining intein insertion sites, and methods to control the activity of proteins are provided. The proteins or nucleic acids may be provided in plants, microbes, and other organisms. Through the control, one or more of the proteins or nucleic acids could be used in the production of fuels, fiber, dough, chemicals, sugars, textiles, pulp, paper, human food, or animal feed. Preferably, the proteins or nucleic acids do not readily interfere with one or more of growth, physiology or other performance characteristics of the expression host. The protein to be controlled may be an enzyme but can be any kind of protein, including non-enzymes, structural proteins, hormones, and others.

One way to control protein activity is with inteins and, preferably, the control allows expression of an intein modified protein with a predefined activity level. Inteins are self-cleaving and self-ligating peptides. The collective attributes of being both self-cleaving and self ligating are referred to as "self-splicing" or "splicing." An intein cleaves from the protein and mediates ligation of the protein sequences (exteins) from which it cleaves to splice the protein. An intein may be inserted internally to the protein sequence or fused terminally to the protein. A intein insertion in a protein may allow control of a protein by yielding a protein that has one activity when the intein is present and another activity after intein cleavage or splicing. In some cases, the intein splicing reaction can be controlled by one or more of a variety of induction conditions. When an activity normally detrimental to the host is reduced, the intein protects the expression host from detrimental growth, physiological, or yield effects of the protein. After expression of the protein, the activity can be changed by exposing the modified protein to reaction conditions that induce intein splicing. Preferably, the protein that results after splicing has increased activity. In an embodiment, the intein modification is non-permissive at low temperatures and permissive at higher temperatures such that the intent modified protein switches when the temperature is changed from low to higher temperatures. In some embodiments, however, the enzyme has lower activity after cleavage and/or ligation. Preferably, a nucleic acid encoding the intein modified protein is codon optimized for expression in a plant. Target proteins that can be modified with an intein in the present embodiments include but are not limited to cell wall degrading enzymes, lignocellulosic degrading enzymes, xylanases and cellulases. All proteins disclosed herein can be a target protein for intein modification.

Preferably, the target protein is modified with an intein selected from Mth, Psp-Pol, mini Psp-Pol (mPsp-Pol), RecA, Tac, Tag, Tth, mini Tth inteins, or derivatives thereof. Mth, Psp-Pol, mini Psp-Pol, RecA, Tac, Tag, Tth, and mini Tth (mTth) inteins preferably included the sequence of SEQ ID NOS: 2, 3, 4-87, 88, 89, 90, 91, and 92-103, respectively. An intein may, however, be from another source or a modified form of a natural intein.

Isolated intein modified xylanases are provided. Preferably, the intein-modified xylanases have a different activity before and after intein cleavage or intein splicing. More preferably, intein cleavage or splicing is induced by exposure of the intein-modified xylanase to an induction condition. The induction condition can be but is not limited to an elevated temperature. The elevated temperature can be within but is not limited to the range of 50-70° C., which includes the temperatures of 50° C. and 70° C. The elevated temperature can be greater than or equal to a temperature in integer increments within the range of 25-70° C. The elevated temperature can be greater than or equal to 50° C., 55° C., 59.9° C., 60° C., 65° C., or 70° C. A nucleic acid encoding an intein modified xylanase is preferably, but not necessarily, codon optimized for expression in a plant. In an embodiment, an intein modified xylanase can be expressed in a transgenic plant.

Isolated intein modified cellulases are provided. Preferably, the intein modified cellulases have a different activity before and after intein cleavage or intein splicing. More preferably, intein cleavage or splicing is induced by exposure of the intein-modified cellulase to an induction condition. The induction condition can be but is not limited to elevated temperature. The elevated temperature can be within but is not limited to the range of 50-70° C., which includes the temperatures of 50° C. and 70° C. The elevated temperature can be greater than or equal to a temperature in integer increments within the range of 25-70° C. The elevated temperature can be greater than or equal to 45° C., 50° C., 55° C., 60° C., 62° C., or 65° C. A nucleic acid encoding the intein modified cellulase is preferably, but not necessarily, codon optimized for expression in a plant. In an embodiment, the intein modified cellulase can expressed in a transgenic plant.

Xylanases that can be target proteins include but are not limited to Beta-1,4-xylanase 229B from *Dictyoglomus thermophilum*, (accession number P77853, SEQ ID NO: 104), endo-1,4-beta-xylanase from *Clostridium thermocellum* (accession number P51584, SEQ ID NO: 105), an alkaline thermostable endoxylanase precursor from *Bacillus* sp. NG-27 (accession number O30700, SEQ ID NO: 106), endo-1,4-beta-xylanase from *Thermomyces lanuginosus* (accession number O43097, SEQ ID NO: 107), and a thermal stable celloxylanase from *Clostridium stercorarium* (accession number P40942, SEQ ID NO: 108). Xylanases can be modified with one or more of several inteins, including, but not limited to Mth, Psp-Pol, mini Psp-Pol, RecA, Tac, Tag, Tth, mini Tth inteins and derivatives thereof. In preferred embodiments, the Mth, Psp-Pol, mini Psp-Pol, RecA, Tac, Tag, Tth, or mini Tth inteins have the sequence of SEQ ID NOS: 2, 3, 4-87, 88, 89, 90, 91, or 92-103, respectively. An intein or multiple inteins can be inserted into one or more of multiple candidate sites in xylanases.

Cellulases that can be target proteins include but are not limited to *Clostridium thermocellum* celK cellulase (accession number O68438 (SEQ ID NO: 109)), the *Thermomonospora fusca* celB cellulase (accession number P26222 (SEQ ID NO: 110)), the Ace1 Endoglucanase E1 from *Acidothermus cellulolyticus* (accession number P54583 (SEQ ID NO: 111)), and the *Nasutitermes takasagoensis* NtEG cellulase (accession number O77044 (SEQ ID NO: 112)). Cellulases can be modified with one or more of several inteins, including, but not limited to Mth, Psp-Pol, mini Psp-Pol, RecA, Tac, Tag, Tth, mini Tth inteins and derivatives thereof. In preferred embodiments, the Mth, Psp-Pol, mini Psp-Pol, RecA, Tac, Tag, Tth, or mini Tth inteins have the sequence of SEQ ID NOS: 2, 3, 4-87, 88, 89, 90, 91, or 92-103, respectively. An intein or multiple inteins can be inserted into one or more of multiple candidate sites in cellulases.

The intein modified protein can be produced by standard molecular biological techniques and then screened. The intein, the target protein, or the intein modified protein can be subjected to mutation and then screened. Screening systems that can be utilized include lamda phage, yeast, or other expression systems that allow production of the protein and/or testing of its physical and/or functional characteristics. From an intein modified protein or mutant intein modified protein population, candidates can be isolated and analyzed further. Further analysis may include DNA sequencing, functional assays, structural assays, enzyme activity assays, and monitoring changes in activity, structure, or splicing in response to induction conditions.

Induction conditions can include exposure of the intein modified protein to changes in physical or chemical conditions such as, but not limited to, changes in temperature, pH, concentration of splicing inhibitors, concentration of ligand, light, salt conditions, and pressure. Natural or mutant inteins can be screened to determine induction conditions. Further, inteins can be derived from organisms adapted to life at a desired induction condition. For example, temperature induced inteins may be isolated from psychrophiles, mesophiles, or thermophiles (for example, *Nanoarchaeum equitans, Pyrococcus abyssi*, or *Pyrococcus* sp.); pH induced inteins may be isolated from acidophiles, alkaliphiles, neutrophiles (for example, *Pyrococcus* sp., *Mycobacterium tuberculosis, Saccharomyces cerevisiae*); and salt induced inteins may be isolated from halophiles. Chemically induced or inhibited inteins have also been identified. As non-limiting examples of chemically induced or inhibited inteins, the vacuolar ATPase subunit (VMA) intein isolated from *Saccharomyces cerevisiae* cleaves inducibly by exposure to DTT, $NH_2OH$, or cysteine; and inteins isolated from *Mycobacterium* and others from *Saccharomyces* have been show to have inhibited splicing in the presence of $Zn^{2+}$. Induction of inhibited inteins may occur by removing the inhibiting condition. Natural inteins may also be mutated and screened to determine if the mutation(s) resulted in an intein that is inducible at a desired induction condition. An intein from any of these sources may be provided in an intein modified protein.

Intein insertion sites can be determined experimentally. To determine if an insertion site will permit intein splicing, the intein-protein fusion gene can be constructed and cloned using known methods in the art, the intein-modified protein can be expressed, and the intein-modified protein tested for its ability to splice either spontaneously or under induction conditions.

To avoid adding any additional amino acids to the protein, and thereby potentially altering the protein's function or activity, native cysteines, serines, and threonines that occur within a protein may be screened as potential intein insertion sites. After insertion, the protein can be tested before and after intein cleavage and/or ligation for alteration of its function.

Inteins can be inserted into a protein at any place by adding a cysteine, serine, or threonine at the new junction site. The cysteine, serine, or threonine can be added by substitution of an amino acid within the protein sequence or insertion of the cystein, serine, or threonine. When an intein is inserted at the new junction site, the carboxy terminus of the intein will be fused to the first amino acid of the amino terminus of the carboxy extein. If an additional cysteine, serine, or thereonine is placed in a protein to facilitate intein insertion, then this amino acid will be left within the protein following the splicing reaction. Additional amino acids left in a mature protein following the splicing reaction may interfere with the protein's function or activity, thus it is preferable to confirm the function and activity of any protein resulting from such a splicing reaction that contains an additional amino acid. Functional assays are known in the art to determine the function of any known protein that has been assigned a function.

Because many proteins contain multiple cysteines, serines, and threonines, it may be desirable to rank order, or even limit, the number of insertion sites that are tested for intein splicing. Three features that can be used to predict an intein insertion site are: A) the local sequence as described by a support vector machine (SVM), B) the distance of the site to the active site residues, and C) the proximity of the insertion site to a local secondary structure (e.g., at or near the end of an alpha-helix or beta-sheet). Preferably, the local sequence and distance to the active site are used to narrow the selection of proposed insertion sites, while the secondary structure element information can be used to prioritize similar insertion sites.

A) The Local Sequence

An SVM method can be used to predict or evaluate intein insertion sites. A suitable training set of known intein insertion sites can be assembled from known native intein insertion sites. Known intein insertion sites sequences for this purpose can be found in the NEB inbase database as described in Perler, F. B. (2002), *InBase, The Intein Database*, Nuc. Acids Res. 30: 383-384, which is incorporated herein in its entirety as if fully set forth. Preferably, the training set intein insertion sites have the sequences of SEQ ID NOS: 1233-1512. One source of protein sequence for this purpose is the NCBI database but many other sources are available. The intein containing proteins corresponding to the preferred training set intein insertion sites of SEQ ID NOS: 1233-1512 have the sequences of SEQ ID NOS: 393-672, respectively. Based on the intein sequences (SEQ ID NOS: 113-392) and the intein containing protein sequences (SEQ ID NOS: 393-672)), the extein sequences of each intein containing protein can be separated from each intein sequence. The N-exteins in the protein sequences of SEQ ID NOS: 393-672 are presented in SEQ ID NOS: 673-952, respectively, and the C-exteins in the protein sequences of SEQ ID NOS: 393-672 are presented in SEQ ID NOS: 953-1232, respectively. For the generation of the SVM sequence prediction, the cassette, which includes the insertion site X and the sequence surrounding X in the N- and C-exteins, is determined. Preferably, the sequence analyzed includes a −3 to +2 (6 amino acids total, numbered as −3, −2, −1, 0, 1, 2) amino acid cassette surrounding X (a sequence of NNNXNN where X is the 0 amino acid). The following description applies to the NNNXNN cassette as a model for the SVM. If a cassette other than NNNXNN is utilized, then the SVM is modified as will be readily apparent from the description herein.

The cassette is converted to a vector V using the following equations:

$$V=[site_{-3}site_{-2}site_{-1}site_{0}site_{+1}site_{+2}]$$

where $$site_i=[aa_iALAaa_iARG \ldots aa_iTRPaa_iTYR]$$

$aa_iN=1$ if amino acid type N is present at site i; otherwise, N=0. This converts the cassette sequence of six amino acids into a 1 by 120 vector. The insertion site cassette for the intein containing proteins of SEQ ID NOS: 393-672 is provided in SEQ ID NOS: 1233-1512, respectively. This set of vectors for insertion site cassettes is used as the true positives control set to train the SVM. From each protein with a true positive, three random NNNXNN cassettes with cysteine, threonine and serine (referred to herein as "C/T/S") at the X (0) position, but no intein insertion, are also chosen from the N and C extein sequences (preferably from SEQ ID NOS: 673-1232) as true negatives. The set of true negatives from extein sequences are then compiled. Preferably, a selected true negative is from the same protein as the true positive insertion site and has the same residue type in the X position as the true positive.

The total SVM for prediction of intein insertion sites is trained on the entire set of intein insertion site sequences, removing any sequences that are identical. This can be done by implementing any one of a number of different methods or programs. One SVM program that can be used for prediction of intein insertion sites is SVM_light V6.02 (Aug. 14, 2008), which is incorporated by reference herein as if fully set forth and is available from Thorsten Joachims Weichgut LLC, Ithaca, N.Y. See also Thorsten Joachims, Making large-Scale SVM Learning Practical. Advances in Kernel Methods—Support Vector Learning, B. Scholkopf and C. Burges and A. Smola (ed.), MIT-Press, 1999, which is incorporated by reference herein as if fully set forth. Briefly, SVM_light V6.02 is an implementation of the support vector machine training method of the above referenced Joachims 1999 publication that accounts for the difficulty of larger training sets associated with large-scale problems. The algorithm is based upon a decomposition strategy that addresses these issues with selecting variables for the working set in an efficient way. With SVM_light V6.02 a linear kernel and cost-factor set to 1 are utilized so the errors in the positive and negative sets are equally weighted.

To test the validity of this method, smaller sets of insertion site cassettes can be chosen for training and testing using the following method: 1) A random set of m true positive training set sites with unique sequences are selected (preferably, m ranges from 1 to 250, and the sequences are preferably selected from SEQ ID NOS: 1233-1512); 2) a corresponding set of true negatives are selected as 3 other random cassettes from the exteins of the intein containing proteins (preferably SEQ ID NOS: 673-1232) from which true positive insertion cassettes were selected, where the true negatives have the same central amino acid X but no intein insertion, and 3) the remaining unique sequences in the group that were not selected in step 1), preferably those remaining in SEQ ID NOS: 1233-1512, can be selected as the test set. The support vectors are then trained using the same method as for the total prediction, and these support vectors are then used to score the test set, which consists of positive values of the known insertion site cassettes, and negative values of all other non-insertion site cassettes selected from the exteins (SEQ ID NOS: 673-1232) with cysteine, threonine, or serine at the 0 position.

The scores for the collection of sites for each protein are then compared and the insertion sites are ranked according to their scores. To create a metric for comparison, each intein insertion site can be assigned a number that is calculated as the ratio of the number of sites with a lower SVM score than the insertion site (L), divided by the number of all sites in the test set minus one (Nn), or L/Nn. A metric of 1 would mean that the insertion site has a higher number than all other sites, while a metric of 0 would mean that it has a lower number than all other sites. This process is preferably repeated 25 times for each size training set, with each run being based upon a random selection of insertion site cassettes from the SEQ ID NOS: 1233-1512, and the corresponding true negative insertion sites selected from the corresponding SEQ ID NOS: 673-1232, to be used for training and testing. Table 1, below, shows the metrics for known intein insertion sites using this training and testing procedure. The average metric for the known intein insertion sites and the standard deviations for each size training set in Table 1 is based on the preferred embodiment including training and test set sequences selected from SEQ ID NOS: 673-1512. For training sets of size 25 or higher, on average the intein insertion site has a metric of 0.75. This was shown to be statistically significant, with an approximate p-value of $10^{-10}$ for a training set of 150 insertion site cassettes. Potential intein insertions sites for any target protein can be screened through the SVM to predict, based on local sequence characteristics, insertion sites that can be used to modify the activity of the target protein. Preferably, candidate insertion sites with a rank of 0.75 or higher are chosen as the site to insert and intein.

TABLE 1

| Training Set Size | Average Metric | Std. Dev. | Number of SV |
|---|---|---|---|
| 1 | 0.57 | 0.068 | 3 |
| 25 | 0.73 | 0.032 | 75 |
| 50 | 0.74 | 0.031 | 150 |
| 75 | 0.75 | 0.045 | 225 |
| 100 | 0.75 | 0.048 | 300 |
| 125 | 0.77 | 0.054 | 375 |
| 150 | 0.75 | 0.052 | 450 |
| 175 | 0.77 | 0.062 | 525 |
| 200 | 0.76 | 0.071 | 600 |
| 225 | 0.77 | 0.070 | 675 |
| 250 | 0.86 | 0.133 | 750 |

A set of preferred NNNXNN intein insertion cassettes include those having the sequence of GGKCGG, GGKSGG, GGKTGG, PGATSP, PGATVP, GAKSLG, PGATSL, PGASPL, PGATGP, AQRSLG, NQPSIV, NQASIV, PNMSSA, GNHSSG, PSHSAY, SLMSSC, TNTSNY, IDTSRN, PSTSAY, QIKSLG, FETCNY, AVLSVN, LVYSAH, AGYSSA, MWGTLR, LSASSY, FAQTQI, GGRSFV, SFVCGF, GFGSNP, NPPTRP, HHRSSS, HRSSSC, RSSSCP, DWNTFN, TFNSPD, DDRSDY, EVATDY, NQVTEL, SSVTFW, LRESVW, RFHTLV, DLSSVT, DNHTWL, DYNTEV, LDVSLY, HYNSIV, ADLSSV, NIITEL, GHQTHI, MRNSPW, RFHTLV, DYNTDD, DKYSWL, LDMSIY, HNQTPT, DIKSWD, WGISDK, SGATDL, YYYSWW, SWWSDG, NFGTYD, GKTTRV, NAPSID, GTQTFD, QYWSVR, IVATEG, GYFSSG, NGNSYL, YGWTRN, YDPSSG, LGKTTR, YFSSGY, IDHTDS, SWSTNE, HTDSWS, NEITIN, DSWSTN, LDQSYV, EDPTIT, SYVTGY, PWGSNS, GSNSFI, TPGSGG, TNYSHP, DGMSYL, PQKCYI, DLISLM, LMSSCM, AGSSQA, AGHSAW, GIATNT, ATNTSN, CDPSGR, PQGTWF, VIDTSR, QGLTSL, SGQSAL, NGDSYW, SGDTGG, GVQSYN, LVYSAH, EFGTTL, FQWTFW, TFWSWN, NPDSGD, GYQSSG, IVESWG, GWSTNP, NLGTID, TGNTTM, NGNSYL, YGWSTN, YQSSGS, SNASGT, or DGGTYD (SEQ ID NOS: 1513-1628, respectively).

B) The Distance of the Insertion Site to the Active Site Residues

Although an intein insertion at any point in a protein is contemplated, an intein insertion site can be selected to be close to the active site of the protein. As shown in FIG. 1, it was discovered that intein insertion sites within 25 angstroms of the active site are more common than those farther away. In FIG. 1, the distance between the insertion site and the active site is measured from i) the atom in the insertion site amino acid that is closest to the active site to ii) the atom in the active site that is closest to the insertion site amino acid. An intein can be inserted at a position that is less than or equal to 25, 24, 23, 22, 21, 20, 19, 18, 17, 16, 15, 14, 13, 12, 11, 10, 9, 8, 7, 6, 5, 4, 3, 2, or 1 angstroms away from the active site. Preferably, an intein insertion site is located at 10 angstroms or less from the active site of the target protein. As used herein, "within 10 angstroms" means 10 angstroms or less. The insertion site can be separated from the active site in the primary or secondary structure of the protein and the distance is measured through physical distance, rather than number of amino acids or secondary structure landmarks. To determine the distance of the insertion site residue to the active site, protein characteristics may be obtained through reference to published data or crystallographic, nuclear magnetic resonance, or homology models. Homology models can be constructed using Swissprot (SWISS-MODEL and the Swiss-PdbViewer: An environment for comparative protein modeling. Guex, N. and Peitsch, M. C. (1997) *Electrophoresis* 18, 2714-2723, which is incorporated by reference herein as if fully set forth) with default parameters. Active site residues can be identified by reference to literature regarding a specific protein, or by using the annotation of active site positions as described by the NCBI genPept files (Database resources of the National Center for Biotechnology Information. David L. Wheeler, Tanya Barrett, Dennis A. Benson, Stephen H. Bryant, Kathi Canese, Vyacheslav Chetvernin, Deanna M. Church, Michael DiCuccio, Ron Edgar, Scott Federhen, Lewis Y. Geer, Yuri Kapustin, Oleg Khovayko, David Landsman, David J. Lipman, Thomas L. Madden, Donna R. Maglott, James Ostell, Vadim Miller, Kim D. Pruitt, Gregory D. Schuler, Edwin Sequeira, Steven T. Sherry, Karl Sirotkin, Alexandre Souvorov, Grigory Starchenko, Roman L. Tatusov, Tatiana A. Tatusova, Lukas Wagner, and Eugene Yaschenko (2007) Nucl. Acids Res. 2007 35: D5-D12, which is incorporated by reference herein as if fully set forth), the Catalytic Site Atlas database (The Catalytic Site Atlas: a resource of catalytic sites and residues identified in enzymes using structural data. Craig T. Porter, Gail J. Bartlett, and Janet M. Thornton (2004) Nucl. Acids. Res. 32: D129-D133; Analysis of Catalytic Residues in Enzyme Active Sites. Gail J. Bartlett, Craig T. Porter, Neera Borkakoti, and Janet M. Thornton (2002) J Mol Biol 324:105-121; Using a Library of Structural Templates to Recognise Catalytic Sites and Explore their Evolution in Homologous Families. James W. Torrance, Gail J. Bartlett, Craig T. Porter, Janet M. Thornton (2005) J Mol Biol. 347:565-81, which are incorporated by reference herein as if fully set forth), and other sources of active site information. Intein insertions at or near other protein sites, such as but not limited to allosteric affector sites, are also contemplated. An insertion site at or near an other protein site is not limited to but can be less than or equal to 25, 24, 23, 22, 21, 20, 19, 18, 17, 16, 15, 14, 13, 12, 11, 10, 9, 8, 7, 6, 5, 4, 3, 2, or 1 angstroms away from the other site.

C) The Proximity of the Insertion Site to a Local Secondary Structure

Intein insertion sites may occur within any type of local secondary structure. Preferably, the intein insertion site is near a loop-β sheet junction or an α-helix. As used in this context, "near" means that the insertion site is within ten amino acids from a loop-β sheet junction or an α-helix junction. As used herein, the insertion site "within ten amino acids" of a loop-β sheet or a loop α-helix means that the insertion site is located before the amino acid that is 10, 9, 8, 7, 6, 5, 4, 3, 2, or 1 amino acids away or at the loop-β sheet or loop α-helix junction. Preferably, an intein is inserted within 2 amino acids of a loop-β-sheet junction or within 2 amino acids of a loop-α-helix junction. As used herein, "within 2 amino acids" means that the intein is inserted before an amino acid that is 2 or 1 amino acid away from the the loop-β sheet or loop α-helix junction. Additional secondary structures where an intein can be inserted include, but are not limited to, at or near the middle of a β-sheet, at or near the middle of a of α-helix, or at or near the middle of a loop.

Summary of Intein Insertion Site Prediction

Based on one or more of A) the local sequence as described by the SVM, B) the distance of the site to the active site residues, and C) the proximity of the insertion site to a local secondary structure (e.g., a of a loop-β-sheet junction or a loop-α-helix junction), intein insertion sites that can be used to control protein activity can be predicted and then tested experimentally. The SVM model can be used to predict an insertion site that can be used to control protein activity on-average within the top 25% of all sites. Intein insertion sites are preferably located at or within 10 angstroms from active site residues. The local secondary structure of intein insertion sites is preferably at or near the junction of loops with either β-sheets or α-helices.

After predicting an insertions site, the protein can be modified with an intein and screened. The screening can include functional assays to determine if the intein modified protein has a permissive, non-permissive, condition-sensitive permissive, temperature-sensitive permissive, or switching phenotype. The screening can include physical assays to determined if the intein in the intein modified protein spliced, cleaved, or remained within the intein-modified protein upon construction or after exposure to induction conditions. Western blots can be used to determine if the intein in the intein modified protein spliced, cleaved, or remained within the intein-modified protein. A combination of functional and physical assays can be employed to determine if the intein modified protein is a condition-sensitive switcher splicer. The combination of functional and physical assays can be used to determine if the intein modified protein is a temperature-sensitive switcher splicer by constructing the protein, exposing it to an induction temperature and conducting the functional and physical assays.

An intein modified protein can be constructed without using the prediction method by inserting an intein prior any C/S/T position. The C/S/T position can be natural or introduced.

An intein modified protein encoding sequence can be mutated. The mutations can be carried out on the intein encoding sequences, the extein encoding sequences, or a combination thereof. Mutated intein modified proteins can then be constructed and screened by functional and/or physical assays.

In an embodiment, one or more isolated proteins having a sequence with at least 70, 75, 80, 85, 90, 91, 92, 93, 94, 95, 96, 97, 98, 99, or 100% identity to a protein having the sequence of any one of SEQ ID NOS: 1629-1784 is provided. In a preferred embodiment, the one or more proteins having less than 100% identity to its corresponding amino acid sequence of SEQ ID NOS: 1629-1784 is a variant of the referenced protein or amino acid. In another embodiment, one or more isolated proteins, polypeptides, oligopeptides, or peptides having a sequence with at least 70, 75, 80, 85, 90, 91, 92, 93, 94, 95, 96, 97, 98, 99, or 100% identity to a protein having the sequence of any one of SEQ ID NOS: 1629-1784 along 6, 10 to 50, 10 to 100, 10 to 150, 10 to 300, 10 to 400, 10 to 500, 10 to 600, 10 to 700, 10 to 800, 10 to 900, or 10 to all amino acids of a protein having the sequence of any of one any one of SEQ ID NOS: 1629-1784 is provided. This list of sequence lengths encompasses every full length protein in SEQ ID NOS: 1629-1784 and every smaller length within the list, even for proteins that do not include over 900 amino acids. For example, the lengths of 6, 10 to 50, 10 to 100, 10 to 150, 10 to 300, 10 to 400, and 10 to all amino acids would apply to a sequence with 453 amino acids. The range of sequence lengths can be extended by increments of 10 to 100N amino acids, where N=an integer of ten or greater, for sequences of 1000 amino acids or larger. Identity can be measured by the Smith-Waterman algorithm (Smith T F, Waterman M S (1981), "Identification of Common Molecular Subsequences," *Journal of Molecular Biology* 147: 195-197, which is incorporated by reference in its entirety as if fully set forth.) Peptides, oligopeptides, or polypeptides having amino acid sequences less than the full length of any one of SEQ ID NOS: 1629-1784 can be used for a number of applications including but not limited to raising an antibody to detect an intein modified protein or a fragment thereof. The antibody can be used to detect whether an intein modified protein or fragment thereof is expressed in a plant, a plant tissue, a plant cell, or a plant sub-cellular region or compartment.

The skilled artisan will realize that variants of the above protein or amino acid sequences can be made by conservative amino acid substitutions, and variants of any of the above sequences with conserved amino acid changes are provided as further embodiments. Proteins with any of the above sequences but having synthetic or non-naturally occurring amino acid analogues (and/or peptide linkages) are included in the embodiments herein. A conservative amino acid substitution can be an amino acid substitution that does not alter the relative charge or size characteristics of the polypeptide in which the amino acid substitution is made. Amino acids are sometimes specified using the standard one letter code: Alanine (A), Serine (S), Threonine (T), Aspartic acid (D), Glutamic acid (E) Asparagine (N), Glutamine (Q), Arginine (R), Lysine (K), Isoleucine (I), Leucine (L), Methionine (M), Valine (V), Phenylalanine (F), Tyrosine (Y), Tryptophan (W), Proline (P), Glycine (G), Histidine (H), Cysteine (C). "Hydrophobic amino acids" refers to A, L, I, V, P, F, W, and M; "polar amino acids" refers to G, S, T, Y, C, N, and Q; and "charged amino acids" refers to D, E, H, K, and R. Conservative amino acid substitution can also include amino acid substitutions of those amino acids that are not critical for protein activity, or substitution of amino acids with other amino acids having similar properties (for example, acidic, basic, positively or negatively charged, polar or non-polar, hydrophobic, charged, et cetera) such that the substitutions of a critical amino acid does not substantially alter activity. The following six groups each contain amino acids that are conservative amino acid substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). One of skill in the art will appreciate that the above-identified substitutions are not the only possible conservative substitutions. For example, in some instances one may regard all charged amino acids as conservative substitutions for each other whether they are positive or negative. In addition, individual substitutions, deletions or additions which alter, add or delete a single amino acid or a small percentage of amino acids in an encoded sequence can also be conservative amino acid substitutions. Conservative amino acid substitution tables providing functionally similar amino acids are well known in the art and conservative amino acid changes as known in the art are contemplated herein. Conservative nucleotide substitution in a nucleic acid encoding an isolated protein are also contemplated in the present embodiments. Conservative nucleotide substitutions include but are not limited to those that affect a conservative amino acid substitution in the encoded amino acid sequence. In addition, degenerate conservative nucleotide substitutions can be made in a gene sequence by substituting a codon for an amino acid with a different codon for the same amino acid.

The isolated proteins, polypeptides, oligopeptides, or peptides and variants thereof can be prepared according to methods for preparing or altering polypeptide sequences, and their encoding nucleic acid sequences, known to one of ordinary skill in the art such as are found in common molecular biology references, for example, Molecular Cloning: A Laboratory Manual, J. Sambrook, et al., eds., Second Edition, Cold Spring Harbor Laboratory Press, Cold Spring Harbor, N.Y. (1989) or Current Protocols in Molecular Biology, F. M. Ausubel, et al., eds., John Wiley & Sons, Inc., New York, which are incorporated herein as if fully set forth. The isolated proteins, polypeptides, oligopeptides, or peptides may include natural amino acids, natural amino acid analogues, or synthetic amino acid analogues.

In an embodiment, one or more isolated nucleic acids having a sequence encoding an amino acid sequence with at least 70, 75, 80, 85, 90, 91, 92, 93, 94, 95, 96, 97, 98, 99, or 100% identity to a protein having the sequence of any one of SEQ ID NOS: 1629-1784 is provided. Preferably, the nucleic acid encoding an amino acid having less than 100% identity to the reference sequence encodes a variant of the reference sequence. In another embodiment, one or more isolated nucleic acids, polynucleotides, or oligonucleotides having a sequence encoding an amino acid sequence with at least 75, 80, 85, 90, 91, 92, 93, 94, 95, 96, 97, 98, 99, or 100% identity to a an amino acid sequence of any one of SEQ ID NOS: 1629-1784 along 6, 10 to 50, 10 to 100, 10 to 150, 10 to 300, 10 to 400, 10 to 500, 10 to 600, 10 to 700, 10 to 800, 10 to 900, or 10 to all amino acids of a protein having the sequence of any of one SEQ ID NOS: 1629-1784 or the complement thereof is provided. This list of sequence lengths encompasses every full length protein in SEQ ID NOS: 1629-1784 and every smaller length within the list, even for proteins that do not include over 900 amino acids. For example, the lengths of 6, 10 to 50, 10 to 100, 10 to 150, 10 to 300, 10 to 400, and 10 to all amino acids would apply to a sequence with 453 amino acids. The range of sequence lengths can be extended by increments of 10 to 100N amino acids, where N=an integer of ten or greater, for sequences of 1000 amino acids or larger. Identity can be measured by the Smith-Waterman algorithm (Smith T F, Waterman M S (1981), "Identification of Common Molecular Subsequences," *Journal of Molecular Biology* 147: 195-197, which is incorporated by reference in its entirety as if fully set forth).

In an embodiment, one or more isolated nucleic acids having a sequence that hybridizes to a nucleic acid having the sequence of any one of SEQ ID NOS: 1785-1923 and 2052-2058 or the complements thereof are provided. The hybridization conditions can be low, preferably moderate, and more preferably high stringency conditions. Examples of hybridization protocols and methods for optimization of hybridization protocols are described in the following books: Molecular Cloning, T. Mainiatis, E. F. Fritsch, and J. Sambrook, Cold Spring Harbor Laboratory, 1982; and, Current Protocols in Molecular Biology, F. M. Ausubel, R. Brent, R. E. Kingston, D. D. Moore, J. G. Seidman, J. A. Smith, K. Struhl, Volume 1, John Wiley & Sons, 2000, which are incorporated by reference in their entirety as if fully set forth. By way of example, but not limitation, procedures for hybridization conditions of moderate stringency are as follows: filters containing DNA are pretreated for 2-4 h at 68° C. in a solution containing 6×SSC (Amresco, Inc., Solon, Ohio), 0.5% SDS (Amersco, Inc., Solon, Ohio), 5×Denhardt's solution (Amersco, Inc., Solon, Ohio), and 100 ug/mL denatured, salmon sperm DNA (Invitrogen Life Technologies, Inc., Carlsbad, Calif.). Approximately 0.2 mL of pretreatment solution are used per square centimeter of membrane used. Hybridizations are carried out in the same solution with the following modifications: 0.01 M EDTA (Amersco, Inc., Solon, Ohio), 100 µg/ml salmon sperm DNA, and 5-20×10$^6$ cpm $^{32}$P-labeled or fluorescently labeled probes can be used. Filters are incubated in hybridization mixture for 16-20 h at 68° C. and then washed for 15 minutes at room temperature (within five degrees of 25° C.) in a solution containing 2×SSC and 0.1% SDS, with gentle agitation. The wash solution is replaced with a solution containing 0.1×SSC and 0.5% SDS, and incubated an additional 2 h at 68° C., with gentle agitation. Filters are blotted dry and exposed for development in an imager or by autoradiography. If necessary, filters are washed for a third time and re-exposed for development. By way of example, but not limitation, low stringency refers to hybridizing conditions that employ low temperature for hybridization, for example, temperatures between 37° C. and 60° C. By way of example, but not limitation, high stringency refers to hybridizing conditions as set forth above but with modification to employ high temperatures, for example, hybridization temperatures over 68° C.

In an embodiment, one or more isolated nucleic acids, polynucleotides, or oligonucleotides encoding at least a portion of any of the amino acid sequences of SEQ ID NOS: 1629-1784 or the complement thereof can be used as hybridization probes or primers. These isolated nucleic acids, polynucleotides, or oligonucleotides are not limited to but may have a length in the range from 10 to 100, 10 to 90, 10 to 80, 10 to 70, 10 to 60, 10 to 50, 10 to 40, 10 to 35, 10 to 30, 10 to 25, 10 to 20 or 10 to 15 nucleotides, preferably from 20 to 30 nucleotide residues, and more preferably having a length of 25 nucleotide residues. In an embodiment, a hybridization probe or primer is 85 to 100%, 90 to 100%, 91 to 100%, 92 to 100%, 93 to 100%, 94 to 100%, 95 to 100%, 96 to 100%, 97 to 100%, 98 to 100%, 99 to 100%, or 100% complementary to a nucleic acid with the same length as the probe or primer and having a sequence chosen from a length of nucleotides corresponding to the probe or primer length within a nucleic acid encoding one of the proteins of SEQ ID NOS: 1629-1784 or the complement of said nucleic acid. In an embodiment, a hybridization probe or primer hybridizes along its length to a corresponding length of a nucleic acid encoding the sequence of one of SEQ ID NOS: 1629-1784 or the complement said nucleic acid. Hybridization can occur under conditions of low, preferably moderate, and more preferably high stringency.

The isolated nucleic acids, polynucleotides, or oligonucleotides of embodiments herein may include natural nucleotides, natural nucleotide analogues, or synthetic nucleotide analogues. Nucleic acids, polynucleotides, or oligonucleotides of embodiments herein may be any kind of nucleic acid including deoxyribonucleic acid (DNA), ribonucleic acid (RNA), or peptide nucleic acid (PNA). SEQ ID NOS: 1785-1923 are listed as a DNA sequences but RNA sequences where U replaces T in SEQ ID NOS: 1785-1923 are also contemplated as nucleic acids of embodiments herein.

Although non-labeled hybridization probes or primers can be used in the embodiments herein, the hybridization probes or primers are preferably detectably labeled and can be used to detect, sequence, or synthesize nucleic acids. Exemplary labels include, but are not limited to, radionuclides, light-absorbing chemical moieties, dyes, and fluorescent moieties. Preferably, the label is a fluorescent moiety, such as 6-carboxyfluorescein (FAM), 6-carboxy-4,7,2',7'-tetrachlorofluoroscein (TET), rhodamine, JOE (2,7-dimethoxy-4,5-dichloro-6-carboxyfluorescein), HEX (hexachloro-6-carboxyfluorescein), or VIC.

In an embodiment, one or more of the isolated nucleic acids, polynucleotides, or oligonucleotides encoding an intein modified protein, a variant of an intein modified protein, or a fragment of an intein modified protein is provided in an expression construct suitable for expression in a desired host. The fragment of an intein modified protein preferably includes a portion of the intein modified protein that substantially retains the activity of the intein modified protein. But the fragment may also have other utility such as but not limited to serving as an antigen to make antibody that can then be used to detect an intein-modified protein or fragment thereof in or extracted from a plant, plant tissue, plant cell, or plant subcellular region or compartment. Preferably, the nucleic acid includes a sequence encoding an amino acid sequence with at least 70, 75, 80, 85, 90, 91, 92, 93, 94, 95, 96, 97, 98, 99, or 100% identity to a protein having the sequence of any one of SEQ ID NOS: 1629-1784. A fragment of the intein modified protein encoding nucleic acid in an expression construct may encode an amino acid sequence having 75, 80, 85, 90, 91, 92, 93, 94, 95, 96, 97, 98, 99, or 100% identity to a an amino acid sequence of any one of SEQ ID NOS: 1629-1784 along 6, 10 to 50, 10 to 100, 10 to 150, 10 to 300, 10 to 400, 10 to 500, 10 to 600, 10 to 700, 10 to 800, 10 to 900, or 10 to all amino acids of a protein having the sequence of any of one any one of SEQ ID NOS: 1629-1784 This list of sequence lengths encompasses every full length protein in SEQ ID NOS: 1629-1784 and every smaller length within the list, even for proteins that do not include over 900 amino acids. For example, the lengths of 6, 10 to 50, 10 to 100, 10 to 150, 10 to 300, 10 to 400, and 10 to all amino acids would apply to a sequence with 453 amino acids. The range of sequence lengths can be extended by increments of 10 to 100N amino acids, where N=an integer of ten or greater, for sequences of 1000 amino acids or larger. The nucleic acid may include a sequence that hybridizes to a nucleic acid having the sequence or complement thereof of one of SEQ ID NOS: 1785-1923. Hybridization can occur under conditions of low, preferably moderate, and more preferably high stringency.

The expression construct may be any suitable expression construct for expression of the intein modified protein or fragment thereof in a suitable host. An embodiment is the expression construct pAG2005 (SEQ ID NO: 1) or any expression construct having at least 90, 91, 92, 93, 94, 95, 96, 97, 98, 99, or 100% identity to the sequence of SEQ ID NO: 1. In a preferred embodiment, a nucleic acid encoding any of the proteins in the preceding paragraph or a fragment thereof is provided in pAG2005. The nucleic acid can be cloned into the KpnI and EcoRI sites in pAG2005 and under control of the rice ubiquitin promoter.

Preferably the isolated nucleic acids, polynucleotides, or oligonucleotides in an expression construct are codon optimized for an expression host. The codon optimization may be but is not limited to codon optimization for a plant, and preferably one of switchgrass, corn, miscanthus, sorghum, sugarcane, wheat, or rice.

Figure 2A:
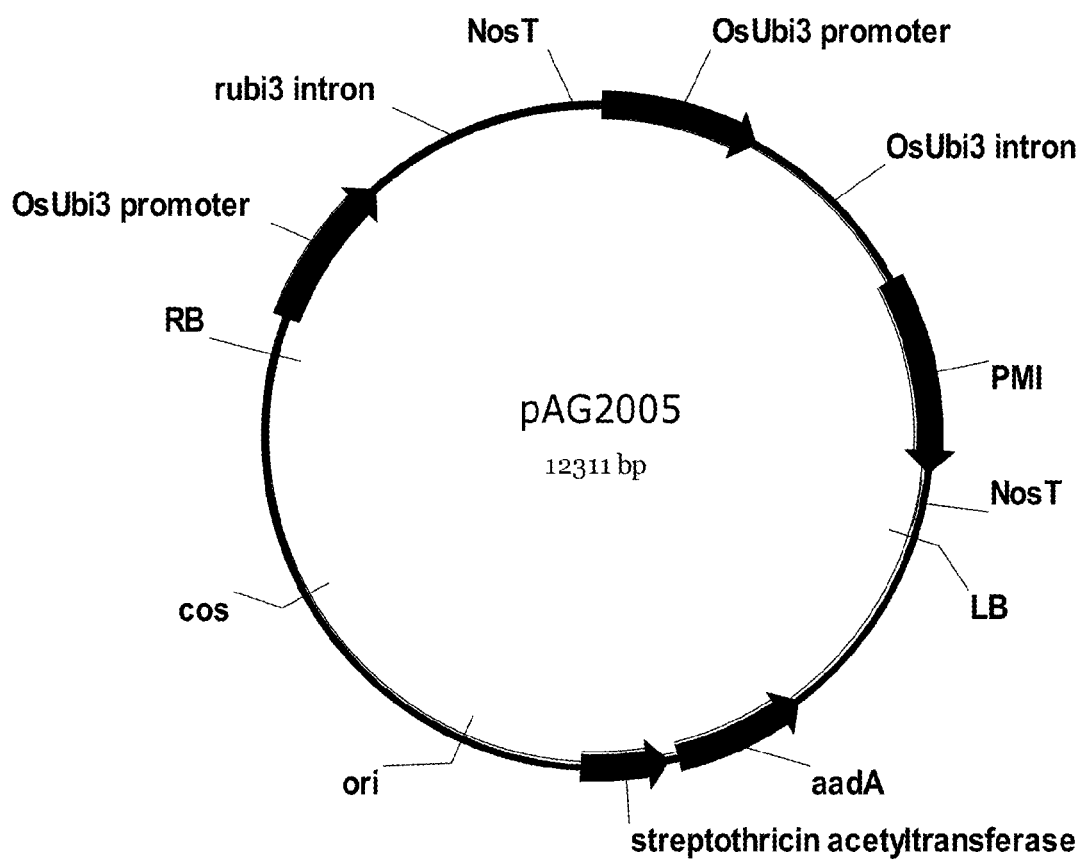
FIG. 2A illustrates a plant expression vector, which is designated pAG2005 (SEQ ID NO: 1).
Figure 2B:
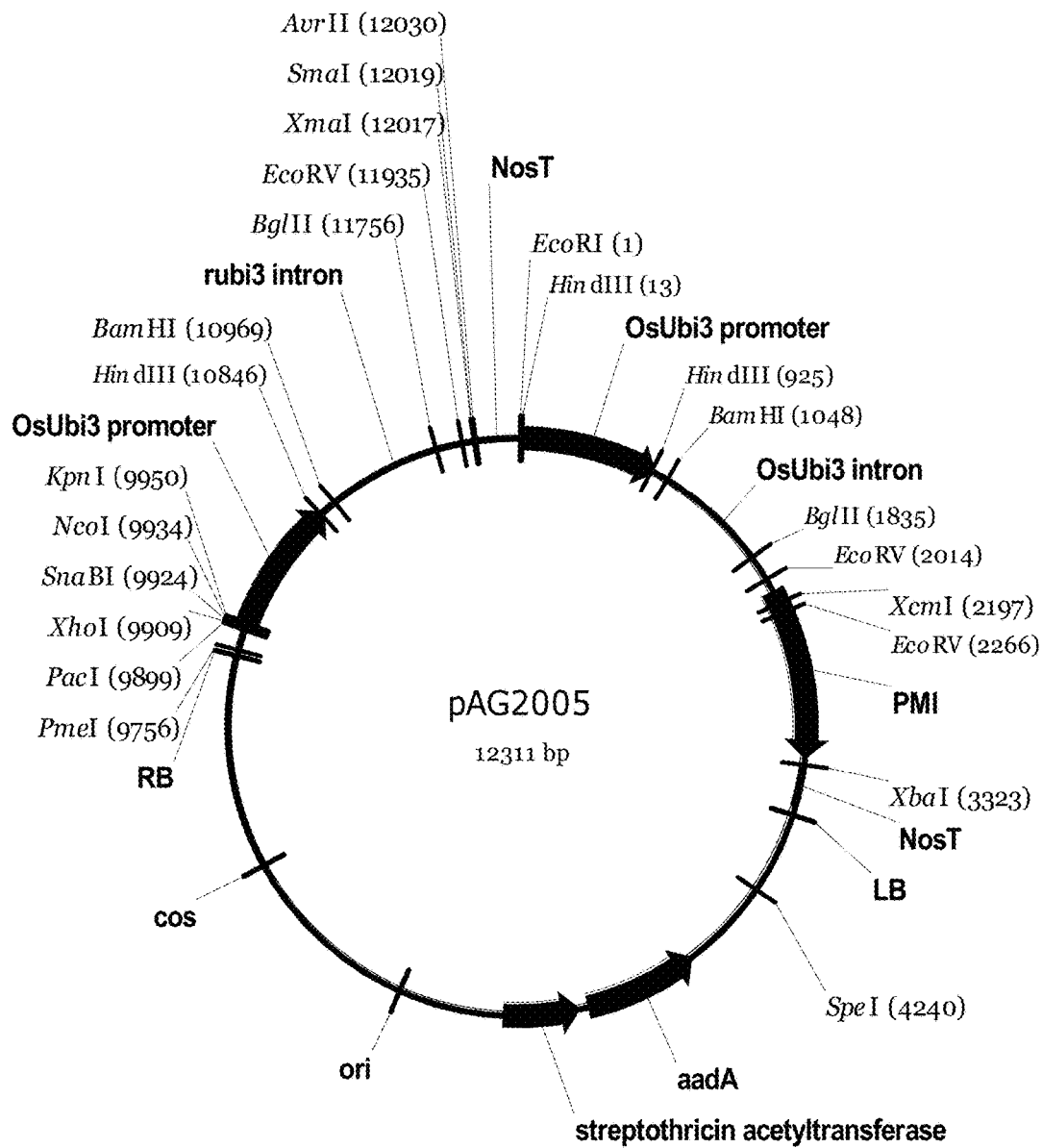
FIG. 2B illustrates pAG2005 (SEQ ID NO: 1) with greater detail.

The host for an expression construct having one or more of the nucleic acids, polynucleotides, or oligonucleotides can be a plant and preferably the plant is a monocotyledonous plant. The monocotyledonous plant can be but is not limited to switchgrass, corn, miscanthus, sorghum, sugarcane, wheat, or rice. The plant could also be a dicotyledonous plant. The dicotyledonous plant can be but is not limited to soy bean, canola, poplar, willow, or rapeseed. Preferably, the expression construct is pAG2005 (SEQ ID NO: 1), which is illustrated in FIGS. 2A-2B. The nucleic acid in the expression construct can be operably linked to a promoter. Preferably, the promoter controls the expression of the intein modified protein or fragment thereof and the promoter can be but is not limited to a plant ubiquitin promoter system, the maize ubiquitin promoter, modified maize ubiquitin promoter that lacks one or more heat shock elements, rice ubiquitin promoter, rice actin 1 promoter, rice actin 2 promoter, gamma-zein promoter, glutelin promoter, maize PR-1 promoter, maize alcohol dehydrogenase 1 promoter, CaMV 19S promoter, CaMV 35S promoter, 35S-enhanced mas promoter, 35S minimal promoter, Arabidopsis PR-1 promoter, tobacco PR-la promoter, opaline synthase promoter, soybean heat shock promoter, octopine synthase promoter, mannopine synthase promoter, a synthetic promoter, an alcohol inducible promoter, a tetracycline inducible promoter, a steroid inducible promoter, a hormone inducible promoter, a promoter based on the ecdysone receptor, a yeast copper responsive promoter, a metallothionein promoter, heat regulated promoter, cold inducible promoter, potato alpha-amylase promoter, light regulated promoter, maize chlorophyll a/b promoter, dark and light-active Cab promoter, tissue specific promoter, root promoter, seed specific promoter, or a constitutive promoter. The promoter could be a constitutive or inducible promoter and is preferably the rice ubiquitin, maize ubiquitin, gamma zein, glutelin, or rice actin promoter. The nucleic acid can be provided in the pAG2005 operably linked to the rice uniquitin promoter, and the construct can be provided in switchgrass, corn, miscanthus, sorghum, sugarcane, wheat, or rice. The nucleic acid can be cloned into the KpnI and EcoRI sites in pAG2005 and under control of the rice ubiquitin promoter. Preferably, if the nucleic acid in any of the above expression constructs encodes an amino acid sequence having less than 100% identity to any one of SEQ ID NOS: 1629-1784, it encodes a variant of the amino acid sequence.

Referring to FIGS. 2A to 2B, pAG2005 (SEQ ID NO: 1) includes an *Oryza sativa* ubiquitin 3 gene promoter with the first intron (OsUbi3 promoter, nucleotides 12-2094), a sequence encoding phosphomannose isomerase enzyme used for selection of transformants (PMI, nucleotides 2104-3279), a left T-DNA border (LB, nucleotides 3674-3698), a ColE1 origin of replication (Ori, nucleotide 6970), a right T-DNA border (RB, nucleotides 9717-9741), a second OsUbi3 promoter with the first intron (nucleotides 9948-12015), and a Nos terminator (nucleotides 12035-12310), where the nucleotide numbers are indexed relative to nucleotide 1 within the EcoRI sequence at the 5' end of the OsUbi3 promoter that drives PMI.

In an embodiment, a transgenic plant is provided with one or more of the isolated nucleic acids, polynucleotides, oligonucleotides, and/or expression constructs herein. The isolated nucleic acid, polynucleotide, oligonucleotide, and/or expression construct can be introduced into the plant by *Agrobacterium* mediated transformation or any other suitable method known in the art. *Agrobacterium*-mediated transformation of immature maize embryos was performed as described in Negrotto et al., (2000) Plant Cell Reports 19: 798-803, which is incorporated by reference herein as if fully set forth.

Embodiments herein also include mutant inteins, which can be but are not limited to uses such as modifying a protein. The mutant inteins include but are not limited to those having at least 70, 75, 80, 85, 90, 91, 92, 93, 94, 95, 96, 97, 98, 99, or 100% identity to a protein having the sequence of any one of SEQ ID NOS: SEQ ID NOS: 92-103, 1675, 1678-1681, 1689, 1691, 1700-1708, and 1710. Embodiments also include a nucleic acid that encodes a mutant inteins including but are not limited to mutant inteins having at least 70, 75, 80, 85, 90, 91, 92, 93, 94, 95, 96, 97, 98, 99, or 100% identity to a protein having the sequence of any one of SEQ ID NOS: SEQ ID NOS: 92-103 1675, 1678-1681, 1689, 1691, 1700-1708, and 1710. Embodiments also include a nucleic acid that encodes a mutant intein that hybridizes to one of the nucleic acid sequence of SEQ ID NOS: SEQ ID NOS: 92-103 1675, 1678-1681, 1689, 1691, 1700-1708, and 1710, which encode the mutant inteins of SEQ ID NOS: SEQ ID NOS: 92-103 1675, 1678-1681, 1689, 1691, 1700-1708, and 1710, or the complement thereof. Hybridization can occur under conditions of low, preferably moderate, and more preferably high stringency. Preferably a mutant intein is inducible to cleave and/or splice from a protein in which it is inserted. Induction conditions can include exposure of the intein to changes in physical or chemical conditions such as, but not limited to, changes in temperature, pH, concentration of splicing inhibitors, concentration of ligand, light, salt conditions, and pressure. The induction condition can be but is not limited to an elevated temperature. The elevated temperature can be within but is not limited to the range of 50-70° C., which includes the temperatures of 50° C. and 70° C. The elevated temperature can be greater than or equal to a temperature in integer increments within the range of 25-70° C. The elevated temperature can be greater than or equal to 50° C., 55° C., 59.9° C., 60° C., 65° C., or 70° C. An intein having at least 70, 75, 80, 85, 90, 91, 92, 93, 94, 95, 96, 97, 98, 99, or 100% identity to a protein having the sequence of SEQ ID NOS: 2, 3, 4-103 and 113-392 and 1675, 1678-1681, 1689, 1691, 1700-1708, and 1710 can be used to modify a protein, enzyme, cellulase, or xylanase. A nucleic acid that hybridizes to a nucleic acid encoding SEQ ID NOS: 92-103 1675, 1678-1681, 1689, 1691, 1700-1708, and 1710 or the complement thereof may be used to modify a protein, enzyme, cellulase, or xylanase at the nucleic acid level.

EXAMPLES

The following non-limiting examples are provided to further illustrate particular embodiments herein.

Example 1—Intein Insertion Site Prediction

The use of A) the local sequence as predicted by an SVM, B) the distance of the site to the active site residues, or C) the proximity of the insertion site to a local secondary structure (e.g., the end of an alpha-helix or beta-sheet) allowed prediction of the insertions sites in the following xylanases and cellulases: The Bacillus sp. NG-27 xylanase (accession number O30700 (SEQ ID NO: 106)); the Clostridium stercorarium xynB xylanase (accession number P40942 (SEQ ID NO: 108)); the Thermomyces lanuginosus xynA xylanase (accession number O43097 (SEQ ID NO: 107)); the Dictyoglomus thermophilum xynB xylanase (accession number P77853 (SEQ ID NO: 104)); the Clostridium thermocellum celK cellulase (accession number O68438 (SEQ ID NO: 109)); the Thermomonospora fusca celB cellulase (accession number P26222 (SEQ ID NO: 110)); the Acidothermus cellulolyticus cellulase (accession number P54583 (SEQ ID NO: 111)); and the Nasutitermes takasagoensis cellulase (accession number O77044 (SEQ ID NO: 112)). For each of these xylanases and cellulases, the distance between each C/T/S site in the enzyme and its active site was calculated based upon the shortest distance between any atom in the C/T/S residue and any atom in any of the residues of the active site. Then, the SVM score of each NNNXNN local sequence cassette, where X is C/T/S, was obtained. The SVM was trained and utilized as described above using the intein insertion cassette sequences of SEQ ID NOS: 1233-1512. The validity of the SVM was tested using: 1) A random set of m (m ranged from 1 to 250) true positive training set sites with unique sequences selected from the intein containing protein library of SEQ ID NOS: 1233-1512; 2) true negatives including 3 other random cassettes from the extein sequences from which the true positive insertion cassettes were selected (SEQ ID NOS: 673-1232); 3) the remaining sequences from the intein insertion site cassettes of SEQ ID NOS: 1233-1512 as true positive test sets, where the known intein insertion sites were filtered to remove sequences in the training set; and 4) true negatives in the test set selected from other C/S/T sites in the extein sequences (SEQ ID NOS: 673-1232). Each true negative in the training set included the same central amino acid X as the corresponding true positive, but there was no intein insertion at that true negative amino acid position.

Sites that were at or closer than 10 angstroms and/or had an SVM score of greater than 0 were included for further analysis. Sites that scored high on the SVM score but were further than 20 angstroms were excluded. Next the secondary structure of all of the candidate site was determined and sites that were located at loop-(α-helix or β-sheet) junctions are prioritized. Sites that were located in long surface loops, that were not immediately adjacent to the active site, or sites that were in the core of the protein were also excluded. A list of such predicted insertion sites is shown in Table 2, below.

TABLE 2

| Enzyme | Predicted Insertion Sites |
| --- | --- |
| O30700 (SEQ ID NO: 106) | T309, T360, S215, T137, S358, T369, T250, S314, S95, S357 |
| P40942 (SEQ ID NO: 108) | T292, T263, S198, T122, T233, S350, S297, T129, S179, S346 |
| O43097 (SEQ ID NO: 107) | T134, S47, S50, T126, T152, S158, T164, S170, T208, S213, S103, T111, S130, T151, S214 |
| O68438 (SEQ ID NO: 109) | T788, T793, S790, T797, S792, S723, T759, T726, S680, S682, S547, S298, S712, C783 |
| P26222 (SEQ ID NO: 110) | S43, S115, S151, S154, S155, S180, S191, T217, T219, T220, S251, S266, T71, T250 |
| P54583 (SEQ ID NO: 111) | T133, S165, S251, T369, S246, S277, T326, T358, T361, S366 |
| P77853 (SEQ ID NO: 104) | S212, S158, S124, T113, T199, T52, S104, S112, S213, S35, T134, T145 |
| O77044 (SEQ ID NO: 112) | T356, S406, S363, S364, C348, S362, T303, S345, S379, S352, T376, S84, S325, T415 |

Example 2—Xylanase Cloning, Expression, and Activity Assays

Figure 35:
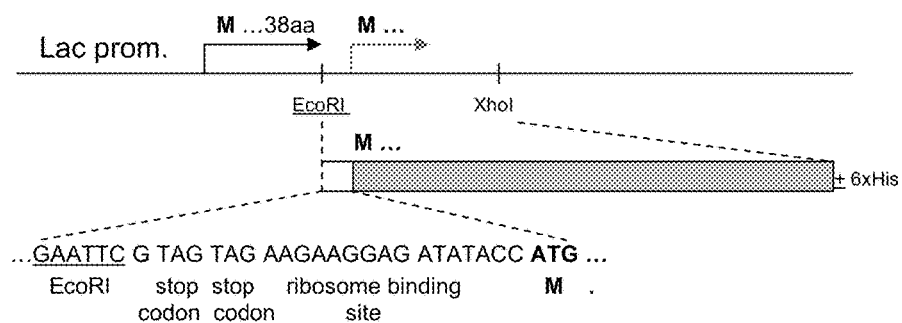
FIG. 35 illustrates the expression cassette in the λ ZAP®II vector.

Wild type xylanases were cloned for expression in the lambda phage and E. coli screening systems. The nucleic acids coding for nine xylanases were PCR amplified with or without a 6 His-tag attached to the carboxy terminal (referred to herein also as the "C-terminal") encoding sequence. These xylanases were the uncultured bacterium GH11 xylanase (accession number EU591743 (SEQ ID NO: 1924)), the Bacillus sp. NG-27 xylanase (accession number O30700 (SEQ ID NO: 106)), the Thermomyces lanuginosus xynA xylanase (accession number O43097 (SEQ ID NO: 107)), the Clostridium stercorarium xynA xylanase (accession number P33558 (SEQ ID NO: 1925)), the Clostridium thermocellum xynY xylanase (accession number P51584 (SEQ ID NO: 105)), the Dictyoglomus thermophilum xynB xylanase (accession number P77853 (SEQ ID NO: 104)), the Clostridium stercorarium xynB xylanase (accession number P40942 (SEQ ID NO: 108)), the Erwinia chrysanthemi xylanase (accession number Q46961 (SEQ ID NO: 1926)), and the Thermotoga sp. xynA xylanase (accession number Q60044 (SEQ ID NO: 1927)). The PCR products were EcoRI/XhoI digested (37° C. for one hr), column purified (MinElute PCR purification kit, Qiagen), and ligated (4° C. for at least 40 hours or 12° C. for at least 12 hours) into a predigested lambda ZAP®II vector (Stratagene). The expression cassette in the λ ZAP®II vector is illustrated in FIG. 35 with gene of interest represented by the gray box. Once the enzyme genes were ligated into the predigested vector, the vectors containing the enzyme genes were packaged into lambda phage (room temperature for 2 hr) with phage packaging extract (Stratagene). The recombinant phage were used to infect XL1-Blue MRF' E. coli cells (Stratagene) and plated out on NZY agar plates (described in the ZAP®-cDNA Gigapack III Gold Cloning Kit, Stratagene) containing 0.2% AZCL-xylan substrate (Megazyme). NZY agar plates include 10 g of NZ amine (casein hydrolysate), 5 g NaCl, 2 g MgSO$_4$*7H$_2$O, 5 g yeast extract, and 15 g agar per liter, pH adjusted to 7.5 with NaOH, and are sterilized in an autoclave as described by the vender (Stratagene). AZCL-xylan substrate (Megazyme) includes azurine-crosslinked xylan, which is hydrolyzed to release dye and yield a blue color. After overnight incubation at 37° C., plates were visually inspected for the development of blue color in and around phage plaques. Xylanase activity was scored as active or inactive based on the ability to hydrolyze the AZCL-xylan substrate and thereby develop a blue color in and around the phage plaque. Selected plaques were confirmed by PCR to contain the subject xylanase gene and replated on NZY agar plates containing 0.2% AZCL-xylan to confirm the xylanase enzymatic activity of the phage plaque.

Each xylanase-expressing phage isolate was amplified in XL1-Blue MRF' E. coli cells to generate high titer phage lysate, which was used in a second infection of XL1-Blue MRF' E. coli cells (Stratagene) in the presence of Isopropyl β-D-1-thiogalactopyranoside (IPTG, Dioxane free, 99% pure; available from Research Products International, Corp.) to induce xylanase expression. Aliquots of individual lysates were incubated at different temperatures ranging from 4° C. to 70° C. for up to four hours, and then cooled at 4° C. for at least two hours. Xylanase activity from each lysate was measured either by Enzchek® kit (Invitrogen™) or by adding AZCL-xylan substrate to 0.2% and incubation at 37° C. or 70° C. for 4 hrs.

Xylanase activity was compared on NZY agar plates containing AZCL-xylan and in liquid assays. P77853 gave the strongest activity with or without C-terminal His-tag, followed by P51584, O43097 and O30700 on NZY agar plates supplemented with AZCL-xylan substrate. In all cases, the 6 His-tag suppressed at least some xylanase activity.

Example 3—Insertion of Inteins into Xylanases

Several inteins were inserted into a subset of the predicted sites, as set forth in Table 2, using a PCR approach. First, three pieces of DNA, "N" (for amino terminal or N-extein fragment) and "C" (for carboxy terminal or C-extein fragment) from a xylanase, and "I" (for intein) from an intein, were generated by PCR separately (Phusion™ Taq polymerase (New England Biolabs), following manufacturer's procedure). The intein fragment, I, was amplified so that it would have a 20 nucleotide overlap with the C-terminus of the N xylanase PCR fragment, and a 20 nucleotide overlapping region with N-terminus of the C xylanase PCR fragment. N, I, and C fragments were then assembled into a contiguous gene encoding an intein-modified enzyme, using a two step PCR (Accumprime™ Taq polymerase Pfx (Invitrogen)). As used herein, "NIC" represents the fusion of the N-terminal DNA fragment of the xylanase to the desired intein, which is also fused to the C-terminal DNA fragment of the xylanase. Although "NIC" is used in the context of an intein modified xylanase in this example, "NIC" can refer to the N-extein, intein, and C-extein countiguous sequence for any intein modified protein.

Generally, the first step in NIC assembly uses 100 ng each of N, I and C encoding nucleic acids in a master mix containing 1× buffer PCR reaction buffer, 200 µM of each dNTP, and 1 unit Pfx Taq polymerase in 12.5 µL with one cycle at 95° C. for two minutes, followed by five three-step thermal cycles of 95° C. for 20 seconds, 45° C. for one minute, and 68° C. for two minutes (alternatively three minutes may be used for longer genes), followed by a final PCR extension at 68° C. for 15 minutes. The second step is NIC amplification, where the master mix containing the assembled NIC is PCR amplified using 0.15 µM primers that hybridize to the 5' and 3' end of the assembled NIC DNA. The thermal cycle used in the second step uses one cycle at 95° C. for two minutes, followed by 27 three-step thermal cycles of 95° C. for 20 seconds, 58° C. for 30 seconds, and 68° C. for three minutes, followed by a final PCR extension at 68° C. for 15 minutes.

Assembled NIC genes, prepared as described above, were gel purified using a QIAquick Gel Extraction kit (Qiagen) and digested with EcoRI and XhoI (New England Biolabs), gel purified using a QIAquick Gel Extraction kit (Qiagen) and ligated with precut lambda ZAP®II vector (Stratagene) following the procedure set forth in example 2, above.

Products were plated on NZY agar plates containing 0.2% AZCL-xylan substrate and the xylanase activity of the plaques was scored after overnight incubation at 37° C. The plates were then incubated for up to four hours at temperatures ranging from 37° C. to 70° C., and xylanase activity was scored for each plaque again. Based on the activity scores following the overnight incubation and the second incubation, each plaque was assigned a phenotype. Plaques that developed a blue color after the overnight incubation at 37° C. remained blue following the second incubation at an elevated temperature and were scored as permissive. Plaques that were inactive and did not develop a blue color following the overnight incubation at 37° C., but did develop a blue color following the second incubation at an elevated temperature were scored as switching. Plaques that were inactive after the overnight incubation at 37° C. and following the second incubation at an elevated temperature were scored as non-permissive. Based on agar plate phenotype of the intein modified xylanase bearing an intein at a specific site, the respective intein insertion was classified as permissive (intein insertion does not interfere with protein function, or intein is spliced during the overnight incubation at 37° C.), non-permissive (intein insertion interferes with protein function at all conditions tested) or switching (xylanase activity is observed following the four hour incubation at high temperature, but activity is not observed following the overnight incubation at 37° C.).

Individual plaques were picked from plates corresponding to each insertion site and excised as phagemid following the manufacture's protocol (Stratagene). Briefly, the lambda ZAP® II vector is designed to enable simple, efficient in vivo excision and recirculation of any cloned insert inside of the lambda vector to form a phagemid containing the cloned insert. To excise cloned inserts into a phagemid, isolated plaques are transferred to a sterile microcentrifuge tube containing 500 µL of SM buffer (Stratagene) and 20 µL of chloroform (Sigma). The tube is vortexed to release the phage particles into the SM buffer. The tube is incubated for at least one hour at room temperature or overnight at 4° C. After incubation, previously prepared XL1-Blue MRF' (Stratagene) and SOLR™ (Stratagene) cells are centrifuged at 1000×g for several minutes. The pellets are resuspended in 25 ml of 10 mM MgSO$_4$ to an OD$_{600}$ of 1.0 (8×10$^8$ cells/ml) in 10 mM MgSO$_4$. Once the cells are resuspended, 200 µL of XL1-Blue MRF' cells at an OD$_{600}$ of 1.0, 250 µL of the desired isolated phage stock (containing >1×10$^5$ phage particles), and 1 µL of the ExAssist® (Stratagene) helper phage (>1×10$^6$ pfu/µL) are placed into a 15 mL polypropylene tube. The tube is incubated at 37° C. for 15 minutes to allow the phage to attach to the cells. After the incubation, 3 mL of LB broth with supplements are added and the mixture is incubated for 2.5-3 hours at 37° C. with shaking. The mixture is then heated at 65-70° C. for 20 minutes to lyse the lambda phage particles and the cells. Following the lysis, the cell debris is pelleted by centrifuging the tube for 15 minutes at 1000×g. The supernatant is decanted into a new sterile tube. This supernatant contains the excised phagemid as filamentous phage particles. To plate the excised phagemids, 200 µL of freshly grown SOLR™ cells ($OD_{600}$=1.0) are mixed with 100 µL of the phage supernatant in a 1.5-mL microcentrifuge tubes. This mixture is incubated at 37° C. for 15 minutes and then 200 µL of the cell mixture is spread on LB-ampicillin agar plates (100 µg/mL) and incubated overnight at 37° C. The resulting colonies contain the excised phagemid. Each phagemid contains an ampicillin resistance marker to support growth in ampicillin containing medium. After confirmation by PCR and DNA sequencing, phagemid clones were cultured in auto induction media (also referred to herein as AIM, obtained as Overnight Express™ Instant TB Medium, and is available from Novagen) overnight. Cells were lysed with FastBreak™ lysis buffer (Promega) and assayed for splicing by western blot.

Intein modified xylanases were analyzed for plaque phenotype on NZY agar plates, and for precursor accumulation and mature xylanase accumulation using a modified western blot procedure (described below in Example 5). A Psp-pol intein (SEQ ID NO: 3) was inserted into P77853 at positions S112 (SEQ ID NO: 1696) and S124 (SEQ ID NO: 1697), which were predicted as insertion sites in Example 1 (above). The plaque phenotype of these positions was scored as permissive for S112, and non-permissive for S124. On the western blot, S112 accumulated some precursor intein modified xylanase and some mature xylanase. S124 accumulated primarily precursor intein modified xylanase. In addition to the predicted sites, the Psp-pol intein was also inserted into several other sites. Among the other sites tested, S63 (SEQ ID NO: 1692), S86 (SEQ ID NO: 1694), S95 (SEQ ID NO: 1695), and S178 (SEQ ID NO: 1698) produced plaques that were scored as switching phenotypes with the Psp-pol intein. On the western blot, these sites accumulated precursor intein modified xylanase when unheated, and also mature xylanase following heat treatment of the phage lysate at 70° C.

A Tag intein (SEQ ID NO: 90) was inserted into P77853 at positions S112, T113, S124, T134, T145, S158, and T199, which were predicted as insertion sites in Example 1 (above). Plaques expressing the P77853 intein modified xylanase with the Tag intein were scored according to their phenotype as follows: S112 (non-permissive), T113 (non-permissive), T124 (non-permissive), T134 (permissive), T145 (switcher), T158 (non-permissive), and T199 (non-permissive). Precursor Tag intein modified xylanase accumulated for the S112, T113, S124, T134, T145, S158, and T199 insertions; however, only the T145 and T199 accumulated mature xylanase. Other cleavage products were observed on the western blot at other insertion sites.

A Tth intein (SEQ ID NO: 91) was inserted into the P77853 xylanase at positions S112, T113, S124, T134, T145, S158, and T199, which were predicted as insertion sites in Example 1 (above). The plaque phenotype of these positions was scored as follows: S112 (permissive), S124 (switcher), T113 (non-permissive), T134 (switcher), S158 (switcher), T145 (non-permissive), and T199 (non-permissive). On the western blot, some precursor intein modified xylanase accumulation was detected for S112, S124, T113, T134, S158, T145, and T199 insertion sites. Mature xylanase was detected on the western blot for S112, S124, T113, S158, and T145.

Mini-Psp-Pol inteins mPspM1L4 (SEQ ID NO: 7) and mPspM5L5 (SEQ ID NO: 36) were inserted into in the P77853 xylanase at the S112 insertion site, which was predicted as insertion sites in Example 1 (above). Plaques expressing the P77853 intein modified xylanase containing either mPspM1L4 or mPspM5L5 were scored as non-permissive phenotypes when inserted at S112, and were not analyzed by western blot. Likewise mini-Psp-Pol inteins mPspM1L4 (SEQ ID NO: 7), mPspM1L7 (SEQ ID NO: 10), mPspM2L5 (SEQ ID NO: 15), mPspM4L3 (SEQ ID NO: 27), mPspM5L2 (SEQ ID NO: 33), mPspM5L5 (SEQ ID NO: 36), and mPspM7L3 (SEQ ID NO: 48) generated non-permissive plaque phenotypes when inserted into the P77853 xylanase at S67. In contrast, these same inteins (mPspM1L4 (SEQ ID NO: 7), mPspM1L7 (SEQ ID NO: 10), mPspM2L5 (SEQ ID NO: 15), mPspM4L3 (SEQ ID NO: 27), mPspM5L2 (SEQ ID NO: 33), mPspM5L5 (SEQ ID NO: 36), and mPspM7L3 (SEQ ID NO: 48)) generated permissive plaques when inserted into the P77853 xylanase at S95 and S178.

A Psp-Pol intein (SEQ ID NO: 3) was inserted into the O30700 xylanase at positions S215, S314, and S357, which were predicted in Example 1 (above). The plaque phenotype of the Psp-pol intein inserted at these positions was scored non-permissive for S215 and S314, but permissive for S357. In contrast, when the mini Psp-Pol inteins mPspM1L4 (SEQ ID NO: 7), and mPspM3L5 (SEQ ID NO: 22) were inserted into the same sites, S314 was scored as permissive, while S215 and S357 were scored as non-permissive.

A Tth intein (SEQ ID NO: 91) was inserted into the O30700 xylanase at positions S95, T137, S215, T250, S358, S314, and S357, which were predicted in Example 1 (above). The plaque phenotype for phage expressing the O30700 xylanase with the Tth intein inserted was scored as: S95 (permissive), T137 (non-permissive), S215 (non-permissive), T250 (non-permissive), S314 (permissive), S357 (non-permissive), and S358 (permissive).

A Mth intein (SEQ ID NO: 2) and Tag intein (SEQ ID NO: 90) were separately fused to the C-terminus of the O30700 xylanase in individual experiments and the resulting intein modified proteins were active after overnight incubation at 37° C., indicating that C-terminal fusion with the Mth and Tag inteins was permissive with O30700.

A Tth intein (SEQ ID NO: 91) was inserted into the O43097 xylanase at positions S47, S50, S103, T111, T126, S130, T134, T151, T152, S158, T164, S170, T208, 5213, and S214, which were predicted in Example 1 (above). Phage plaques expressing the Tth intein modified O43097 xylanase were scored for phenotype as follows: S47 (permissive), T134 (non-permissive), T151 (non-permissive), T152 (non-permissive), S158 (non-permissive), T164 (non-permissive), S170 (non-permissive), T208 (non-permissive), S213 (permissive), S214 (permissive). In the western blot analysis, the Tth intein modified O43097 xylanase precursor was observed for insertion sites S47, S50, S103, T111, S130, T164, S213, and S214, and mature O43097 xylanase was observed for S47, S50, S103, S213, and S214. Phage lysates from phage expressing the Tth intein modified O43097 xylanase at positions T126, T134, T152, S158 were not analyzed by western blot.

As shown above, inserting an intein at an insertion site predicted based on the method described herein may result in an intein modified protein that has a switching phenotype. But the method also leads to permissive candidates or non-permissive candidates that may or may not be cleaved or spliced. Further, intein insertion at sites other than those found by the method can result in a switching phenotype. The method, however, enriches the pool of candidates for insertion sites that are more likely to lead to a switching phenotype.

Example 4—Mutagenesis of Intein Modified Enzymes

Many different methods of protein mutagenesis exist in the art but as a non-limiting example, different specific strategies were used to generate variant intein modified enzymes, as presented below.

Random mutation was introduced into a xylanase, intein modified xylanase, or intein in the examples above using a Mutazyme® (Stratagene) mutagenesis kit. Each time a template DNA is amplified by the Mutazyme®, there is a certain probability that a mutation will be introduced in the newly synthesized DNA. In practice, mutation rates are achieved by varying the amount of template DNA and number of PCR cycles. The mutagenic PCR procedure herein was optimized to introduce 1-2 amino acid mutations per intein when modifying the whole cassette or the intein coding portion.

For whole cassette mutagenesis, five µg of phagemid NIC DNA was PCR amplified for 10 cycles using the GeneMorph® II Random Mutagenesis Kit (Stratagene) with M13 Forward and Reverse primers following manufacturer's protocol. Briefly, five µg of phagemid NIC DNA to be mutagenized is mixed with 1× buffer PCR reaction buffer, 200 µM of each dNTP, 0.15 µM primers complementary to the ends of the NIC DNA, and 2.5 units Mutazyme® II DNA polymerase in a 50 µL final volume with one cycle at 95° C. for two minutes, followed by 10 three-step thermal cycles of 95° C. for 20 seconds, 58° C. for 30 seconds, and 68° C. for three minutes (one minute per kilobase of template), followed by a final PCR extension at 68° C. for 15 minutes. The amplification step was followed by 10 cycles of PCR with cloning primers for each mutagenized NIC DNA using regular Taq polymerase. The Mutagenized NIC DNA library thus generated was gel purified using the QIAquick gel extraction kit (Qiagen), digested with EcoRI and XhoI (New England Biolabs), column purified with the MinElute PCR purification kit (Qiagen), ligated into ZAP® II vector (Stratagene), packaged in lambda phage, as described above, and plated out on NZY agar, as described above.

For intein mutagenesis, five µg of intein encoding plasmid DNA was PCR amplified for 10 cycles with intein end specific primers using the GeneMorph® II Mutagenesis kit (Stratagene) following the manufacturer's protocol. Briefly, five µg of intein DNA to be mutagenized is mixed with 1× buffer PCR reaction buffer, 200 µM of each dNTP, 0.15 µM intein end specific primers and 2.5 unit Mutazyme® II DNA polymerase in a 50 µL final volume and with one cycle at 95° C. for two minutes, followed by 10 three-step thermal cycles of 95° C. for 20 seconds, 58° C. for 30 seconds, and 68° C. for three minutes, followed by a final PCR extension at 68° C. for 15 minutes. The mutagenized intein library was then gel purified using the QIAquick gel extraction kit (Qiagen). Xylanase N-terminal and C-terminal fragments (N and C) were generated by PCR using regular Taq polymerase. A NIC DNA with wild type N and C and a mutagenized intein library, I, was assembled using the PCR procedure described above and cloned into ZAP® II vector for library screening on NZY agar plates as described above.

For intein mutagenesis, a synthetic mutagenesis library of the Tth intein (SEQ ID NO: 91) was also made. This library was designed so that every single amino acid substitution was present at least once at every position in the Tth intein. Once designed, the library was synthesized by Genscript. Xylanase N-terminal and C-terminal fragments (N and C) were generated by PCR using regular Taq polymerase. A NIC DNA with wild type N and C and the synthetic mutagenized Tth intein library, I, was assembled using the PCR procedure described above and cloned for library screening.

The following mutagenized libraries were created by these procedures:
1. A whole cassette mutagenized library where the cassette containing mini-Psp Pol intein mPspM1L4 inserted in P77853 at the S67 site was mutagenized;
2. an intein mutagenized library where the mutagenized mini-Psp Pol intein mPspM1L4 was inserted in P77853 at the S67 site;
3. an intein mutagenized library where a mixture of mutagenized mini-Psp Pol intein mPspM1L4, mPspM2L5, mPspM3L5, mPspM4L3, mPspM5L5, mPspM5L2, and mPspM7L3 was inserted in P77853 at the S67 site;
4. an intein mutagenized library where mutagenized mini-Psp Pol intein mPspM5L5 was inserted in P77853 at the S112 site;
5. a whole cassette mutagenized library where the cassette containing the Tth inserted in P77853 at the T134 site was mutagenized;
6. an intein mutagenized library where the mutagenized Tth was inserted in P77853 at the T134 site;
7. an intein mutagenized library where the mutagenized Tth was inserted in P77853 at the S158 site; and
8. an intein mutagenized library where the mutagenized mini-Psp Pol intein mPspM3L5 was inserted in O30700 at the S106, S215, S295, S314, S357 or S358 sites.

Example 5—Screening of Intein Modified Enzyme Libraries

The mutagenized libraries were screened and candidates were isolated, purified, and confirmed. Individual libraries were titrated to measure the titer (plaque forming unit or pfu per µl) by serial dilution in SM buffer (SM buffer can be prepared by mixing 5.8 g of NaCl, 2.0 g of $MgSO_4*7H_2O$, 50.0 mL of 1 M Tris-HCl (pH 7.5), 5.0 mL of 2% (w/v) gelatin into a final volume of one liter and sterilizing in an autoclave) and plating out on NZY plates. For insertion sites that were scored with a non-permissive phenotype, such as mini-Psp Pol intein mPspM1L4 in S67 site and S112 site of P77853, or various sites in O30700, high density phage titers were used in screening. Up to 10,000 pfu were plated out with 500 uL of XL1-Blue MRF' cells (OD600=0.5) on a 15 cm plate. For libraries derived from intein modified enzymes (for example, libraries made from the insertion of the Tth intein at sites T134 and S158 in the P77853) that had a switching phenotype, 2000 pfu were screened per plate for libraries.

Each library was plated out on agar plates and incubated at 37° C. overnight. Plaques with blue halos were marked representing permissive phenotype mutations. Plates then went through a heat treatment series (500 for 2 hrs and then 70° C. for 2 hrs) to induce phenotype expression of the candidate phage plaques. Individual plaques were picked and diffused into 500 ul SM buffer. Serial dilution in SM buffer were made and used to infect XL1-Blue MRF' cells, which were then plated onto NZY plates. Plates were incubated overnight at 37° C. and then 70° C. for 2 hrs. Plaque phenotypes were confirmed following incubation at both temperatures.

More than 500 intein modified P77853 xylanase candidates have been isolated, purified and phenotype confirmed. Among them about 100 include a mini-Psp Pol intein insertion at site S67, 70 include a M5L5 intein insertion at site S112, 250 include a Tth intein insertion at site T134, and 75 include a Tth intein insertion at site S158. For O30700 xylanase, about 50 picks went through plaque purification, phenotype confirmation and confirmation by PCR.

Phenotype-confirmed candidates were individually excised into phagemid following procedure described above. Most candidates were analyzed by enzyme assay. Candidates showing temperature-sensitive switching activity were analyzed by western blot assay (splicing) and DNA sequence analysis.

Enzyme assays for xylanase activity were conducted as follows: 1) Cultures were inoculated from a single colony containing an excised phagemid and grown overnight in 1 mL of Luria Broth (Luria Broth, LB, can be made by mixing 10 g of NaCl, 10 g of bacto-tryptone, and 5 g of bacto-yeast extract into a final volume of one liter, then adjusting the pH to 7.0 using 5 N NaOH, and sterilizing in an autoclave) supplemented with 100 mg/L ampicillin (AMP, obtained from Sigma) at 37° C. and 300 RPM. 2) 50 µl of cells were transferred to 5 mL of Overnight Express™ Instant TB medium (also called autoinduction medium, herein, or AIM, and is available from Novagen) and grown overnight at 30° C. and 250 RPM. 3) The cultures were centrifuged at 3000 RPM for 15 min. 4) The supernatant was removed and the cell pellets were resuspended in 200 µl lysis buffer (the lysis buffer contains 1× FastBreak Lysis Buffer™ (Promega), 200 mM Sodium Phosphate pH 6.5, and 0.2 µl DNase/mL). 5) The lysate was mixed thoroughly and a 1:10 dilution of the lysate was made in 200 mM Sodium Phosphate pH 6.5. And 6) 100 µl of each dilution was used for the activity assays, which were conducted on samples that were either exposed to splicing induction conditions, such as a heat pretreatment, or unexposed to induction conditions.

For Pretreatment (PT) assays, lysate samples were distributed into aliquots of equal volume, which were incubated at 37° C. or 55° C. for 4 hr, then cooled on ice. 20 µl 0.2% finely grounded AZCL substrate was then added and the samples were mixed well. Reactions were allowed to proceed at 37° C. for at least one hour, but sometimes as long as overnight. Depending upon the intein modified enzyme, and its respective mature enzyme, reaction times, temperatures, conditions, and substrates could vary.

For No Pretreatment (NPT) assays, samples were distributed into aliquots of equal volume and mixed with 2 µl 0.2% finely grounded AZCL substrate. Reactions were allowed to proceed at 37° C. and 70° C. for up to 6 hr. Depending upon the intein modified enzyme, and its respective mature enzyme, reaction times, temperatures, conditions, and substrates could vary as known by one skilled in the art.

In either the Pretreatement (PT) or No Preteatment (NPT) assays, after the reaction time was complete the samples were vortexed and then centrifuged at 4,000 RPM for 7 minutes. From each sample, 50 µl of supernatant was used to measure the absorbance at 590 nm, which is an indication of how active an enzyme or intein modified enzyme was in the sample. Absorbance measurements were made either on a Thermo Scientific Spectrophotometer, or on a BioTek Synergy™ Multi-mode microplate reader in 96 or 384 well round bottom assay plates. If necessary, the samples were centrifuged again to make sure no cellular debris was picked up, and 5× or 10× dilutions in 200 mM Sodium Phosphate pH 6.5 were made when necessary.

Western blot analysis of candidate mutant intein modified enzymes was conducted as follows: 1) A 5 ml AIM culture as grown overnight at 30° C. and 250 RPM and then centrifuged at 3000 RPM for 15 min. 2) The supernatant was removed and the pelleted cells were resuspend in 200 µl of lysis buffer (see above). 3) The lysate was mixed thoroughly and a 1:50 dilution was made using 1× phosphate buffered solution (PBS can be prepared by mixing 137 mmol NaCl, 2.7 mmol KCl, 4.3 mmol of $Na_2HPO_4$, and 1.47 mmol of $KH_2PO_4$ in a final volume of one liter, adjusting the pH to 7.4 with 2N NaOH, and filter sterilizing the solution with a 0.22 micron filter), while the remaining unused sample were stored at −20° C. (a higher dilution may be required depending on expression levels and activities). 4) For each dilution, 50 µl of each dilution was transferred to a sterile centrifuge or PCR tube and heat treated in a 37° C. or 59° C. for 4 hours (the volume may vary depending on needs, but a minimum of 15-25 µl is recommended). 5) An equal volume of 2× loading buffer (2× loading buffer contains 62.5 mM Tris-Cl pH 6.8, 6M Urea, 10% glycerol, 2% SDS, 0.0125% bromophenol blue, and 5% BME) was added; 6) A Biotinylated ladder was prepared with equal volume of urea (the volume of ladder can be calculated by multiplying the number of gels to be used by 20 µl for an 18-well gel (Biorad), or by multiplying the number of gels to be used by 15 µl for a 26-well gel (Biorad)). 7) The samples were vortexed well and then loaded onto the gel (for an 18-well Biorad gel, 30 µl samples were loaded and for a 26-well Biorad gel, 20 µl samples were loaded). 8) The gel was run at 150-175V for 1 hr and then disassembled. 10) The gel was soaked in 1× Transfer (Towbin) Buffer (25 mM Tris base, 192 mM glycine, and 20% methanol) for 15 min. 11) A Whatman-PVDF (dipped in methanol)-gel-Whatman sandwich was assembled and sample was transferred by electroblotting at 15V and at less than 600 mA for 1 hr. 12) The blot was removed and placed in blocking solution containing 2% BSA in TBST (50 mM Tris-HCl, 150 mM NaCl, 0.1% Tween-20). 13) The blot was retained in the blocking solution overnight at 4° C. 14) Blocking solution was decanted and a primary antibody solution (1% BSA in TBST with 1:2,000 of primary antibody that recognizes the enzyme and intein modified enzyme being detected) was added. 15) The blot was washed with TBST 5 times for 5 minutes for each wash. 16) A secondary antibody solution (1% bovine serum albumin (BSA) in TBST with 1:20,000 horseradish peroxidase (HRP) antibiotin and 1:5,000 HRP anti rabbit secondary) was added and the blot was washed with TBST 5 times for 5 minutes each. 17) The blot was immersed in 20 µl of SuperSignal® West Pico Chemiluminescent Substrate (Pierce) for 5 min and then developed in a G:Box™ gel imaging system (Syngene) using successive snapshots, 20× at 1 mM intervals under Chemi setting.

DNA sequencing was done by routine methods in the art.

About 40 candidates from library (1) (mini-psp Pol intein mPspM1L4 in P77853 at S67 site, whole cassette mutagenized) were generated and analyzed on western blot and by DNA sequencing. Over fifty percent of the candidate sequenced had a stop codon in the C-extein, right in or after the linker sequence between the substrate binding domain and the catalytic domain. Whole cassette mutagenesis tended to create a large number of candidates with truncated P77853 protein lacking the entire carbohydrate binding domain, at the S67 insertion site. While spliced mature xylanase was observed in a few candidates (m25, m30), more candidates only had cleavage product (such as m3).

Intein mutagenesis was more efficient in creating amino acid substitutions. With the mutagenic PCR conditions tested, an average of 4 amino acid substitutions were observed in mini-psp Pol candidates, at both the S67 and S112 sites of P77853. These mutations led to precursor cleavage but not intein splicing in most mini-psp Pol candidates.

The Tth intein rendered P77853 intein modified xylanases temperature-sensitive on the NZY agar plate, in an enzyme assay and for accumulation of spliced product on western blot. Based on this result, Tth intein modified xylanase candidates were characterized further.

In order to accurately measure the temperature-sensitive switching and splicing activity of a large number of candidates, the optimum switching conditions (temperature and time) of these candidates was determined. First, a few candidates were tested for effect of heat pretreatment induction conditions on xylanase activity. It was found that 55° C. for 4 hours was the best from the series of temperatures tested (30° C., 37° C., 45° C., 55° C., 70° C.) and times tested (0.5 hr, 1 hr, 2 hr, 3 hr, 4 hr, 6 hr and 20 hrs). Several candidates were tested at a much smaller increment of temperature around 55° C. for 4 hours. 59 C was found to be the optimum temperature for all Tth candidates tested using these conditions.

FIGS. 3A to 3L illustrate western blot data for Tth intein modified P77853, where the intein is inserted at either serine 158 (S158), or threonine 134 (T134) of the P77853 enzyme. The agar plate phenotype is denoted for each sample at the top of the lane. The agar plate phenotypes are given as "SW" for a switcher phenotype, TSP for a temperature sensitive switcher splicer phenotype, and P for a permissive phenotype.

Figure 3A:
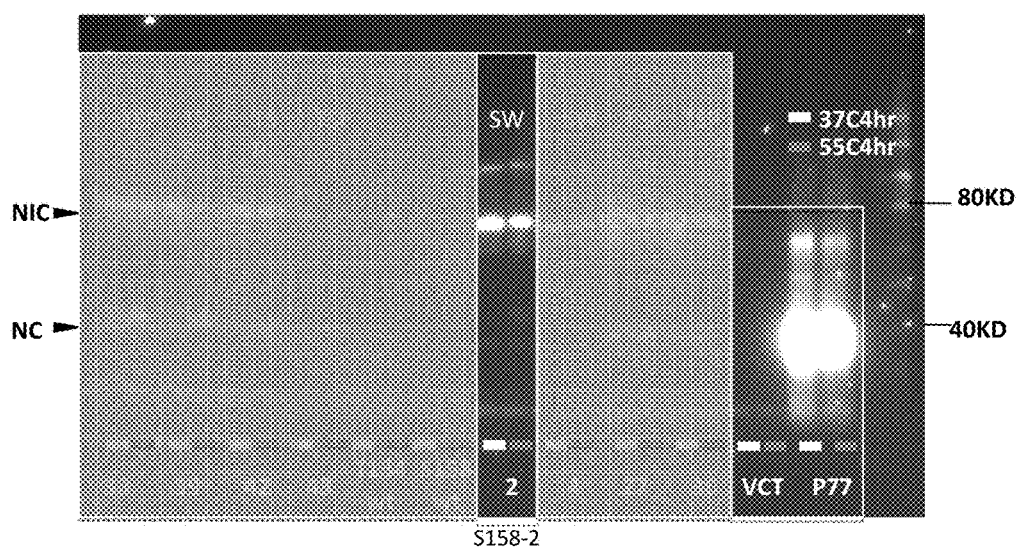
FIGS. 3A to 3L illustrate western blot data for Tth intein modified P77853, where the intein is inserted at either serine 158 (S158), or threonine 134 (T134) of the P77853 enzyme. In some of FIGS. 3A to 3L, parts of the western blot are covered to focus on a specific set of lanes. The agar plate phenotype is denoted for each sample at the top of the lane. The agar plate phenotypes are given as "SW" for a switcher phenotype, TSP for a temperature sensitive switcher splicer phenotype, and P for a permissive phenotype. In each of FIGS. 3A to 3L NIC indicates N-extein, intein, C-extein containing intein modified protein; and NC indicates spliced protein containing the N- and C-exteins.
Figure 3B:
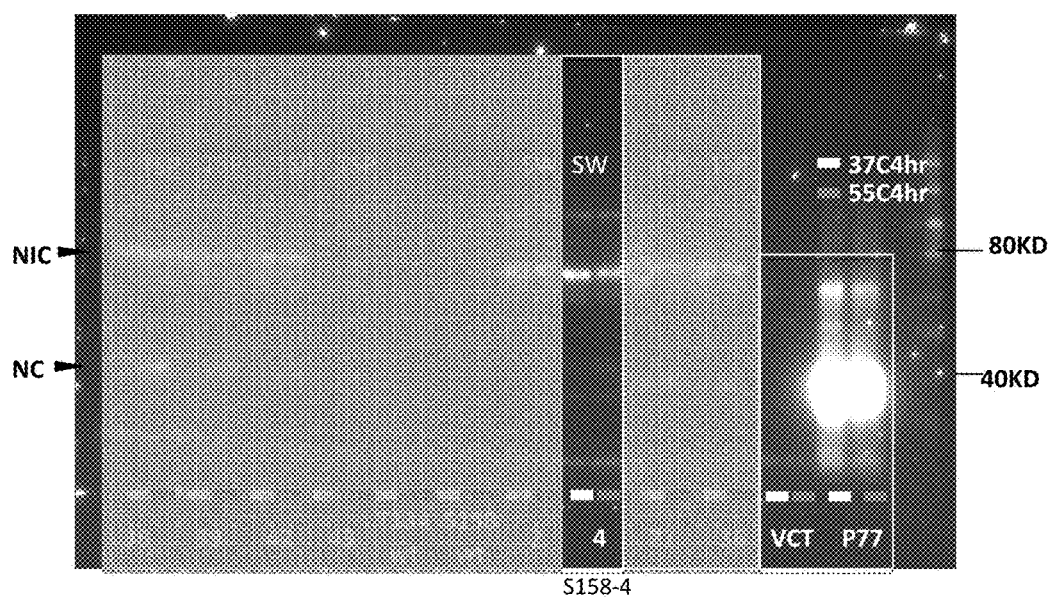
Figure 3C:
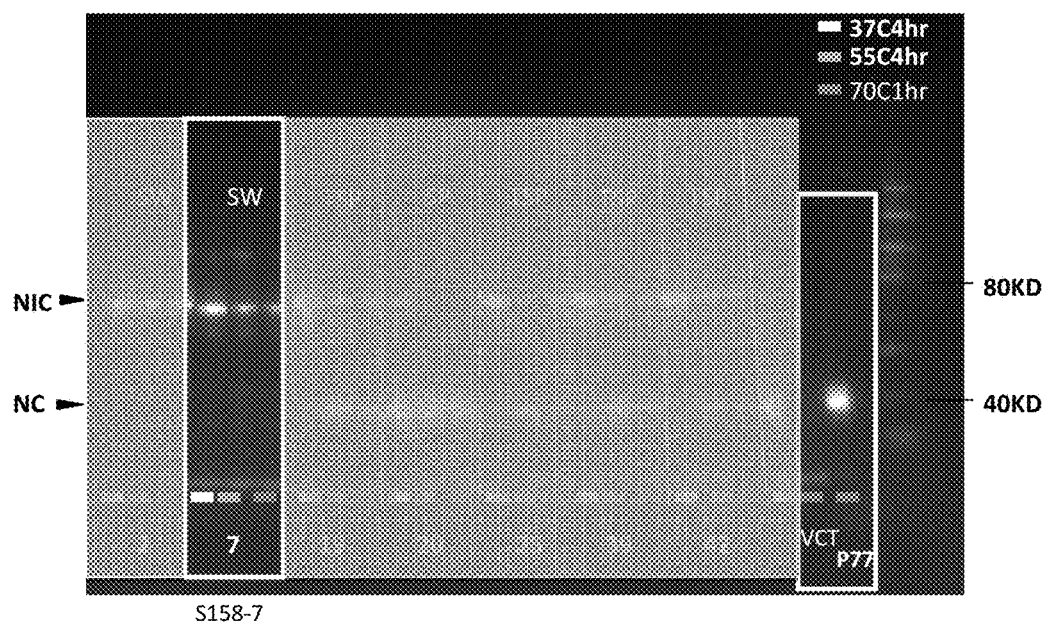
Figure 3D:
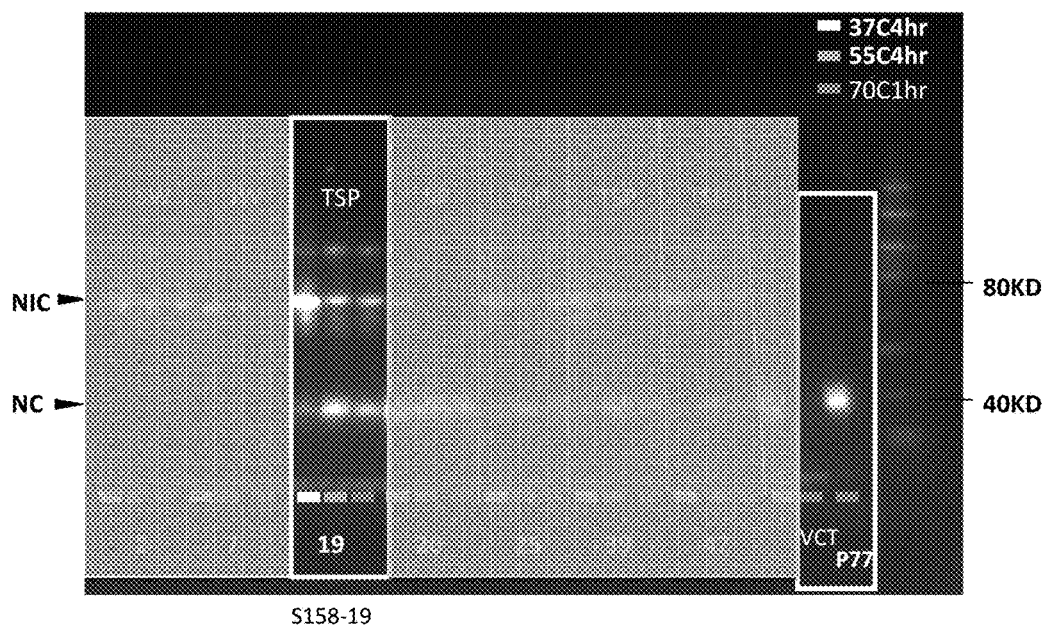
Figure 3E:
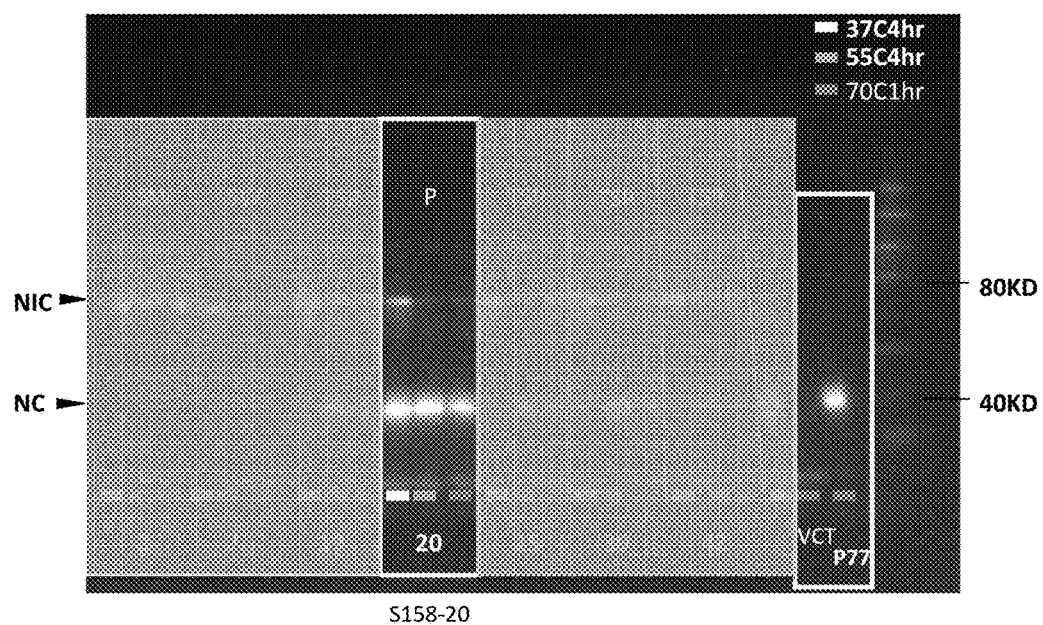
Figure 3F:
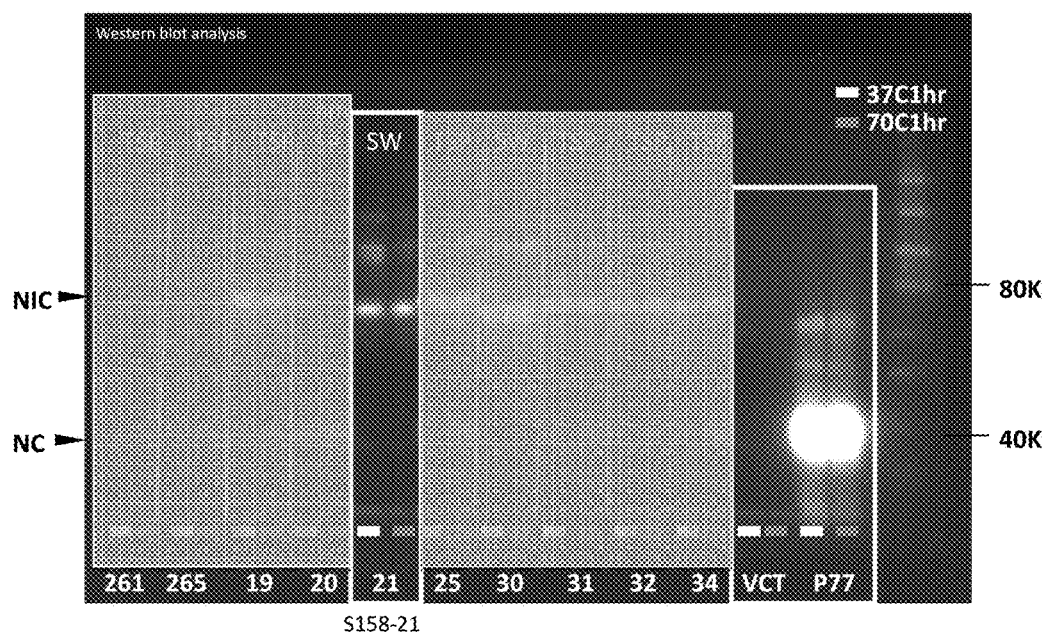
Figure 3G:
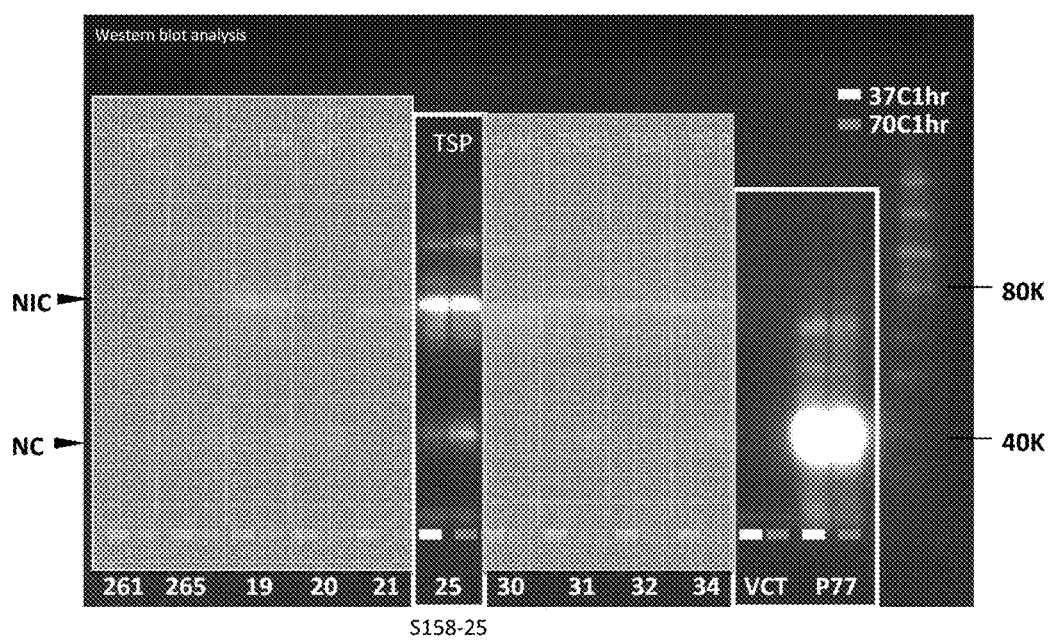
Figure 3H:
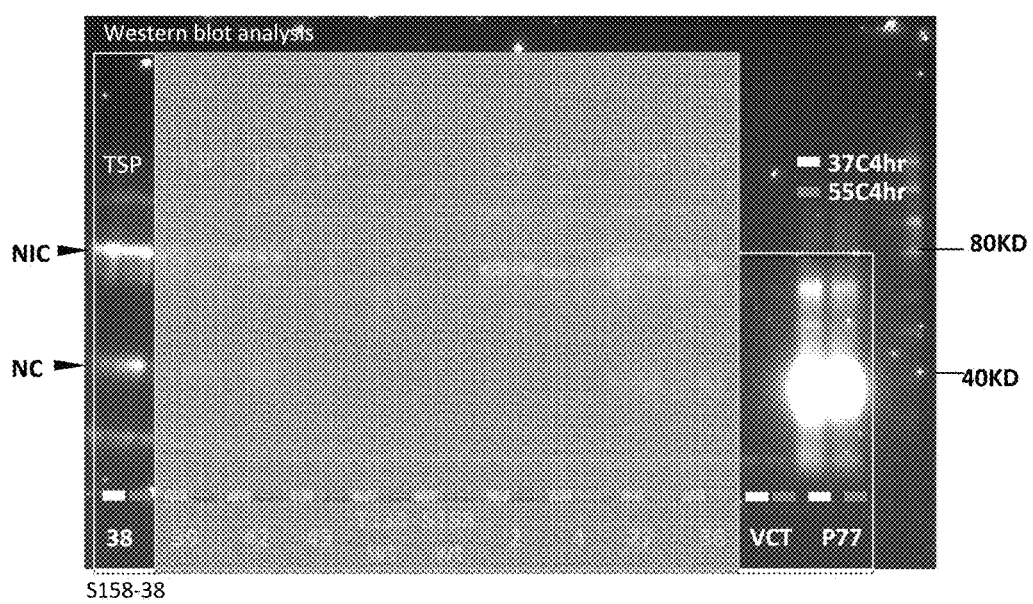
Figure 3I:
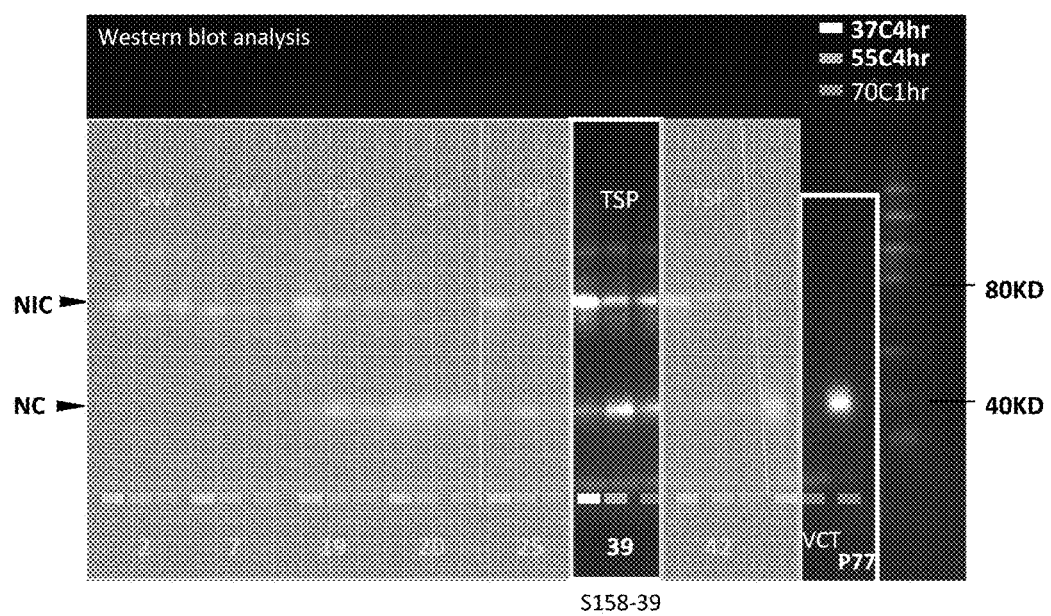
Figure 3J:
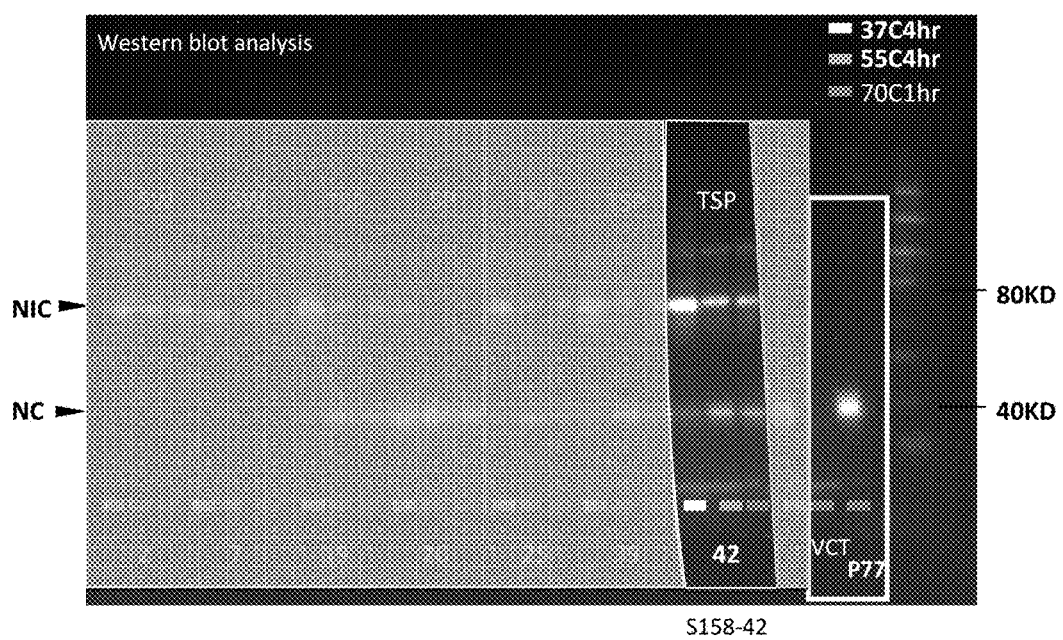
Figure 3K:
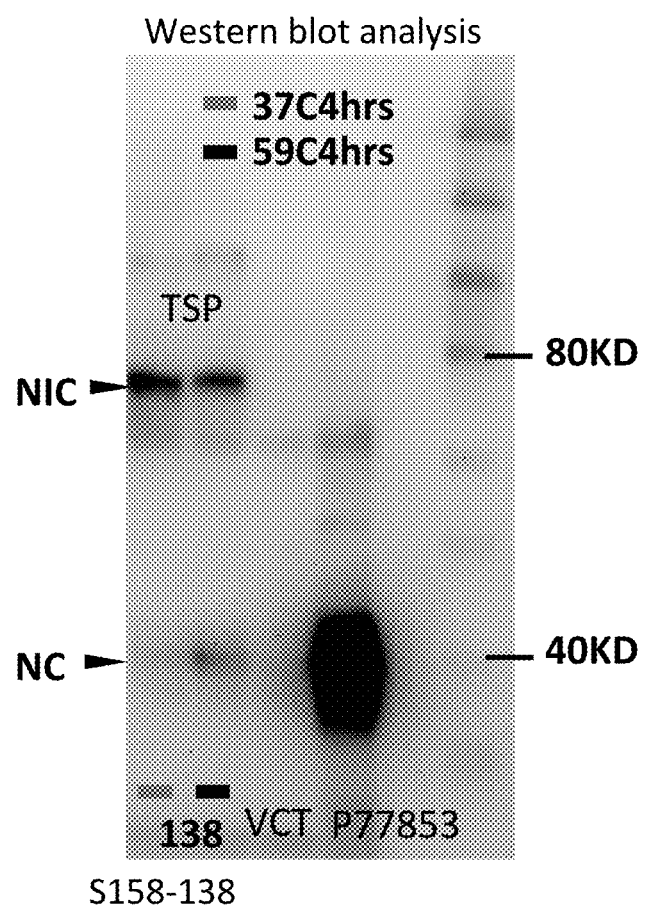

FIG. 3A illustrates a western blot showing the P77853-Tth-S158-2 protein (SEQ ID No. 1672), which had a switcher phenotype in the agar plate assay. FIG. 3B illustrates a western blot showing the P77853-Tth-S158-4 protein (SEQ ID No. 1673), which also had a switcher phenotype in the agar plate assay. FIG. 3C illustrates a western blot showing the P77853-Tth-S158-7 protein (SEQ ID No. 1674), which also had a switcher phenotype in the agar plate assay. FIG. 3D illustrates a western blot showing the P77853-Tth-S158-19 protein (SEQ ID No. 1675), which had a temperature sensitive switcher splicer phenotype. FIG. 3E illustrates a western blot showing the P77853-Tth-S158-20 protein (SEQ ID No. 1676), which had a permissive phenotype in the agar plate assay. FIG. 3F illustrates a western blot showing the P77853-Tth-S158-21 protein (SEQ ID No. 1677), which had a switcher phenotype in the agar plate assay. FIG. 3G illustrates a western blot showing the P77853-Tth-S158-25 protein (SEQ ID No. 1678), which had a temperature sensitive switcher splicer phenotype. FIG. 3I illustrates a western blot showing the P77853-Tth-S158-38 protein (SEQ ID No. 1679), which had a temperature sensitive switcher splicer phenotype. FIG. 3I illustrates a western blot showing the P77853-Tth-S158-39 protein (SEQ ID No. 1680), which had a temperature sensitive switcher splicer phenotype. FIG. 3J illustrates a western blot showing the P77853-Tth-S158-42 protein (SEQ ID No. 1681), which had a temperature sensitive switcher splicer phenotype. FIG. 3K illustrates a western blot showing the P77853-Tth-S158-138 protein (SEQ ID No. 1691), which had a temperature sensitive switcher splicer phenotype.

Figure 3L:
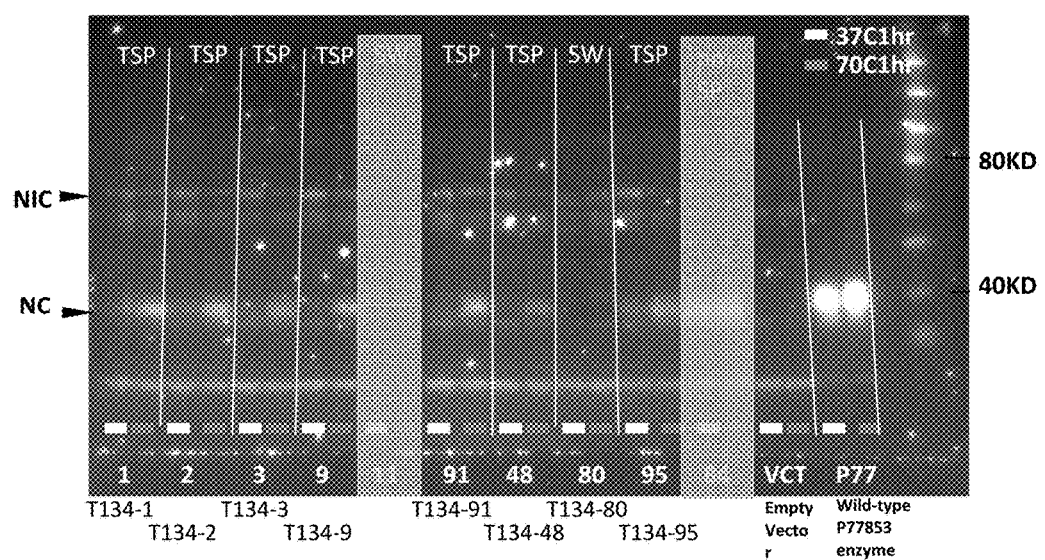

FIG. 3L illustrates a western blot showing the P77853-Tth-T134-1 protein (SEQ ID No. 1629) (panel 1), P77853-Tth-T134-2 protein (SEQ ID No. 1630) (panel 2), P77853-Tth-T134-3 protein (SEQ ID No. 1631) (panel 3), P77853-Tth-T134-9 protein (SEQ ID No. 1632) (panel 9), P77853-Tth-T134-91 protein (SEQ ID No. 1644) (panel 91), P77853-Tth-T134-48 protein (SEQ ID No. 38) (panel 48), P77853-Tth-T134-80 protein (SEQ ID No. 1640) (panel 80), and P77853-Tth-T134-95 protein (SEQ ID No. 1645) (panel 95) that were preheat treated at 37° C. (left lane in each of the before mentioned panels) and 70° C. (right lane in each of the before mentioned panels) for one hour. Also shown are lanes containing protein from the empty vector control (VCT) and wild-type P77853 protein (P77) that was preheat treated in the same manner. The phenotype of each protein is given above its corresponding lanes.

Based on both enzyme assay and western blot data in FIGS. 3A to 3L, incubation at temperatures between 55° C. and 70° C. for 4 hours increases intein splicing in many of the Tth intein modified P77853 xylanase candidates.

The T134 candidates with increased intein splicing on the western blot were tested in liquid assays using pretreatment at 37° C. or 59° C. pretreatment (PT) for four hours followed by a 12 hour reaction at 37° C. with substrate. Alternatively, each had no pretreatment (NPT) and a 5 hour reaction at either 37° C. or 70° C. was conducted. The results are tabulated in Table 3, below. Activity is quantified in an assay that measures the release of a dye from a labeled substrate and is expressed in arbitrary absorbance units, measured on a spectrophotometer or plate reader at a wavelength of 590 nm. The parenthetical percent in the 59° C. column indicates the fold activity change for 59° C. PT in comparison to 37° C. PT, which was calculated as Fold Change=([(activity after 59° C. PT)/(activity after 37° C. PT)]−1)×100. ND means not determined.

TABLE 3

| Intein Modified Protein | Sequence | Activity With 37° C. PT and 37° C. Reaction | Activity With 59° C. PT and 37° C. Reaction | Activity With NPT and 37° C. Reaction | Activity With NPT and 70° C. Reaction |
|---|---|---|---|---|---|
| T134 - 1 | SEQ ID NO: 1629 | 1.275 | 3.140 (146%) | 0.203 | 3.75 |
| T134 - 2 | SEQ ID NO: 1630 | 1.595 | 2.746 (72%) | 0.209 | 3.771 |
| T134 - 3 | SEQ ID NO: 1631 | 0.280 | 0.983 (251%) | 0.368 | 1.711 |
| T134 - 9 | SEQ ID NO: 1632 | ND | ND | ND | ND |
| T134 - 12 | SEQ ID NO: 1633 | 1.515 | 2.090 (38%) | 0.349 | 3.748 |
| T134 - 36 | SEQ ID NO: 1634 | 0.653 | 1.597 (144%) | 0.193 | 5.734 |
| T134 - 42 | SEQ ID NO: 1635 | 0.537 | 1.264 (134%) | 0.165 | 6.830 |

TABLE 3-continued

| Intein Modified Protein | Sequence | Activity With 37° C. PT and 37° C. Reaction | Activity With 59° C. PT and 37° C. Reaction | Activity With NPT and 37° C. Reaction | Activity With NPT and 70° C. Reaction |
|---|---|---|---|---|---|
| T134 - 43 | SEQ ID NO: 1636 | 0.633 | 1.992 (215%) | 0.229 | 5.689 |
| T134 - 45 | SEQ ID NO: 1637 | 0.181 | 0.725 (301%) | 0.073 | 6.068 |
| T134 - 48 | SEQ ID NO: 1638 | 0.662 | 1.084 (64%) | 0.1625 | 1.494 |
| T134 - 49 | SEQ ID NO: 1639 | 8.516 | 10.11 (19%) | 2.800 | 14.38 |
| T134 - 80 | SEQ ID NO: 1640 | 0.064 | 0.522 (715%) | 0.039 | 0.935 |
| T134 - 82 | SEQ ID NO: 1641 | 0.492 | 1.292 (163%) | 0.168 | 3.256 |
| T134 - 83 | SEQ ID NO: 1642 | 1.149 | 3.933 (242%) | 0.358 | 7.648 |
| T134 - 89 | SEQ ID NO: 1643 | 1.543 | 2.017 (31%) | 0.291 | 10.66 |
| T134 - 91 | SEQ ID NO: 1644 | 1.033 | 1.761 (70.1%) | 0.185 | 2.180 |
| T134 - 95 | SEQ ID NO: 1645 | 1.131 | 1.870 (65%) | 0.212 | 3.595 |
| T134 - 98 | SEQ ID NO: 1646 | 1.795 | 2.648 (47%) | 0.450 | 3.793 |
| T134 - 100 | SEQ ID NO: 1647 | 0.564 | 1.210 (115%) | 0.177 | 5.718 |
| T134 - 108 | SEQ ID NO: 1648 | 3.084 | 3.270 (6%) | 0.680 | 3.721 |
| T134 - 110 | SEQ ID NO: 1649 | 2.325 | 2.899 (25%) | 0.475 | 3.704 |
| T134 - 119 | SEQ ID NO: 1650 | 0.587 | 1.778 (203%) | 0.132 | 4.292 |
| T134 - 121 | SEQ ID NO: 1651 | 0.381 | 1.136 (199%) | 0.097 | 3.824 |
| T134 - 122 | SEQ ID NO: 1652 | 0.406 | 1.056 (160%) | 0.129 | 3.353 |
| T134 - 144 | SEQ ID NO: 1653 | 2.303 | 2.647 (15%) | 0.740 | 8.686 |
| T134 - 153 | SEQ ID NO: 1654 | 0.084 | 0.354 (321%) | 0.033 | 1.698 |
| T134 - 167 | SEQ ID NO: 1655 | 0.093 | 0.188 (103%) | 0.023 | 0.908 |
| T134 - 168 | SEQ ID NO: 1656 | 0.030 | 0.361 (1086%) | 0.035 | 0.257 |
| T134 - 173 | SEQ ID NO: 1657 | 0.911 | 1.572 (73%) | 0.198 | 1.883 |
| T134 - 174 | SEQ ID NO: 1658 | 0.240 | 1.278 (432%) | 0.050 | 1.720 |
| T134 - 175 | SEQ ID NO: 1659 | 0.448 | 1.220 (172) | 0.127 | 1.587 |
| T134 - 180 | SEQ ID NO: 1660 | 0.982 | 1.516 (54%) | 0.177 | 2.806 |
| T134 - 190 | SEQ ID NO: 1661 | 0.084 | 0.117 (39%) | 0.013 | 0.940 |
| T134 - 191 | SEQ ID NO: 1662 | ND | ND | ND | ND |
| T134 - 193 | SEQ ID NO: 1663 | 0.175 | 0.834 (376%) | 0.030 | 1.509 |
| T134 - 194 | SEQ ID NO: 1664 | 0.116 | 0.868 (649%) | 0.098 | 2.992 |
| T134 - 195 | SEQ ID NO: 1665 | 1.985 | 2.624 (32%) | 0.392 | 3.776 |
| T134 - 218 | SEQ ID NO: 1666 | 1.692 | 2.472 (46%) | 0.329 | 3.772 |
| T134 - 219 | SEQ ID NO: 1667 | 0.200 | 0.591 (195%) | 0.051 | 1.666 |
| T134 - 225 | SEQ ID NO: 1668 | 0.005 | 0.076 (1434%) | 0.008 | 0.020 |
| T134 - 238 | SEQ ID NO: 1669 | 0.020 | 0.033 (64%) | 0.012 | 0.090 |
| T134 - 248 | SEQ ID NO: 1670 | 0.036 | 0.090 (149%) | 0.090 | 1.672 |
| T134 - 249 | SEQ ID NO: 1671 | ND | ND | ND | ND |

Additional T134 insertion site intein modified P77853 xylanases developed include those in SEQ ID NOS: 1711-1712.

Using the Pretreatment assay (PT) described above, the switching profile was analyzed for temperature induced xylanase reactivation of over 300 Tth intein modified P77853 xylanase candidates in *E. coli* SOLR™ cells (Stratagene). Xylanase activity data was collected for all samples with duplicates and with or without preheat treatment. For preheat treatment, one set of samples was incubated at 37° C. and another at 59° C., both for 4 hours. After cooling the samples on ice, AZCL-xylan substrate was added and the mixture was left at 37° C. for up to 12 hrs. AZCL-xylan substrate was added directly to another two sets of samples without being preheated, and set to react at 37° C. for 5 hrs. The results for the Tth S158 P77853 xylanase are presented in the Table 4, below. While 59° C. preheated samples always had improved activity in general, nearly a third of all Tth intein modified P77853 xylanase candidates demonstrated at least a 2-fold difference (increase) in activity between 37° C. and 59° C. preheat treatment. That is, the activity measured at 37° C. was often twice as high for samples that were preheat treated at 59° C. than for samples that were preheat treated at 37° C. These candidates were further analyzed on western blot. Activity is expressed in arbitrary absorbance units as measured on our plate reader at a wavelength of 590 nm. The parenthetical percent in the 59° C. column indicates the activity change for 59° C. PT in comparison to 37° C. PT, which was calculated as the Percent Fold Change=([(activity after 59° C. PT)/(activity after 37° C. PT)]−1)×100%. ND means not determined.

TABLE 4

| Intein Modified Protein | Sequence | Activity With 37° C. PT and 37° C. Reaction | Activity With 59° C. PT and 37° C. Reaction | Activity With NPT and 37° C. Reaction | Activity With NPT and 70° C. Reaction |
|---|---|---|---|---|---|
| S158 - 2 | SEQ ID NO: 1672 | 1.046 | 2.475 (136%) | 0.189 | 3.751 |
| S158 - 4 | SEQ ID NO: 1673 | 1.108 | 2.795 (152%) | 0.212 | 3.714 |
| S158 - 7 | SEQ ID NO: 1674 | 0.447 | 0.9445 (111%) | 0.131 | 2.296 |
| S158 - 19 | SEQ ID NO: 1675 | 0.820 | 1.502 (83%) | 0.165 | 3.354 |
| S158 - 20 | SEQ ID NO: 1676 | 2.772 | 2.930 (6%) | 0.708 | 3.784 |
| S158 - 21 | SEQ ID NO: 1677 | 0.869 | 2.653 (205%) | 0.195 | 3.460 |
| S158 - 25 | SEQ ID NO: 1678 | 0.568 | 0.926 (63%) | 0.152 | 3.156 |
| S158 - 30 | SEQ ID NO: 1699 | 1.139 | 2.884 (153%) | 0.205 | 3.394 |
| S158 - 38 | SEQ ID NO: 1679 | 0.540 | 0.830 (54%) | 0.139 | 3.069 |
| S158 - 39 | SEQ ID NO: 1680 | 0.399 | 0.565 (42%) | 0.136 | 2.302 |
| S158 - 42 | SEQ ID NO: 1681 | 0.337 | 0.505 (50%) | 0.130 | 1.999 |
| S158 - 107 | SEQ ID NO: 1682 | 0.515 | 1.981 (285%) | 0.911 | 1.572 |
| S158 - 111 | SEQ ID NO: 1683 | 0.392 | 1.160 (196%) | 0.073 | 1.306 |
| S158 - 112 | SEQ ID NO: 1684 | 0.451 | 1.239 (175%) | 0.075 | 0.947 |
| S158 - 113 | SEQ ID NO: 1685 | 0.523 | 1.886 (257%) | 0.077 | 1.622 |
| S158 - 115 | SEQ ID NO: 1686 | 0.850 | 2.790 (288%) | 0.085 | 1.832 |
| S158 - 128 | SEQ ID NO: 1687 | 0.609 | 1.941 (219%) | 0.083 | 1.515 |
| S158 - 131 | SEQ ID NO: 1688 | 0.451 | 1.239 (175%) | 0.075 | 0.947 |
| S158 - 132 | SEQ ID NO: 1689 | 0.320 | 0.625 (95%) | 0.071 | 0.682 |
| S158 - 137 | SEQ ID NO: 1690 | 0.417 | 1.197 (187%) | 0.068 | 1.339 |
| S158 - 138 | SEQ ID NO: 1691 | 0.422 | 1.080 (156%) | 0.072 | 0.992 |

Additional S158 insertion site intein modified P77853 xylanases developed include those in SEQ ID NOS: 1700-1710.

Figure 4A:
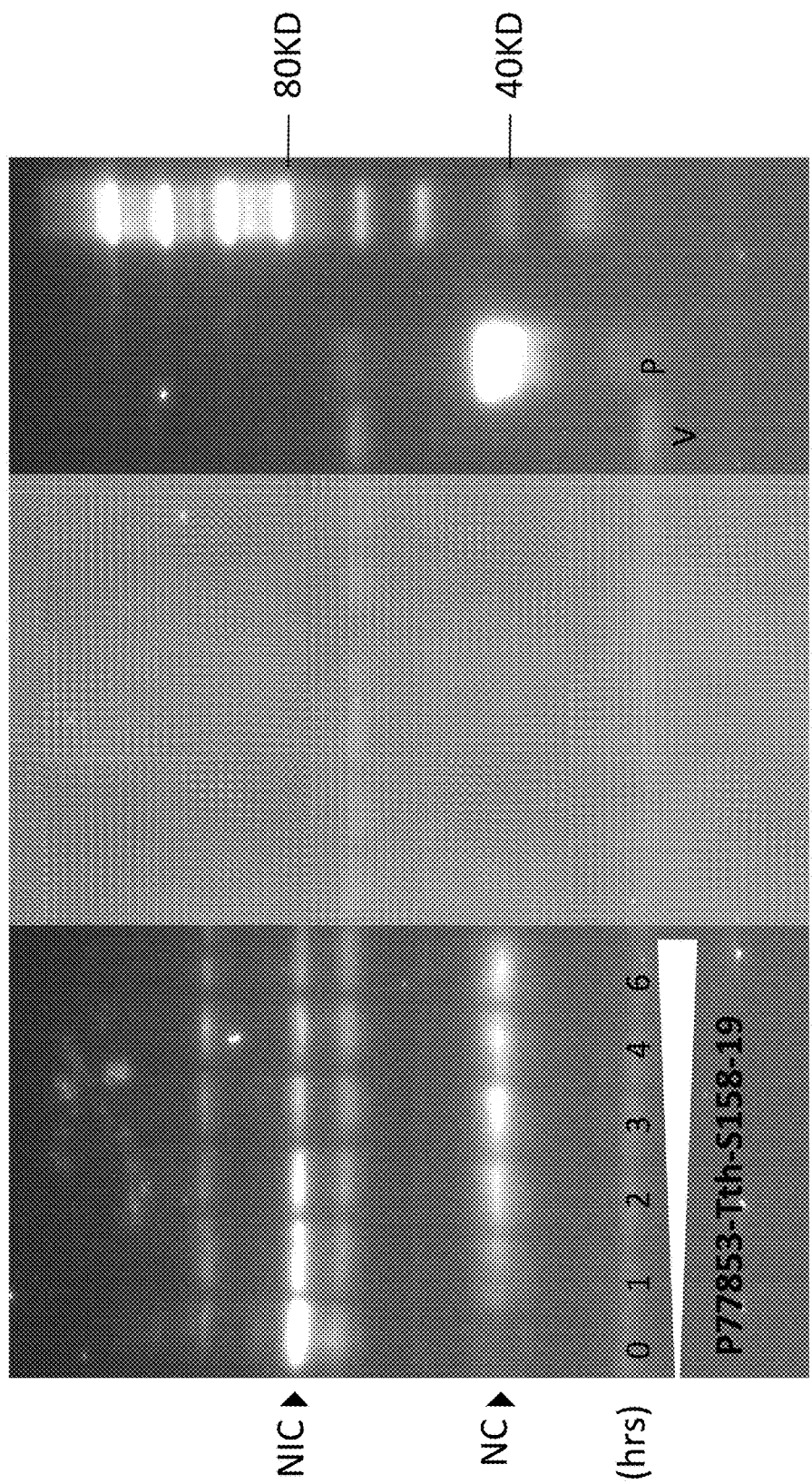
FIGS. 4A to 4C illustrate western blot analysis for S158 Tth intein-modified P77853 xylanase mutants.
Figure 4B:
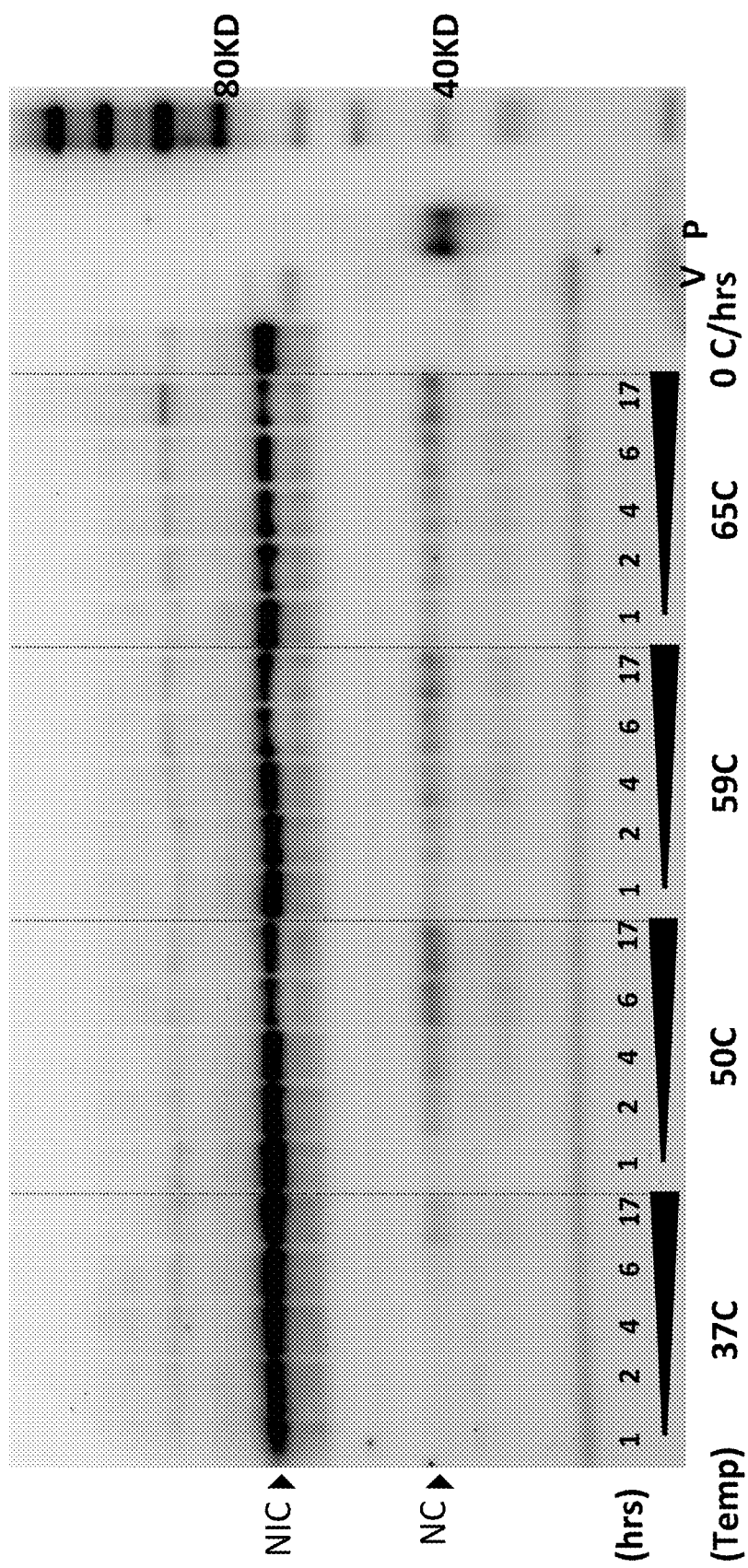
Figure 4C:
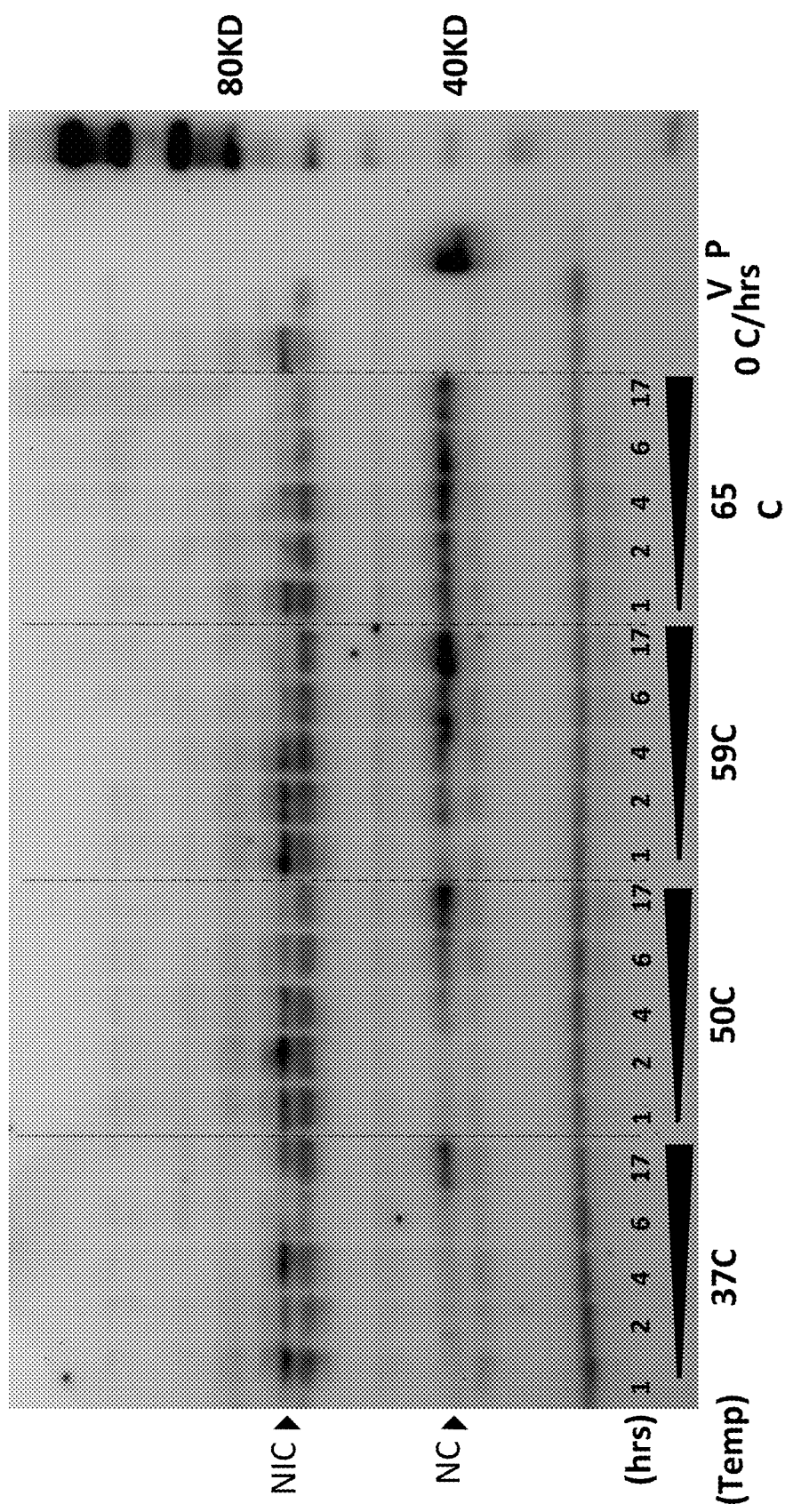

A time course splicing assay was performed and splicing was checked on western blots for each of the intein-modified P77853 candidate samples with either the T134 insertion or S158 insertion in the tables above. FIG. 4A illustrates the time course splicing assay for the S158-19 sample. Protein extracts were incubated at 59° C. for six hours, with samples taken at the 0, 1, 2, 3, 4, and 6 hours, as labeled in FIG. 4A. The right hand side of FIG. 4A shows the empty expression vector control and the wild-type P77853 positive control, as well as molecular weight standards. For Tth intein modified P77853 xylanase candidate S158-19, which accumulated precursor protein to high level, a decreased intein modified enzyme precursor level is correlated directly with accumulation of spliced mature protein. This accumulation of spliced mature xylanase peaked at 4 Hrs. when samples were heat-treated at 59° C. However, splicing at 59° C. was observed over six hours. And splicing was observed at temperatures from 50° C. to 59° C. As time of incubation increased, the amount of NIC Tth intein-modified S158-19 P77853 decreases while the amount of P77853 increases, indicative of increased intein splicing as time progresses during the 59° C. incubation. Similarly, FIG. 4B illustrates a western blot analysis for S158-30-103 Tth intein-modified P77853 xylanase (SEQ ID NO: 1701). Protein samples were incubated at either 37° C., 50° C., 59° C., or 65° C. for different amounts of time (1, 2, 3, 4, and 6 hours) as indicated in FIG. 4B. The empty vector and wild-type P77853 control samples are shown on the far right along with a molecular weight ladder. FIG. 4B shows that as time and temperature increases, there is an increase in mature P77853 enzyme (NC) formation, while there is a decrease in Tth intein-mothfied S158-30-103 P77853 xylanase (NIC). Likewise, FIG. 4C illustrates a western blot analysis for T134-100-101 Tth intein-mothfied P77853 xylanase (SEQ ID NO: 1711). Protein samples were incubated at either 37° C., 50° C., 59° C., or 65° C. for different amounts of time (1, 2, 4, 6, and 17 hours). The empty vector and wild-type P77853 control samples are shown on the far right along with a molecular weight ladder. FIG. 4C shows that as time and temperature increases, there is an increase in wild-type P77853 formation (NC), while there is a decrease in the amount of Tth intein-modified S158-30-103 P77853 xylanase (NIC), indicative of increase intein splicing. This figure shows that as time and temperature increases, there is an increase in P77853 formation, while there is a decrease in the amount of Tth intein-modified S158-30-103, indicative of increase intein splicing.

Unlike the activity-based Pretreatment assay above, which provides quantitative measurement of enzyme reactivation upon preheat treatment, a western blot based splicing assay offers the advantage of a visual demonstration of splicing. About 90 intein modified enzyme candidates which performed well in the Pretreatment assay were analyzed on western blot. For each individual candidate analyzed, a splicing profile was established. A splicing profile consists of precursor level, precursor stability, spliced mature protein level, and cleavage product level, each at two temperatures (usually selected from room temperature, 25° C., 37° C., 50° C., 55° C., 59° C., 65° C., or other temperatures as desired). For some intein modified proteins, samples were taken over time during a heat pretreatment and western blotted to investigate the kinetics of splicing.

Mutations to amino acids capable of enhancing intein switching and splicing (DNA sequence data) were identified for some intein modified enzymes, as described below. These mutations were specific to the specific intein modified enzyme as defined by a single target protein, a single intein, and a single insertion site.

From the Tth intein modified P77853 xylanase candidates, switching candidates and TSP candidates were submitted for DNA sequencing, along with Tth intein modified P77853 xylanase candidates that demonstrated splicing in the western blot analysis. Amino acids both in the Tth intein and P77853 residues at the intein-extein junction were identified that are associated with enhanced switching and splicing. For candidates generated from the insertion of the Tth intein in P77853 at the T134 site of P77853, a Tth intein mutation from P71 (amino acid 71 of the Tth intein) to L, T, or Q (SEQ ID NOS: 1928, 1929, and 1930) is associated with a TSP phenotype. A P136 single insertion (+3 portion of the C-extein) was also associated with a TSP phenotype (SEQ ID NO: 1931). No combination of these mutations (P71 to L/T/Q, or insertion at P136) occurred in any of the TSP candidates that were sequenced. In the case of P136 insertion, there were additional mutations, most noticeably an S to V substitution at S135 site (+2 position of the C-extein (SEQ ID NO: 1932)). These double mutants were also classified as belonging to the TSP family. The remaining candidates from the 61 displayed a switching phenotype but temperature-sensitive splicing was difficult to detect.

Tth intein-modified P77853 xylanases, constructed by intein insertion at S158, were analyzed and different TSP constructs were identified. Seventeen R51G(S) (amino acid 51 of the Tth intein) substitutions in the Tth intein (SEQ ID NO: 91) were identified (SEQ ID NOS: 1675, 1678-1681, 1689, 1691, 1700-1708, and 1710) and all were associated with TSP. Sequencing data suggests that these intein mutations that correlate with the TSP phenotype play a role in the temperature exposure-dependent splicing of the Tth intein-modified P77853 xylanases when inserted at these specific locations. Additional evidence to support TSP element's role in splicing comes from structural analysis of the mutations on the surface of the intein. Both R51 and P71 of the Tth are predicted to be in close proximity to the intein-extein junction and therefore the active site for intein cleavage and splicing.

Summary of Results from Examples 1-5

One xylanase, P77853, was modified with an intein and analyzed as set forth above. Multiple P77853 mutagenized intein libraries were created by inserting a mutagenized intein into the enzyme. Multiple mutagenized inteins and multiple intein insertion sites were used to create the library. Each modified enzyme in the library had a single mutagenized intein inserted into a single insertion site. From about 10 million mutants in the library, 500 candidates were isolated. The candidates were analyzed by DNA sequencing, enzyme activity assay, temperature-sensitive changes in activity and splicing. It was established that preheat treatment at a temperature near 60° C. most often induces switching; i.e., activity changes, of the intein-modified enzyme. In some candidates, switching is correlated with intein splicing. It was also found that particular amino acid changes in inteins and exteins, particularly near the intein-extein junction are significant in enhancing intein splicing or temperature sensitivity. These amino acid changes are dependent upon the specific intein, target enzyme, and intein insertion site.

Inserting the Tth intein into P77853, which does not contain an intein in its native sequence resulted in TSP switching phenotypes as described in the examples above. The P77853 T134 site is located at the junction of a beta-sheet and a loop region and the SVM score ranks this in the top 5 highest probability splice sites. Additionally, increased splicing occurs with a mutation near the insertion site to introduce a +2 proline, which correlates to a higher SVM score. Inserting the Tth intein in the P77853 S158 site, which is the 7$^{th}$ closest site to the active site residues (only 6.6 angstroms away) and also occurs at the junction of a beta-sheet loop region, resulted in intein-modified candidates that were capable of temperature dependent splicing and both switching and TSP phenotypes.

Examples of intein modified xylanses are provided in SEQ ID NOS: 1629-1712.

Example 6

Examples of Intein modified cellulases are provided in SEQ ID NOS: 1713-1784.

Example 7—Cellulase Assays and Purification

The cellulase Ace1 (endoglucanase E1 from *Acidothermus cellulolyticus* 11B) is an endoglucanase (EC 3.2.1.4) from *Acidothermus cellulolyticus* (Genbank accession P54583). The enzyme has an N-terminal catalytic domain (CD) with homology to members of the glycosyl hydrolase 5 family of enzymes and a C-terminal cellulose binding domain with homology to the carbohydrate binding module 2 (CBM2) family of proteins. The CD and CBM2 domains in P54583 are joined by a serine-, threonine-, and proline-rich linker domain. P54583 has been expressed from heterologous systems, including plants, and has been shown to effectively hydrolyze plant-derived cellulosic material.

Expression and Characterization of P54583.

Figure 5:
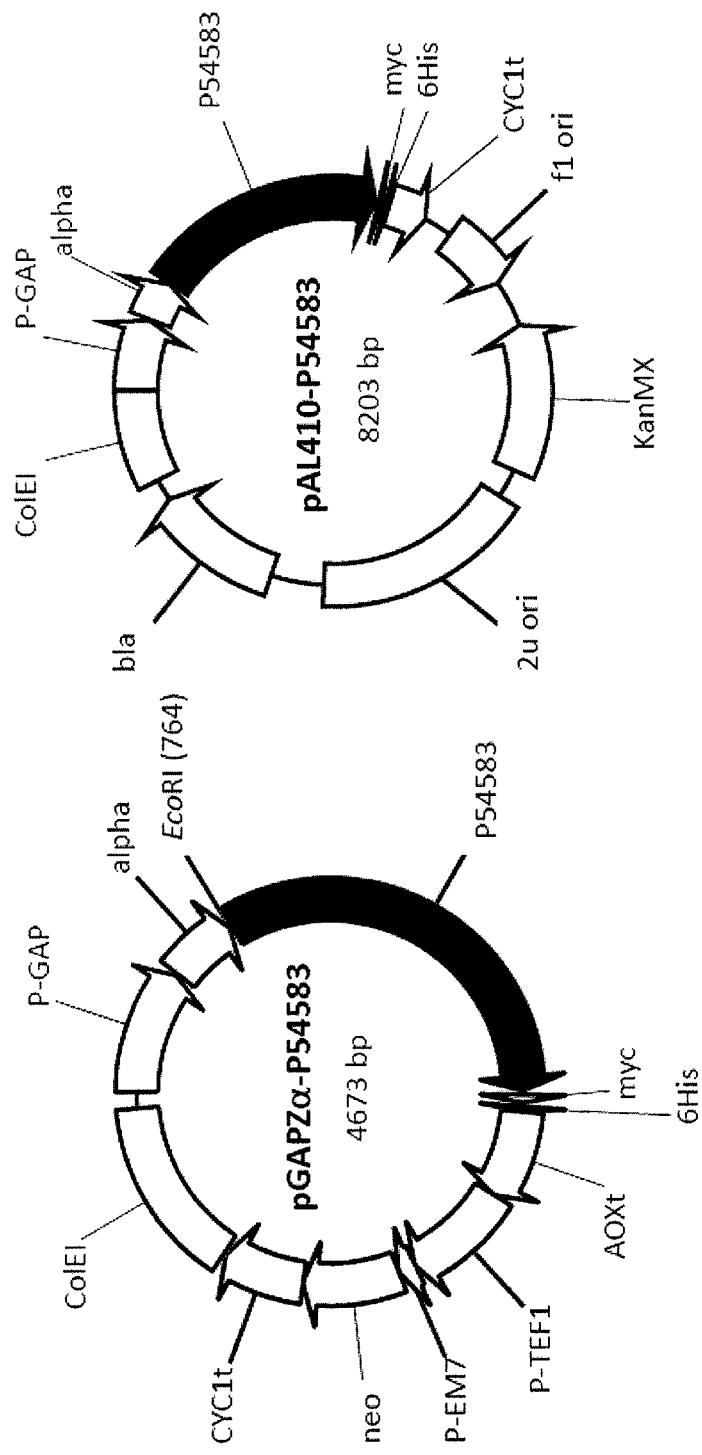
FIG. 5 illustrates plasmid vectors for expressing and secreting intein modified proteins; e.g., endoglucanases derived *Acidothermus cellulolyticus*, in yeast cells.

Referring to FIG. 5 plasmids pGAPZα and pAL410 are illustrated with cellulase inserts. The plasmids are not drawn to scale. In FIG. 5, the annotations have the following meaning: P-GAP, nominally constitutive yeast GAP promoter; alpha, secretion signal from yeast alpha mating factor, which is translated as an N-terminal fusion to the endoglucanase; P54583, coding sequence for Ace1 endoglucanase (see below); AOXt, transcriptional terminator and polyadenylation signal derived from the yeast AOX gene; P-TEF1, promoter from the yeast TEF1 gene; P-EM7, promoter derived from the yeast AM7 gene; zeo, coding sequence conferring zeocin resistance in yeast and *E. coli*; CYC1t, transcriptional terminator and polyadenylation signal derived from the yeast CYC1 gene; ColEI, region that enables replication of the plasmid in *E. coli*; f1 ori, sequence for generating single-stranded plasmid derivatives; KanMX, gene conferring resistance to G418 in yeast; 2u ori, 2 micron origin, enabling plasmid replication in yeast cells; bla, gene conferring ampicillin resistance in bacterial cells. Note that P54583 is expressed with C-terminal 6His and myc translational fusions from pGAPZα-P54583 and pAL410-P54583.

A codon-optimized version of P54583 was prepared. The DNA sequence of P54583 as optimized for expression in plants is shown below. Note: this sequence corresponds only to amino acid residues 42 through 562 of the native polypeptide in *A. cellulolyticus*, which corresponds to the "mature" form of the endoglucanase and lacks the signal peptide (amino acid residues 1 through 41).

Codon-Optimized Version of P54583

(SEQ ID NO: 1933)
ATGGCTGGAGGAGGATACTGGCACACTTCCGGCAGGGAGATCCTCGACGC

AAATAACGTTCCAGTCAGAATCGCCGGGATTAATTGGTTTGGCTTCGAAA

CGTGTAACTACGTGGTTCACGGCCTGTGGTCTCGGGATTACAGATCAATG

CTCGACCAGATCAAATCCTTGGGGTATAATACAATTAGGCTGCCCTACAG

CGATGACATTCTTAAGCCTGGAACCATGCCGAACTCGATTAATTTCTACC

AAATGAACCAGGATCTGCAGGGATTGACTTCTCTGCAGGTTATGGACAAG

ATCGTGGCGTACGCCGGCCAAATCGGGCTCAGAATTATTTTGGATCGGCA

-continued
CAGGCCAGACTGCTCAGGTCAGTCGGCCCTGTGGTACACAAGCTCCGTGT

CAGAGGCAACATGGATTTCAGATCTTCAAGCCCTCGCACAACGCTATAAA

GGCAACCCCACGGTTGTGGGATTCGACCTTCACAACGAACCTCACGATCC

GGCCTGTTGGGGCTGCGGGGACCCTTCGATCGACTGGAGACTGGCAGCGG

AGAGGGCTGGTAACGCCGTTCTCAGCGTCAATCCCAACTTGCTGATCTTT

GTGGAGGGAGTTCAGTCCTACAACGGCGATTCTTACTGGTGGGGCGGAAA

TCTCCAAGGCGCAGGGCAGTATCCTGTCGTGCTTAACGTTCCGAATCGCC

TGGTCTACTCAGCACACGACTACGCGACTAGCGTGTACCCACAGACGTGG

TTCTCCGATCCCACATTTCCTAACAATATGCCGGGAATCTGGAACAAGAA

TTGGGGTTACTTGTTTAACCAAAACATTGCTCCAGTTTGGTTGGGTGAAT

TTGGCACCACTCTTCAGTCGACGACAGACCAAACCTGGCTGAAAACCCTC

GTCCAGTATTTGCGGCCAACTGCTCAGTACGGAGCAGATTCTTTTCAATG

GACGTTCTGGTCTTGGAATCCTGACTCCGGGGATACAGGCGGTATCCTGA

AAGACGATTGGCAGACCGTGGACACTGTTAAGGACGGGTACTTGGCGCCG

ATTAAAAGCTCGATCTTTGACCCAGTCGGCGCTAGCGCTTCCCCATCTTC

ACAACCTTCGCCGAGCGTCAGCCCCAGCCCAAGCCCAAGCCCGTCTGCCA

GCAGAACCCCCACTCCCACACCTACCCCCACGGCCTCACCAACTCCGACG

CTCACTCCTACGGCGACGCCAACACCAACTGCTTCACCCACTCCTAGCCC

CACCGCAGCGAGCGGGGCTAGGTGCACCGCTTCTTACCAGGTCAACTCTG

ACTGGGGTAATGGCTTCACCGTGACTGTGGCGGTCACTAACTCAGGAAGC

GTCGCGACGAAAACCTGGACTGTGTCCTGGACGTTCGGGGGCAACCAAAC

AATCACCAACAGCTGGAACGCTGCAGTTACGCAGAATGGGCAAAGCGTCA

CGGCGCGCAATATGAGCTACAACAACGTGATTCAACCAGGCCAGAATACC

ACATTCGGTTTTCAAGCAAGCTATACCGGGTCAAACGCTGCCCCAACTGT

CGCTTGTGCTGCCTCAGCGGCCGCATATATAT.

A DNA fragment carrying this sequence was ligated into the *Pichia pastoris* integrative expression vector pGAPZαA (Invitrogen, Carlsbad Calif.), described above. pGAPZα is an integrative vector for transformation of *P. pastoris* GS115. The resulting plasmid, pGAPZα-P54583 (FIG. 5), was then introduced into *P. pastoris* GS115 cells according to the Invitrogen protocol. Recombinants were selected on the basis of zeocin resistance, and scored for their ability to mobilize the dye from AZCL-HE-cellulose (Megazyme International Ireland Ltd) on agar plates.

Figure 6:
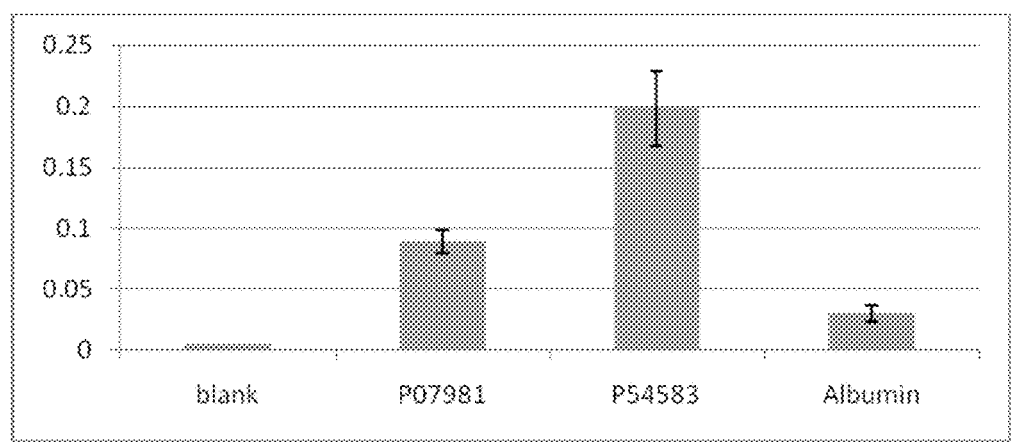
FIG. 6 illustrates activity assays of *Pichia* strains expressing either P07981 (endoglucanase EG-1 from *Trichoderma reesei*), P54583, or albumin (as a negative control).

*Pichia* strains expressing either P54583, an unrelated endoglucanase from *Trichoderma reesei* (P07981 from glycosyl hydrolase family 7), or albumin were grown in rich media in the presence of zeocin. Supernatants were collected from these cultures and assayed for endoglucanase activity using the Cellazyme C assay (see below), in which endoglucanases release blue dye (AZCL) from a cellulosic substrate (Megazyme International Ireland, Ltd.). These assays demonstrated that the *Pichia* clones expressing P54583 produced approximately twice as much endoglucanase activity as did the clones expressing P07981 See FIG. 6. In FIG. 6, Blank is a sample containing uninoculated culture medium, and activity is expressed in cellulase units.

Figure 7:
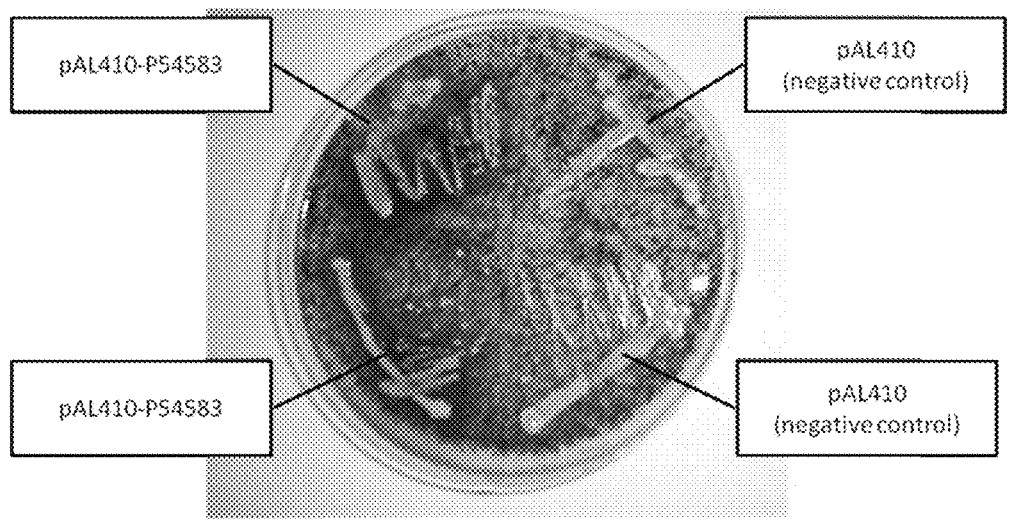
FIG. 7 illustrates a plate assay for secretion of P54583 from *S. cerevisiae*.

As mutagenesis might be more easily accomplished in *S. cerevisiae*, the coding sequence for P54583 was transferred from pGAPZα-P54583 to pAL410, producing the plasmid pAL410-P54583 (FIG. 5). pAL410 is an autonomously replicating vector for transformation of S. cerevisiae. S. cerevisiae strains carrying pAL410-P54583 plasmid or the negative control plasmid pAL410 were scored onto YPD agar plates containing 100 mg/L G418 and onto which an overlay of 0.2% AZCL-HE-cellulose (Megazyme) in 2% agar had been applied. Details of the plate activity assay are provided below. As shown in FIG. 7, two independent transformants carrying pAL410-P54583 and two carrying pAL410 were scored onto AZCL-HE-cellulose. Mobilization of the AZCL dye was clearly visible only in the vicinity of the clones that secreted active endoglucanase.

Measuring Activity of Endoglucanases and Intein-Modified Derivatives:

Plate Activity Assays.

Activity assay plates were prepared by applying a thin layer of liquid agar containing 0.2% AZCL-HE cellulose substrate over YPD G418 100 mg/L selection plates. Once the plates were solidified, yeast cells containing genes of interest were plated on top of the substrate overlay. Cells were then grown at 30° C. Active endocellulase will mobilize AZCL dye and a blue halo will form in the surrounding media. This is a qualitative assay to evaluate activity from different host strains and constructs over varying temperatures and time frames. This can also be tested to see activity in intein modified P54583 derivatives.

Liquid Phase Activity Assays.

The liquid assays allow for greater variation in assay and sample preparation conditions and give quantifiable results by absorbance readings on a spectrophotometer or plate reader. Assay conditions may vary for a wide range of pH, temperature, duration, and sample preparation. Sample preparation for this assay can include varied growth conditions, concentration or purification methods and pretreatments. This assay can be modified for measuring activity within the culture supernatants or cell pellets.

Cellazyme C Tablet (Megazyme) Substrate Liquid Assay.

Figure 8:
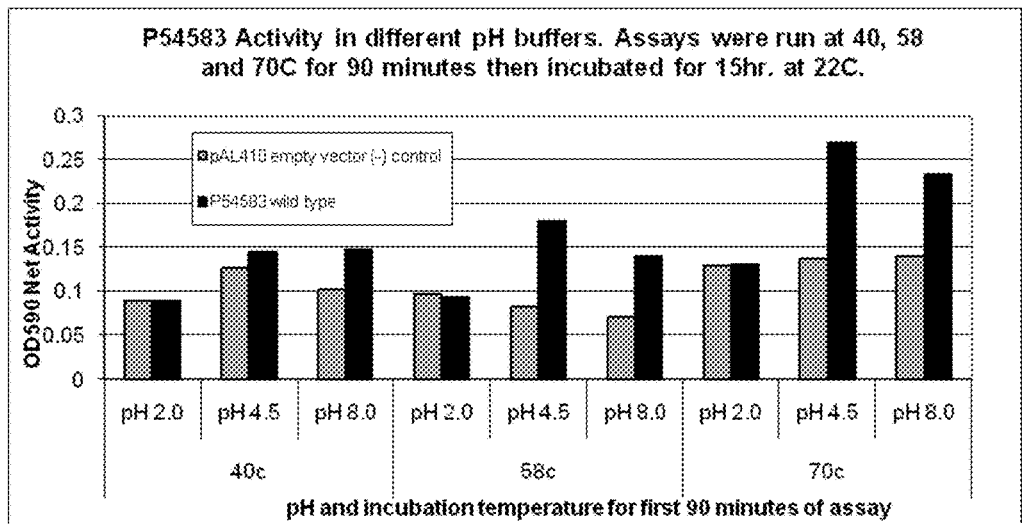
FIG. 8 illustrates P54583 activity from pH 4.5 to pH 8.0 at different temperatures.
Figure 9:
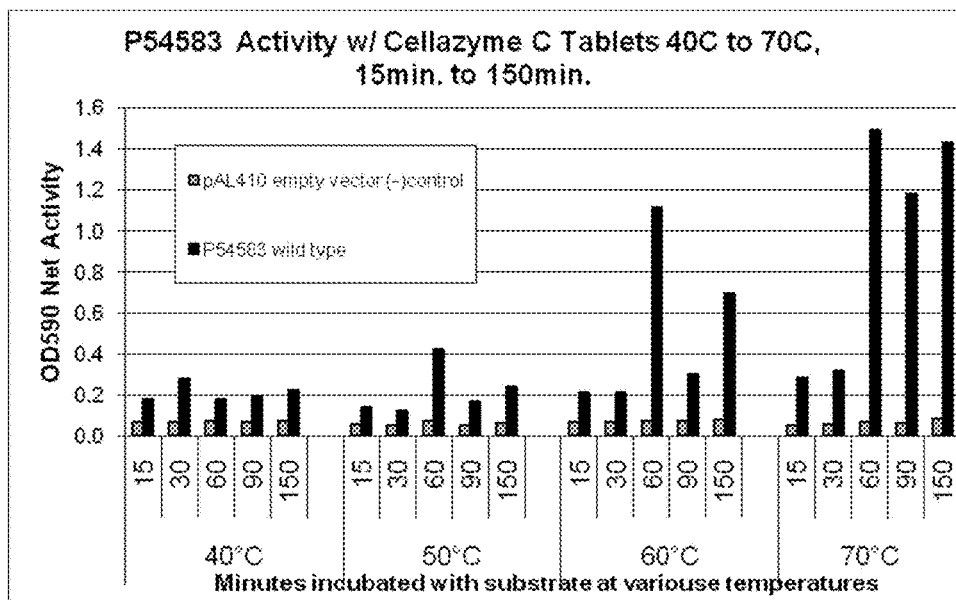
FIG. 9 illustrates P54583 activity over time and at different temperatures.

Cellazyme C tablets are pre-pelleted AZCL-HE cellulose substrate (Megazyme International Ireland, Ltd.). This assay gives results that correlate well with the plate assay. A standard Cellazyme C tablet assay is conducted as follows. Mix a protein sample from liquid culture with 25 mM NaOAc buffer pH4.5 to a final volume of 500 uL. Equilibrate samples to 42° C. for 5 minutes. Add 1 Cellazyme C tablet to each sample and incubate for 30 minutes at 42° C. To stop reaction, add 1 mL 20% tris base. Measure $Abs_{590}$ in clear flat bottom plate on plate reader. Samples with more endocellulase activity will degrade the substrate more rapidly causing the $Abs_{590}$ to increase. Using this assay, we determined that P54583 activity is optimal around pH 5.0 and increases up to at least 70° C. Longer duration of assay time will give increased absorbance (590 nm) readings (FIGS. 8 and 9). As shown in FIG. 8, P54583 has increased activity at pH 4.5 to pH 8.0. However there is no significant activity above that of the negative control at pH 2.0. As shown in FIG. 9, the Cellazyme C assay can be used to demonstrate that P54583 activity increases with increased temperature, and the signal intensity (absorbance 590) increases with time.

PNP-C Liquid Assay.

Figure 10:
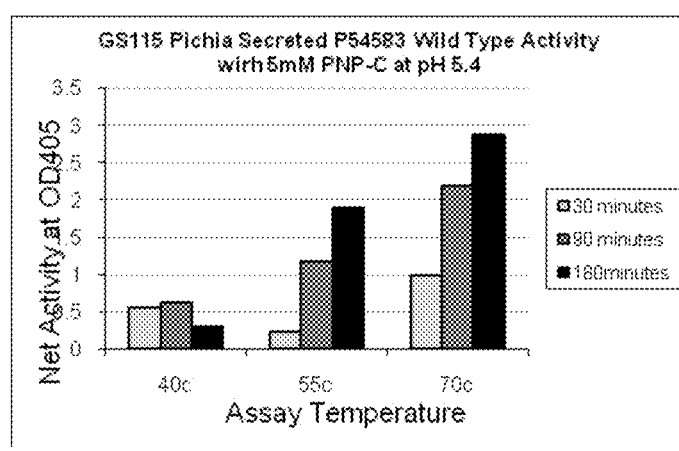
FIG. 10 illustrates a PNP-C assay for P54583.

Activity from endoglucanases such as P54583 is also detectable with para-nitrophenyl-cellobioside (PNP-C) substrates. A standard PNP-C assay is a 50 ul reaction including 5 mM PNP-C substrate, active enzyme and a buffer to control pH. This assay can be run over a wide range of pH, time, and temperature conditions. To stop the reaction and to amplify the signal intensity, 100 uL of sodium carbonate pH 10.5 is added at a given timepoint. Absorbance at 405 nm ($Abs._{405}$) is measured on a spectrophotometric plate reader. An increase in activity will give a greater reading (FIG. 10). As shown in FIG. 10, a PNP-C assay of P54583 shows that enzyme activity increases with assay temperature.

Enzchek (Invitrogen) Liquid Assay.

Enzchek is a synthetic, fluorometric substrate that is also useful for endoglucanase activity assays. A standard assay involving Enzchek substrate is as follows. Mix equal volumes of room temperature substrate with room temperature enzyme, buffered around pH 5.0, in black well plates (e.g., Corning 384-well black plates #3820) for fluorescence reading. Incubate at room temperature protected from light and measure fluorescence with 340/450 excitation/emission wavelengths. Fluorescence readings increase over time and with more concentrated samples. Readings can be taken without stopping the reaction as early as 5 minutes after the assay begins or after several hours of incubation for samples with low levels of activity. Stopping a reaction makes it possible to perform the reading after the same incubation time, which is useful when processing hundreds or thousands of samples. To stop a reaction, add an equal volume of 20% tris base. This causes an immediate increase in fluorescent reading, which appears consistent between all samples, and is stable for several hours. This activity assay is sensitive, reproducible and can be used for high throughput assays on a liquid handler. Standard liquid handler conditions may be set to 10 ul reactions using total culture, in Corning #3820 plates.

Selection of Yeast Host for Expressing Intein-Modified Endoglucanases.

To test whether alternative yeast hosts might be more suitable for i) mutagenesis and ii) screening clones expressing intein-modified endoglucanases, the abilities of two yeast strains (INVSc-1 (Invitrogen, Carlsbad Calif.) and SCBJ (a.k.a. BJ5465, American Type Culture Collection, Manassas Va., cat. No. 20829)) to take up foreign DNA were compared. Samples of plasmid DNA as either supercoiled or linearized DNA were prepared, and these DNAs were used to transform samples of each cell type with Zymo Research's EZ yeast transformation kit. Table 5, below, shows the relative transformation efficiency of two strains of S. cerevisiae. As shown, transformation efficiency was 100 fold higher with SCBJ than with INVSc1. SCBJ forms noticeable colonies sooner than do INVSc-1 cells.

TABLE 5

| Host | DNA | # of Colonies |
|---|---|---|
| SCBJ | 160 ng linear DNA | 5,000 |
| INVSc-1 | 160 ng linear DNA | 30 |
| SCBJ | Supercoiled plasmid | 7,000 |
| INVSc-1 | Supercoiled plasmid | 50 |

Pull Down Concentration and Purification of Endoglucanases Expressed from Yeasts.

Figure 11:
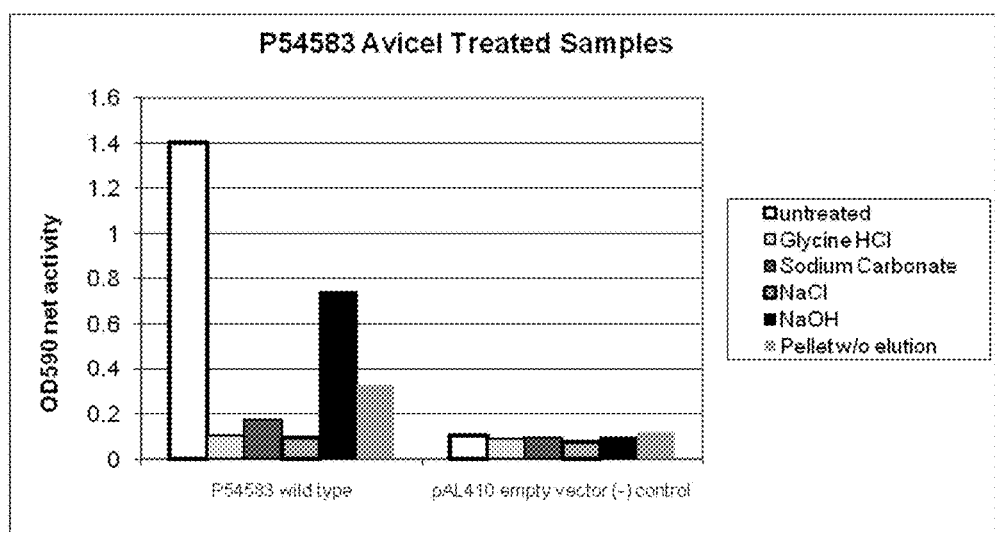
FIG. 11 illustrates purification of P54583 with microcrystalline cellulose.

Common among many endoglucanases, P54583 possesses a C-terminal carbohydrate binding domain that tethers the enzyme to its crystalline substrate. Based on this feature, methods to pull down, and partially purify, endoglucanase with a carbohydrate analog were tested. Six equal aliquots from supernatants of cultures either expressing P54583 or carrying the negative control empty vector (pAL410, FIG. 5) were collected. Avicel™ (microcrystalline cellulose) was added to five aliquots (all but one aliquot, which was saved as the untreated sample). Then, all aliquots were rocked at room temperature for one hour. After incubation, the avicel was pelleted and supernatant was discarded. Four pellets were washed with elution buffers, as indicated in FIG. 11. The eluate was immediately transferred to clean tubes and brought to a neutral pH. The fifth avicel pellet did not receive an elution wash. Activity of all six aliquots was then measured with Cellazyme C tablets. As shown in FIG. 11, microcrystalline cellulose can be used to separate active cellulase out of culture samples. This is a simple, inexpensive, and rapid method for protein purification and concentration of supernatants and cell lysates. Enzyme can then be analyzed by western blot analysis or activity assayed directly from the Avicel™ or eluted to a lesser extent with a variety of buffers.

Immunological Assays.

Figure 12:
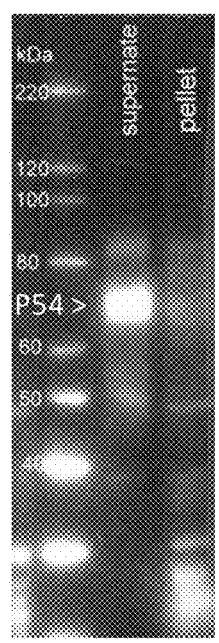
FIG. 12 illustrates western detection of wild type P54583.

P54583 can be detected directly via immunological assays such as western blots. FIG. 12 illustrates the results of a western blot. To conduct the assay, proteins were derived from either culture supernatants or lysates of cell pellets, then deglycosylated prior to electrophoresis. This assay shows that the majority of the detectable protein resides in the culture supernatant which suggests that an antibody-based affinity purification of the enzyme might be useful for protein concentration and purification.

Example 8—Intein Modification of P54583 Endoglucanase

Figure 13:
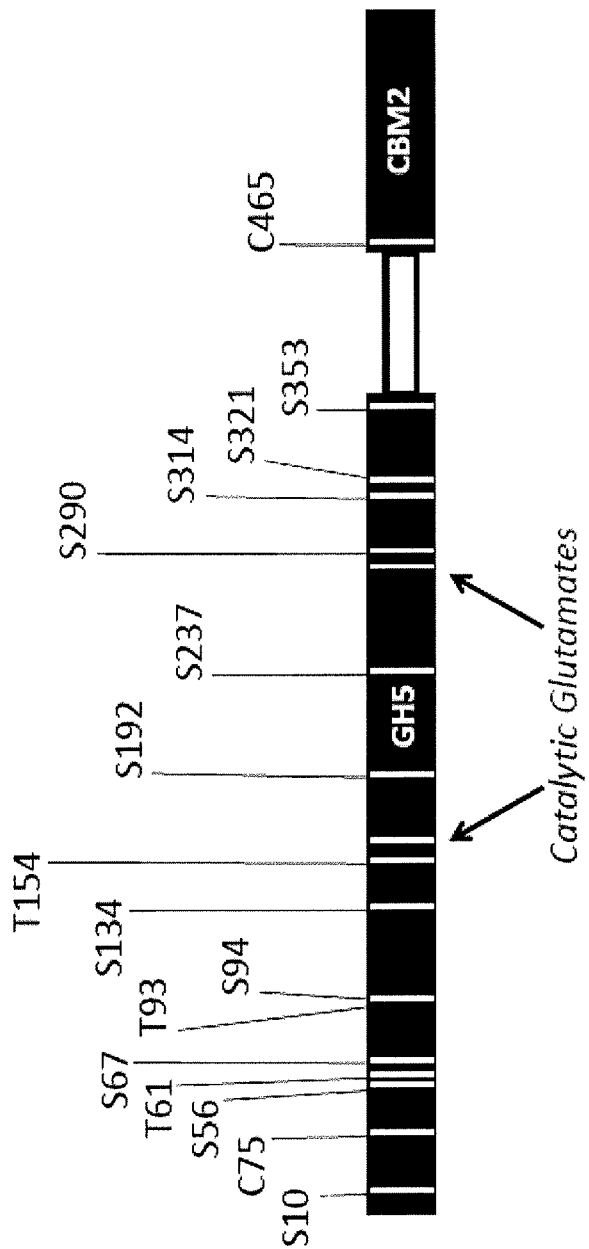
FIG. 13 illustrates candidate intein insertion sites in P54583.

P54583 intein insertion sites were identified by the method set forth in the detailed description. FIG. 13 depicts the relative positions of sites selected in P54583 for insertion of the Tth intein. Relative positions of the catalytic domain (GH5), the linker domain (narrow bar), and the carbohydrate binding module (CBM2) are shown. Two catalytic glutamates are conserved among members of the GH5 family. Numbering of the serine, threonine and cysteines residues shown are all relative to the "mature" form of the polypeptide as it would be secreted from S. cerevisiae following cleavage of the alpha signal peptide, except for C75 and C465, which are actually at position 35 and 425 relative to the cleavage site.

Figure 14:
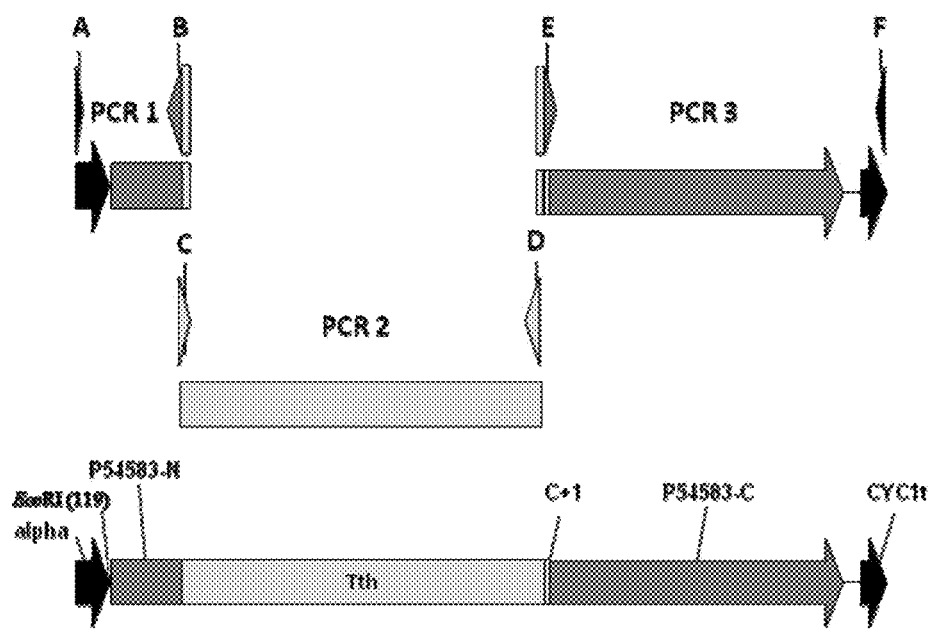
FIG. 14 illustrates an assembly strategy for genes encoding intein-modified endoglucanases.

Coding sequences for the recombinant P54583 proteins were then assembled via an SOE PCR strategy (Horton R M, Hunt H D, Ho S N, Pullen J K, Pease L R. 1989. Engineering hybrid genes without the use of restriction enzymes: gene splicing by overlap extension. Gene. 77(1):61-8), which is incorporated herein in its entirety as if fully set forth) as depicted in FIG. 14. This strategy is similar to that used above in assembling intein-modified xylanase genes. Primers were designed to anneal to:

(A) the sequence encoding the alpha signal peptide in pAL410-P54583 (see FIG. 5);
(B) a region within the coding sequence for P54583 that is adjacent to the insertion site;
(C) the 5' end of the coding sequence for the Tth intein;
(D) the 3' end of the coding sequence for the Tth intein;
(E) a region within the coding sequence for P54583 that is adjacent to the insertion site (note this site does not overlap that covered by primer C); and
(F) a region within the CYC terminator sequence from pAL410 P54583.

PCR1 employed primers A and B to assemble a short product that includes the coding sequences for a portion of the alpha signal factor as well as the N-terminal portion of the endoglucanase (P54583-N). The extreme 3' end of PCR product 1 includes a short segment that is homologous to the extreme 5' end of the Tth intein. PCR2 employs primers C and D to amplify the coding sequence of the Tth intein. PCR3 employs primers E and F to amplify the coding sequences for the C-terminal portion of the endoglucanase (P54583-C, which may include all or a portion of the catalytic domain as well as the carbohydrate binding module) along with the "C+1" amino acid, a short segment that is homologous to the extreme 5' end of the Tth intein, and a portion of the CYC1 terminator (CYC1t) from pAL410 P54583. PCR products 1, 2, and 3 were then combined in a single PCR reaction. By virtue of their homology to the ends of the Tth intein, PCR products 1 and 3 will anneal to PCR product 2. DNA synthesis and amplification with the outermost primers (A and F) will lead to the assembly of the full-length product, as indicated at the bottom of the diagram. The final product is often referred to simply as a "NIC" (N-terminal fragment, an Intein, and a C-terminal fragment). This method may be used to construct an intein modified protein of any type at any insertion site by choosing appropriate primers. And the intein insertion sited can be selected as any amino acid in the protein by utilizing a natural nucleophilic amino acid at the zero position or mutating the amino acid at the zero position to be a nucleophilic amino acid. The nucleophilic amino acid can be a C, T, or S residue.

Typical cycling conditions for SOE PCR involved 20 ul reactions, with 10 μl of Phusion HF (New England Biolabs, Ipswich Mass.) DNA polymerase Master Mix, 4 μl of each primer (from a stock concentration of 1 uM) and 2 μl of the appropriate template, diluted to approximately 0.1-1 ng/μl. Thermal cycling was carried out as recommended by the manufacturers of Phusion HF DNA polymerase. After the initial round of PCR reactions, products were gel purified via the Wizard SV Gel and PCR Cleanup Kit (Promega, Madison, Wis.), and 1 μl from each first round product was mixed to assemble the second round (full-length) product in a subsequent PCR reaction, with conditions virtually identical to the first round, except that extension times were increased from 30 s to as much as 60 s.

To prepare any desired intein-modified P54583 derivative, PCR products can be prepared that are tailored for each intein insertion position. However, some of the components in this experimental setup are modular. For example, primers C and D can be used to prepare PCR product 2, which can then be used to assemble any of the planned recombinants. Similarly, primers A and F can be used to prepare PCR products 1 and 3, respectively, regardless of the insertion position. As such, only primers B and E are unique to a given intein insertion event. Table 6, below, lists the sequences (in 5'-3' orientation) of the oligonucleotide primers that were used to assemble each of the intein-modified endoglucanases. While primers B and E are unique to each product, each contains a region that is homologous to the terminus of the Tth intein, as presented in the discussion of FIG. 14. This region is underlined in each primer sequence in Table 6.

TABLE 6

```
Primer A   GCTGTTTTGCCATTTTCCAACAGCA (SEQ ID NO: 1934)

Primer C   TGCCTGGCCGAGGGCTCGCTCGTCTTGGACGCGGCTACCG (SEQ ID NO: 1935)
```

TABLE 6 -continued

| | |
|---|---|
| Primer D | GTTATGCACCACCAGGTCCTCGCTCACGAAGTTTGCAAAG (SEQ ID NO: 1936) |
| Primer F | CCCAAAACCTTCTCAAGCAAGGT (SEQ ID NO: 1937) |

| Insertion Site | Primer B |
|---|---|
| S10 | AGCGAGCCCTCGGCCAGGCAAGTGTGCCAGTATCCTCCTC (SEQ ID NO: 1938) |
| S56 | AGCGAGCCCTCGGCCAGGCATTTGATCTGGTCGAGCATTG (SEQ ID NO: 1939) |
| C75 | TCGGGTACCCTCGGCAAGGCACGTTTCGAAGCCAAACCA (SEQ ID NO: 1940) |
| T61 | AGCGAGCCCTCGGCCAGGCAATTATACCCCAAGGATTTGA (SEQ ID NO: 1941) |
| S67 | AGCGAGCCCTCGGCCAGGCAGTAGGGCAGCCTAATTGTAT (SEQ ID NO: 1942) |
| T93 | AGCGAGCCCTCGGCCAGGCACAATCCCTGCAGATCCTGGT (SEQ ID NO: 1943) |
| S94 | AGCGAGCCCTCGGCCAGGCAAGTCAATCCCTGCAGATCCT (SEQ ID NO: 1944) |
| S134 | AGCGAGCCCTCGGCCAGGCACACGGAGCTTGTGTACCACA (SEQ ID NO: 1945) |
| T154 | AGCGAGCCCTCGGCCAGGCAGGGGTTGCCTTTATAGCGTT (SEQ ID NO: 1946) |
| S192 | AGCGAGCCCTCGGCCAGGCAGAGAACGGCGTTACCAGCCC (SEQ ID NO: 1947) |
| S237 | AGCGAGCCCTCGGCCAGGCAGTAGACCAGGCGATTCGGAA (SEQ ID NO: 1948) |
| S290 | AGCGAGCCCTCGGCCAGGCACTGAAGAGTGGTGCCAAATT (SEQ ID NO: 1949) |
| S314 | AGCGAGCCCTCGGCCAGGCAATCTGCTCCGTACTGAGCAG (SEQ ID NO: 1950) |
| S321 | AGCGAGCCCTCGGCCAGGCACCAGAACGTCCATTGAAAAG (SEQ ID NO: 1951) |
| S353 | AGCGAGCCCTCGGCCAGGCATTTAATCGGCGCCAAGTACC (SEQ ID NO: 1952) |

| Insertion Site | Primer E |
|---|---|
| S10 | AGGACCTGGTGGTGCATAACTCCGGCAGGGAGATCCTCGA (SEQ ID NO: 1953) |
| S56 | AGGACCTGGTGGTGCATAACTCCTTGGGGTATAATACAAT (SEQ ID NO: 1954) |
| C75 | AGGGGTTGTCGTGCACAACTGTAACTACGTGGTTCACGGCCT (SEQ ID NO: 1955) |
| T61 | AGGACCTGGTGGTGCATAACACAATTAGGCTGCCCTACAG (SEQ ID NO: 1956) |
| S67 | AGGACCTGGTGGTGCATAACAGCGATGACATTCTTAAGCC (SEQ ID NO: 1957) |
| T93 | AGGACCTGGTGGTGCATAACACTTCTCTGCAGGTTATGGA (SEQ ID NO: 1958) |
| S94 | AGGACCTGGTGGTGCATAACTCTCTGCAGGTTATGGACAA (SEQ ID NO: 1959) |
| S134 | AGGACCTGGTGGTGCATAACTCAGAGGCAACATGGATTTC (SEQ ID NO: 1960) |
| T154 | AGGACCTGGTGGTGCATAACACGGTTGTGGGATTCGACCT (SEQ ID NO: 1961) |
| S192 | AGGACCTGGTGGTGCATAACAGCGTCAATCCCAACTTGCT (SEQ ID NO: 1962) |
| S237 | AGGACCTGGTGGTGCATAACTCAGCACACGACTACGCGAC (SEQ ID NO: 1963) |
| S290 | AGGACCTGGTGGTGCATAACTCGACGACAGACCAAACCTG (SEQ ID NO: 1964) |
| S314 | AGGACCTGGTGGTGCATAACTCTTTTCAATGGACGTTCTG (SEQ ID NO: 1965) |
| S321 | AGGACCTGGTGGTGCATAACTCTTGGAATCCTGACTCCGG (SEQ ID NO: 1966) |
| S353 | AGGACCTGGTGGTGCATAACAGCTCGATCTTTGACCCAGT (SEQ ID NO: 1967) |

Insertion of the Tth intein into the C75 position was accompanied by a small number of conservative amino acid changes near the intein/extein junctions. To accommodate these changes, the Tth intein (PCR2) that was used to assemble the C75Tth product was amplified with alternative forms of primers C and D as follows:

C<sub>C75Tth</sub>,
(SEQ ID NO: 1968)
5' TGCCTTGCCGAGGGTACCCGAGTCTTGGACGCGGCTACCGGGCA 3'

D<sub>C75Tth</sub>,
(SEQ ID NO: 1969)
5' GTTGTGCACGACAACCCCTTCGCTCACGAAGTTTGCAAAGGGT 3'

The insertion sites listed in Table 2 are the same as those depicted in FIG. 13. A series of primers were also designed to insert the PspPol and RecA inteins into several positions within P54583. The strategy for inserting these inteins is identical to that described in reference to FIG. 14, except that the sequences of Primers B, C, D, and E are all tailored to the specific intein. The compositions of these primers are shown in Table 7 (primers used to assemble products encoding PspPol intein-modified P54583 endoglucanases) and Table 8 (primers used to assemble products encoding RecA intein-modified P54583 endoglucanases) below.

TABLE 7

| | |
|---|---|
| Primer A | GCTGTTTTGCCATTTTCCAACAGCA (SEQ ID NO: 1970) |
| Primer C | AGCATTTTACCGGAAGAATGGGT (SEQ ID NO: 1971) |
| Primer D | ATTATGTGCATAGAGGAATCCA (SEQ ID NO: 1972) |
| Primer F | CCCAAAACCTTCTCAAGCAAGGT (SEQ ID NO: 1973) |

| Insertion Site | Primer B |
|---|---|
| C75 | ACCCATTCTTCCGGTAAAATGCTCGTTTCGAAGCCAAACCA (SEQ ID NO: 1974) |
| S56 | ACCCATTCTTCCGGTAAAATGCTTTTGATCTGGTCGAGCATTGA (SEQ ID NO: 1975) |
| S94 | ACCCATTCTTCCGGTAAAATGCTAGTCAATCCCTGCAGATCCT (SEQ ID NO: 1976) |
| S237 | ACCCATTCTTCCGGTAAAATGCTGTAGACCAGGCGATTCGGA (SEQ ID NO: 1977) |
| S290 | ACCCATTCTTCCGGTAAAATGCTCTGAAGAGTGGTGCCAAATTCA (SEQ ID NO: 1978) |
| S353 | ACCCATTCTTCCGGTAAAATGCTTTTAATCGGCGCCAAGTACCCGT (SEQ ID NO: 1979) |
| C465 | ACCCATTCTTCCGGTAAAATGCTCCTAGCCCCGCTCGCTGCGGT (SEQ ID NO: 1980) |

| Insertion Site | Primer E |
|---|---|
| C75 | TGGATTCCTCTATGCACATAATTGTAACTACGTGGTTCACGGCCT (SEQ ID NO: 1981) |
| S56 | ACCCATTCTTCCGGTAAAATGCTTTTGATCTGGTCGAGCATTGA (SEQ ID NO: 1975) |
| S94 | TGGATTCCTCTATGCACATAATTCTCTGCAGGTTATGGACAAGATCGT (SEQ ID NO: 1983) |
| S237 | TGGATTCCTCTATGCACATAATTCAGCACACGACTACGCGA (SEQ ID NO: 1984) |
| S290 | TGGATTCCTCTATGCACATAATTCGACGACAGACCAAACCT (SEQ ID NO: 1985) |
| S353 | TGGATTCCTCTATGCACATAATAGCTCGATCTTTGACCCAGT (SEQ ID NO: 1986) |
| C465 | TGGATTCCTCTATGCACATAATTGCACCGCTTCTTACCAGGT (SEQ ID NO: 1987) |

TABLE 8

| | |
|---|---|
| Primer A | GCTGTTTTGCCATTTTCCAACAGCA (SEQ ID NO: 1988) |
| Primer C | TGCCTTGCCGAGGGTACCCGAaTCTTCGA (SEQ ID NO: 1989) |
| Primer D | GTTGTGCACGACAACCCCTTCGGCGA (SEQ ID NO: 1990) |
| Primer F | CCCAAAACCTTCTCAAGCAAGGT (SEQ ID NO: 1991) |

| Insertion Site | Primer B |
|---|---|
| C75 | TCGGGTACCCTCGGCAAGGCACGTTTCGAAGCCAAACCA (SEQ ID NO: 1992) |
| S56 | TCGGGTACCCTCGGCAAGGCATTTCATCTGGTCGAGCATTGA (SEQ ID NO: 1993) |

TABLE 8 -continued

| Site | Primer | Sequence |
|---|---|---|
| S94 | | TCGGGTACCCTCGGCAAGGCAAGTCAATCCCTGCAGATCCT (SEQ ID NO: 1994) |
| S237 | | TCGGGTACCCTCGGCAAGGCAGTAGACCAGGCGATTCGGA (SEQ ID NO: 1995) |
| S290 | | TCGGGTACCCTCGGCAAGGCACTGAAGAGTGGTGCCAAATTCA (SEQ ID NO: 1996) |
| S353 | | TCGGGTACCCTCGGCAAGGCATTTAATCGGCGCCAAGTACCCGT (SEQ ID NO: 1997) |
| C465 | | TCGGGTACCCTCGGCAAGGCACCTAGCCCCGCTCGCTGCGGT (SEQ ID NO: 1998) |

| Insertion Site | Primer E | |
|---|---|---|
| C75 | | AGGGGTTGTCGTGCACAACTGTAACTACGTGGTTCACGGCCT (SEQ ID NO: 1999) |
| S56 | | AGGGGTTGTCGTGCACAACTCCTTGGGGTATAATACAATTAGGCT (SEQ ID NO: 2000) |
| S94 | | AGGGGTTGTCGTGCACAACTCTCTGCAGGTTATGGACAAGATCGT (SEQ ID NO: 2001) |
| S237 | | AGGGGTTGTCGTGCACAACTCAGCACACGACTACGCGA (SEQ ID NO: 2002) |
| S290 | | AGGGGTTGTCGTGCACAACTCGACGACAGACCAAACCT (SEQ ID NO: 2003) |
| S353 | | AGGGGTTGTCGTGCACAACAGCTCGATCTTTGACCCAGT (SEQ ID NO: 2004) |
| C465 | | AGGGGTTGTCGTGCACAACTGCACCGCTTTCTTACCAGGT (SEQ ID NO: 2005) |

Using the above primers, SOE PCR reactions were carried out for all of the intein-modified endoglucanases that were designed. Full-length PCR products were then ligated into pCRBlunt II TOPO (Invitrogen) and individual clones were fully sequenced to ensure that no unintended base changes had occurred during PCR and/or cloning. In cases where mutations were discovered, all or parts of the affected PCR reactions were repeated and errors were corrected. Once the composition of a product encoding an intein modified P54583 was confirmed, the entire fragment was excised from the pCRBlunt II vector and ligated into pAL410 (or a related vector). The resulting vectors were subsequently introduced into yeast cells. Yeast transformants were typically verified via a combination of colony PCR and plasmid recovery via miniprep (using reagents from the ZymoPrep Yeast Miniprep Kit II, Zymo Research, Orange Calif.). Plasmids recovered from yeast cells were then re-introduced into E. coli cells, propagated, isolated via E. coli plasmid miniprep and examined via restriction enzyme digestion to determine whether the plasmids had suffered any mutations or rearrangement since their introduction into the original yeast cells. When fully verified plasmids were recovered in this manner, the corresponding yeast strain would be used in subsequent experiments involving the intein-modified endoglucanase.

Figure 15:
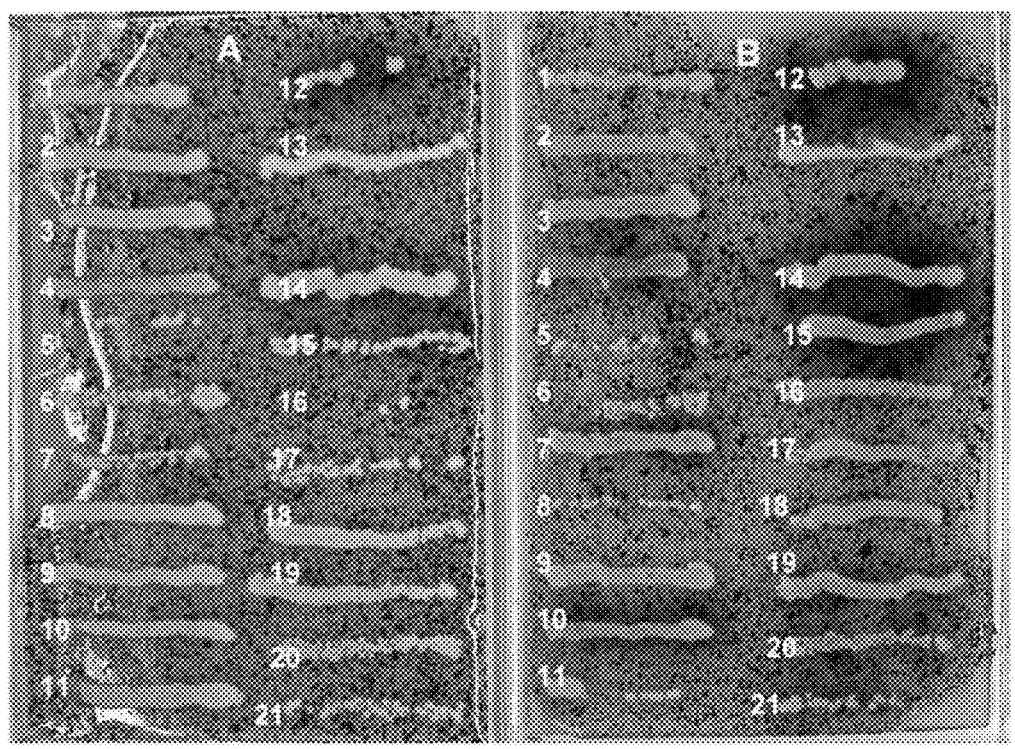
FIG. 15 illustrates scoring of intein-modified endoglucanases behavior in response to different temperature treatments.

S. cerevisiae transformants carrying expression vectors for intein modified endoglucanases were then scored onto parallel YPD plates (A and B) containing 100 mg/L G418 onto which an overlay of 0.2% AZCL-HE-cellulose had been applied. These plates were incubated for 2 nights at 30° C. Then plate B was moved to 70° C. for several hours. FIG. 15 shows plates A and B and in respective order, streaks 1-21 are P54583 T154Tth, P54583 S135Tth, P54583 S134Tth, P54583 S96Tth, P54583 S94Tth, P54583 T93Tth, P54583 C75Tth, P54583 S67Tth, P54583 T61Tth, P54583 S56Tth, P54583 S10Tth, P54583-Wild Type, pAL410 empty vector, P54583 S393Tth, P54583 S353Tth, P54583 S330Tth, P54583 S321Tth, P54583 S314Tth, P54583 S277Tth, P54583 S237Tth, and P54583 S192, which have the sequences of SEQ ID NOS: 1753-1758, 1741, 1759, 1760, 1739, 1761, 111, 2006, 1762-1767, 1743 and 1742, respectively. Blue halos appear around some of the cells, indicating the presence of P54583 activity. Results from this experiment suggested that insertion of the Tth intein disrupts P54583 to varying degrees, depending on the insertion site, and that one or more of these intein-modified endoglucanases displays temperature-sensitive enzyme activity.

Figure 16:
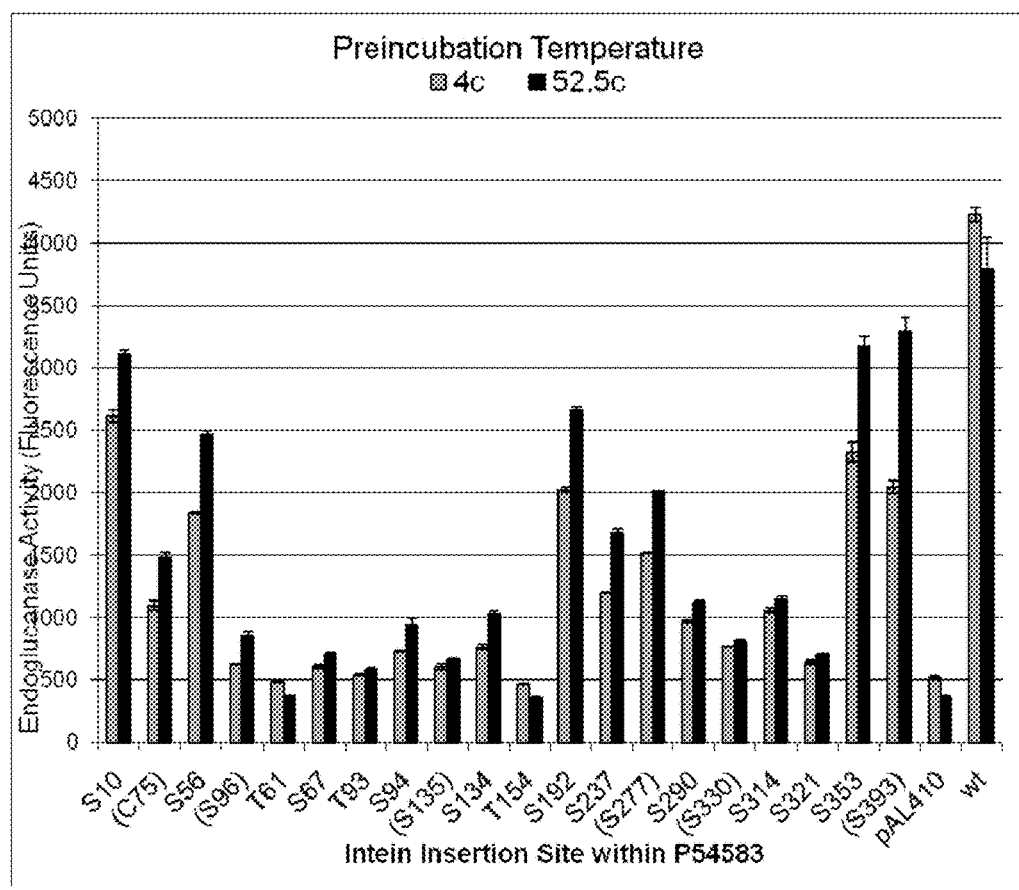
FIG. 16 illustrates intein modified endoglucanases activity assays.

Inserting Tth intein into P54583 wild type has an effect on the enzyme expression and activity levels, which can be measured by western analysis and activity assays. An Enzchek activity assay was run on 20 P54583 NICs with controls. The 20 NICS had the Tth intein inserted in the S10, S56, T61, S67, (C75), T93, S94, (S96), 5134, (S135), T154, 5192, 5237, 5290, 5314, 5321, 5353, and (S393) positions. These 20 NICS have the sequence of (SEQ ID NOS: 1761, 1739, 1760, 1759, 1741, 1758, 1757, 1756, 1755, 1754, 1753, 1742, 1743, 1768, 1766, 1765, 1763, and 1762). Culture supernatant was divided into aliquots. Half of these aliquots were subjected to heating pretreatment at 52.5° C. for 6 hours while the other half were stored at 4° C. Temperature and duration of pretreatment may vary. These samples were then equilibrated to room temperature and subjected to an Enzchek assay (3 hour incubation time with the substrate). At the end of the assay, endoglucanase activity was inferred from the amount of fluorescence in each sample. As shown in FIG. 16, the Enzchek activity assay revealed that a subset of the intein-modified endoglucanases produce enzyme activity above the background (pAL410, empty vector control), and that a portion of these show higher activity still when pre-incubated at 52.5° C. In FIG. 16, wt means wild type P54583 endoglucanase. Because of the difference in numbering used among constructs (reflecting either the immature or the mature form of P54583 lacking its signal peptide) the amino acid position of the insertion site relative to the immature form is presented in parentheses for a subset of the NICs.

Figure 17:
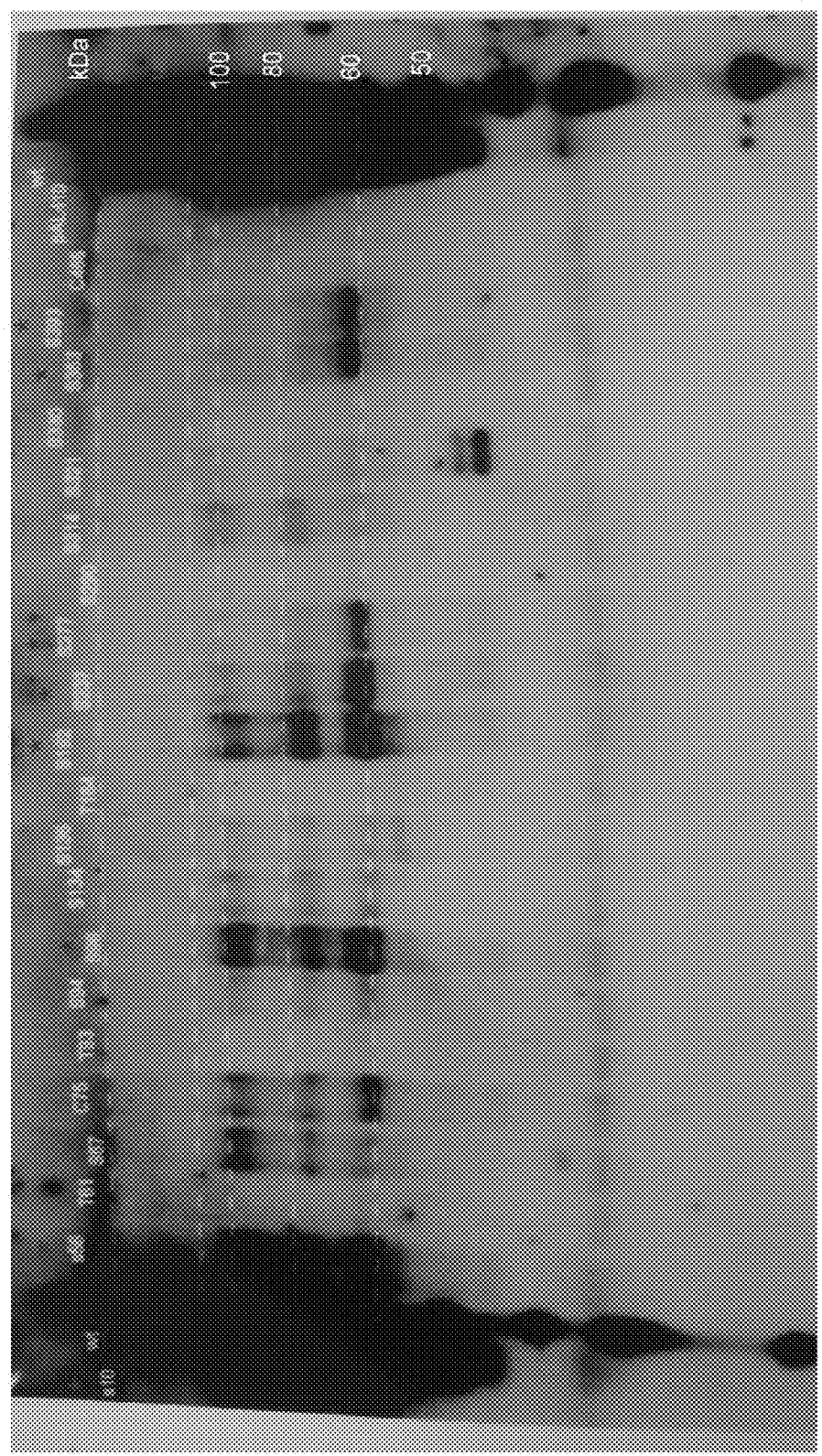
FIG. 17 illustrates a western blot analysis of various intein modified P54583 proteins.

The constructs described in FIG. 16 contain a His tag on the carboxyl end which can be detected by a His tag antibody. Supernatants from corresponding cultures were concentrated 20-fold, and used in western blot assays (FIG. 17). In FIG. 17, wt indicates the P54583 wild type, pAL410 indicates the empty vector with the His antibody (Genscript, Piscataway N.J.), and mature spliced protein appears as a 60 kDa band. An additional Tth intein modified P54583, C465 (SEQ ID NO: 1769) was also assayed by western blot, as shown in FIG. 17. Lanes marked with an asterisk also show significant activity on plate assay (See FIG. 15). Western blots showed that proteins with molecular weights similar to that of the wild type enzyme could be detected in cultures expressing intein-modified enzymes, suggesting that intein splicing is occurring in the recombinant proteins. Higher molecular weight species could also be detected in several samples, which may correspond to unspliced NICs, splicing intermediates, aggregates, or other forms of the recombinant proteins. The NICs showed varying levels of protein accumulation, which corresponds to the activity measurements presented in FIG. 16 to some extent.

Example 9—Mutagenesis of Intein Modified Endoglucanases

Homologous recombination has been used to generate tremendous diversity among DNA libraries in *S. cerevisiae* (Swers J S, Kellogg B A, Wittrup K D. 2004, Shuffled antibody libraries created by in vivo homologous recombination and yeast surface display, Nucleic Acids Res. 32:e36, which is incorporated by reference herein in its entirety as if fully set forth). In this system, linear DNAs carrying the coding sequences for polypeptides that have been generated can be inserted into linearized expression vectors by co-transformation into yeast. Error-prone PCR or other strategies can be used to mutagenize all of an intein-modified endonuclease or portions thereof (e.g., the intein). The resulting products can be co-transformed into *S. cerevisiae* cells along with a suitable linearized expression vector (e.g., pAL410 or a derivative thereof), which will catalyze homologous recombination between the molecules and give rise to collections of several thousand yeast clones, each carrying a unique recombinant expression vector. Yeast colonies that arise from such an in vivo recombination protocol can thus express a variety of modified proteins whose diversity is directly related to (or even greater than) the level to which the coding sequence has been mutagenized.

A series of recombination vectors for use in yeast in vivo recombination were developed. The recombination vectors each carry a truncated version of the Tth intein. The truncated Tth inteins lack most of the intein sequence, retaining only 70-80 bp from each of the 5' and 3' ends of the intein coding sequence. At the center of this DNA sequence is a unique EcoRV recognition site. The DNA sequence of the truncated Tth is shown below, with the EcoRV site underlined.

```
                                        (SEQ ID NO: 2007)
TGCCTGGCCGAGGGCTCGCTCGTCTTGGACGCGGCTACCGGGCAGAGGGT

CCCTATCGAAAAGGTGCGTCCGGGGATATCGAACCGGCCGGTAAGGCGAG

AACATTCGACTTGCGCGTTCCACCCTTTGCAAACTTCGTGAGCGAGGACC

TGGTGGTGCATAAC
```

Expression vectors that carry such a truncated intein can be easily linearized via EcoRV digestion. Since such vectors lack most of the "wild type" intein sequence, the expression vectors that arise during homologous recombination in yeast are more likely to carry the mutations generated during error-prone PCR since there is less "wild type" intein to compete with the mutants during recombination. Furthermore, the use of this truncated intein in the recombination vector provides the added benefit of decreasing the number of false positive that might arise due to vector self-ligation in a high throughput screening regime. Because of the nature of the truncation, the truncated inteins introduce a frameshift into the endoglucanase gene, resulting in an enzyme whose translation would be prematurely terminated. Such translation products are less likely to be enzymatically active. As such, functional enzymes that arise during screening of libraries are more likely to result from true recombination events involving DNA fragments encoding mutagenized inteins.

Figure 18A:
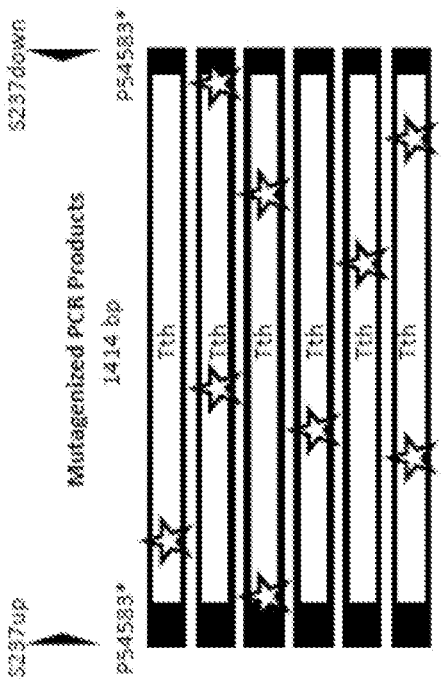
FIGS. 18A-C illustrate error prone PCT to generate mutangenized libraries.
Figure 18B:
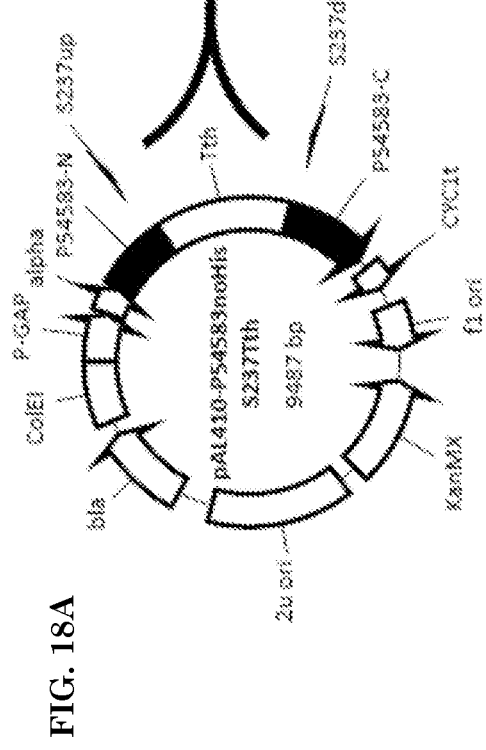
Figure 18C:
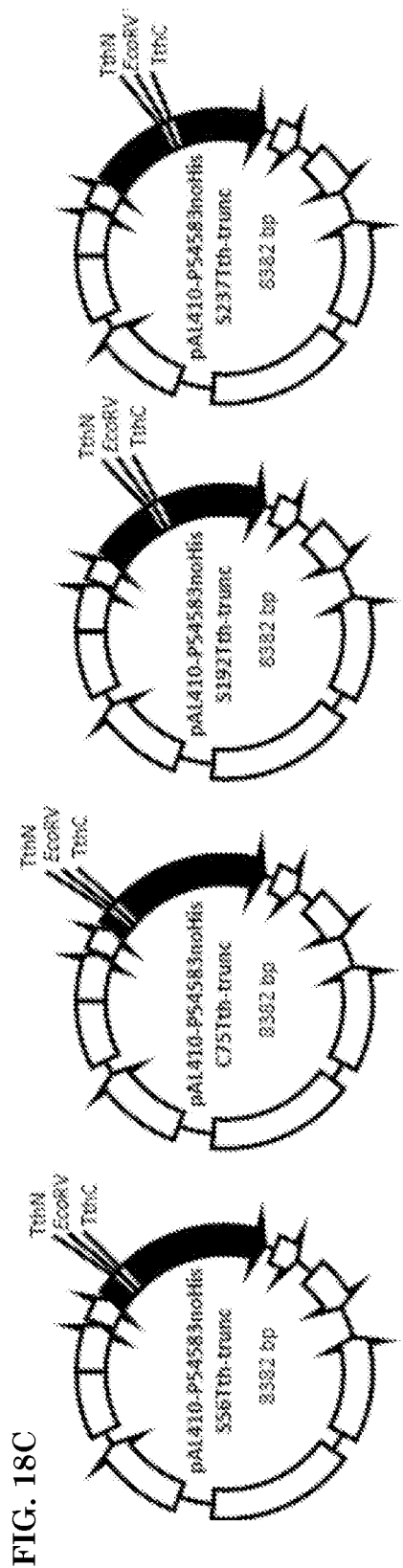

Using a strategy similar to that described in reference to FIG. 14, expression vectors derived from pAL410-P54583noHis were prepared. In these expression vectors, the truncated Tth intein sequence was introduced in place of the full-length inteins in either the S56, C75, S192, or S237 positions. This collection of recombination vectors was then used to generate libraries of mutagenized intein-modified endoglucanases in yeast SCBJ cells. Referring to FIGS. 18A-C, a PCR intein mutagenesis scheme is illustrated. Primers (e.g., S237up and S237down) flanking the intein insertion site in the template expression vector (pAL410-P54583noHis S237Tth (FIG. 18A)) can be used to amplify a specific region of the recombinant vector that contains the entire intein coding sequence as well as portions of the flanking extein coding sequences. Alternatively, primers that amplify only intein sequences can be used. Under appropriate conditions, PCR products were generated with random mutations scattered among the collection of amplified DNA molecules (stars). These mutagenized DNA molecules can be mixed with an appropriate vector, as shown in FIG. 18C that has been linearized via digestion with EcoRV restriction endonuclease. The mixture can then be introduced into yeast cells to drive recombination. In the example above, the DNA molecules depicted in (B) would be used to create a library of mutagenized inteins in the S237 position using linearized pAL410-P54583noHis S237Tth-trunc as the vector. Primers tailored for the S56, C75, or S192 positions can similarly be used in conjunction with the respective recombination vectors depicted in FIG. 18C. Such a strategy permits the inclusion of DNA molecules that carry mutations in the flanking regions of the extein (in this example, a endoglucanase) as well as within the intein. However, if PCR primers are used that amplify only intein sequences during error prone-PCR, then any of the recombination vectors can be used to host the altered intein coding sequences. In FIG. 18A, P54583-N and P54583-C refer to the coding sequences for the N and C-terminal portions of the endoglucanase. In FIG. 18B, P54583* refers to small flanking portions derived from the endoglucanase coding sequences that can be included in the mutagenized PCR product with judiciously designed primers. In FIG. 18C, TthN and TthC denote the N- and C-terminal portions of the Tth coding sequence that are separated by the EcoRV site in the truncated intein. Other abbreviations are as described in reference to FIG. 5.

Example 10—P54583 Modified with Mini-Inteins

Based on initial plate and liquid activity assays a subset of the insertion sites described above were chosen to modify with an additional eight mini Tth inteins, which are mTth001 (SEQ ID NO:92), mTTh002 (SEQ ID NO:93), mTth003 (SEQ ID NO:94), mTth004 (SEQ ID NO:95), mTth005 (SEQ ID NO:96), mTth007 (SEQ ID NO:98), mTth008 (SEQ ID NO:99), and mTth010 (SEQ ID NO:101). One intein was inserted per construct. The S56 position in P54583 was the initial site chosen for modification with mini-inteins. In a single yeast in vivo recombination reaction, the mini-Tth inteins were inserted into this position. Following recovery and growth of the yeast on YPD G418 plates, 36 separate colonies were cultured for activity assay. Two of the 36 expressed activity above baseline levels. Plasmids were recovered from these two strains and subjected to DNA sequence analysis. Both samples were found to carry the mTth010 mini-intein. The DNA sequence of the MTth010 mini-intein is shown below with the corresponding amino acid sequence beneath:

```
                       mTth010
tgcctggccgagggctcgctcgtcttggacgcggctaccgggcagagggt
  C  L  A  E  G  S  L  V  L  D  A  A  T  G  Q  R  V ccctatcgaaaaggtgcgtccggggatggaagttttctccttgggacctg
  P  I  E  K  V  R  P  G  M  E  V  F  S  L  G  P attacagactgtatcgggtgcccgttttggaggtccttgagagcgggtt
  D  Y  R  L  Y  R  V  P  V  L  E  V  L  E  S  G  V agggaagttgtgcgcctcagaactcggtcagggagaacgctggtgttgac
  R  E  V  V  R  L  R  T  R  S  G  R  T  L  V  L  T accagatcaccgcttttgaccccgaaggttggaaacctctttgtgacc
  P  D  H  P  L  L  T  P  E  G  W  K  P  L  C  D tcccgcttggaactccaattgcagtcagagatgttgagactggagaggtt
  L  P  L  G  T  P  I  A  V  R  D  V  E  T  G  E  V ctctgggaccctattgttgctgtcgaaccggccggtaaggcgagaacatt
  L  W  D  P  I  V  A  V  E  P  A  G  K  A  R  T  F cgacttgcgcgttccacccttttgcaaacttcgtgagcgaggacctggtgg
  D  L  R  V  P  P  F  A  N  F  V  S  E  D  L  V
tgcataac (SEQ ID NO: 2008)
V  H  N (SEQ ID NO: 101)
```

Figure 19:
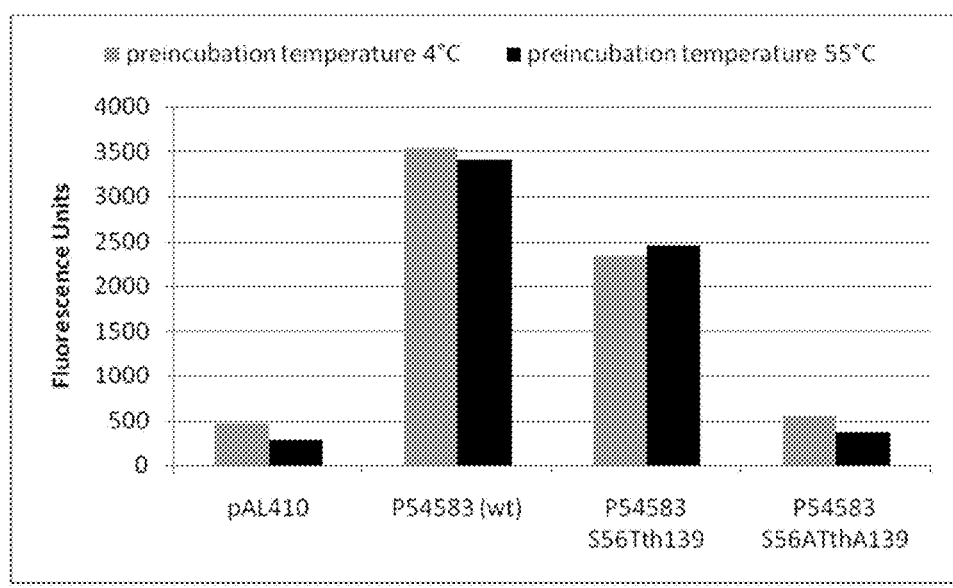
FIG. 19 illustrates the effect of a crippled intein on enzyme activity in P54583.

To test whether the endoglucanase activity of the P54583 derivative carrying this mini-intein (a.k.a. "P54583 S56mTth010") was dependent upon the ability of the mini-intein to splice, a modified version of the construct was prepared. In the modified version, the terminal amino acids of the intein (the cysteine residue at the N-terminus and the asparagine residue at the C-terminus; see the sequence above) were replaced with alanines. The N-terminal cysteine and the C-terminal asparagine likely play critical roles in catalyzing intein splicing, and substitutions of these residues with alanine are either known to or are likely to prevent intein splicing. Referring to FIG. 19, samples were removed from SCBJ yeast cultures carrying either the empty expression vector, pAL410 (negative control), an expression vector encoding the uninterrupted enzyme (P54583 wt), an expression vector encoding a derivative carrying the mini-intein in the S56 position (P54583 S56Tth139), or an expression vector encoding a derivative carrying the crippled mini-intein in the S56 position (P54583 S56MTth010). The samples were assayed for endoglucanase activity via a four hour incubation at room temperature in the Enzchek assay. Unlike the mini-intein, the crippled intein reduces endoglucanase activity nearly to the level of the negative control. This trend was consistent regardless of whether the samples had been pre-incubated at low (4° C.) or high (55° C.) temperatures for 6 hours prior to the assay. From this, it was concluded that the inability to splice a mini-intein in the S56 position of P54583 will disrupt enzyme activity, while a splicing-competent mini-intein in the same position will permit reconstitution of much of the enzyme's native activity.

Figure 20:
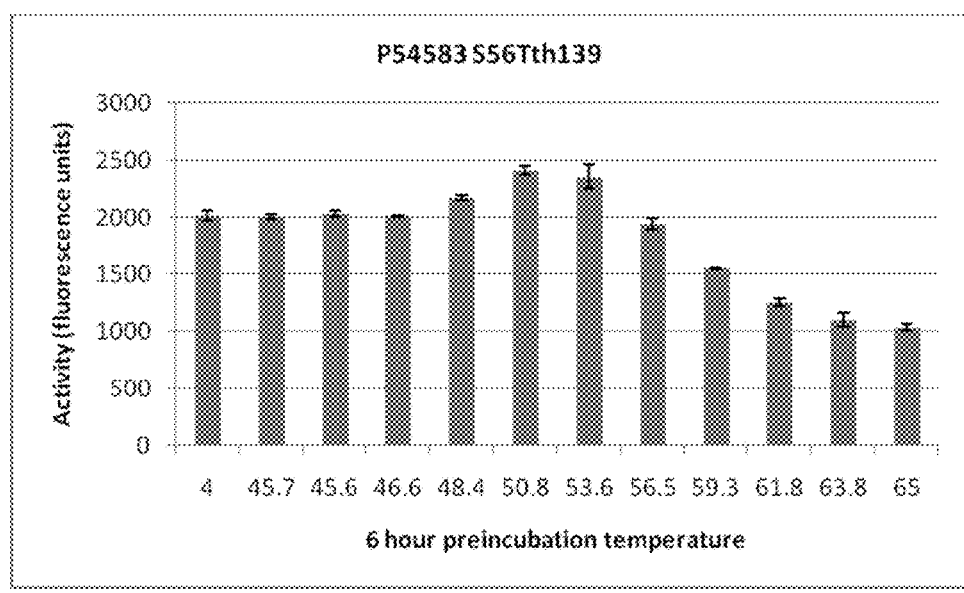
FIG. 20 illustrates enzyme activity recovery by pre-incubation at various temperatures.

To investigate whether the mini-intein in this position showed temperature-sensitive splicing, that is, whether pre-incubation of the recombinant enzyme at particular temperatures reconstituted different amounts of endoglucanase activity, samples from a single culture of SCBJ yeast cells expressing P54583 S56MTth010 were pre-incubated six hours at various temperatures. After this period, the samples were cooled uniformly to 4° C. and then subjected to the standard Enzchek assay (room temperature incubation with substrate). Referring to FIG. 20, preincubation temperatures as high as 46.6° C. reconstituted no more activity than did preincubation at 4° C. However, preincubation of the enzyme for 6 hours at 50.8-53.6° C. led to modest increases in enzyme activity. At higher temperatures, the endoglucanase activity appeared to drop below the levels attained by enzymes that had not been heated above 4° C. At least in part this decrease in apparent activity may be due to the loss of a background "endoglucanase-like" activity that can be detected in yeast culture supernatants. The background activity is heat labile at such elevated temperatures. When total endoglucanase activity is slow (as in this particular experiment), the effect of this background activity can be significant. To some extent, the effect of this phenomenon can be seen in the data depicted in FIG. 19 where the endoglucanase "activity" of the negative control s ample (pAL410) appears to decrease when the culture is preincubated at 55° C. prior to the assay. FIG. 20 shows that a temperature between 50.8° C. and 53.6° C. leads to the reconstitution of the greatest amount of activity from this recombinant enzyme.

Figure 21:
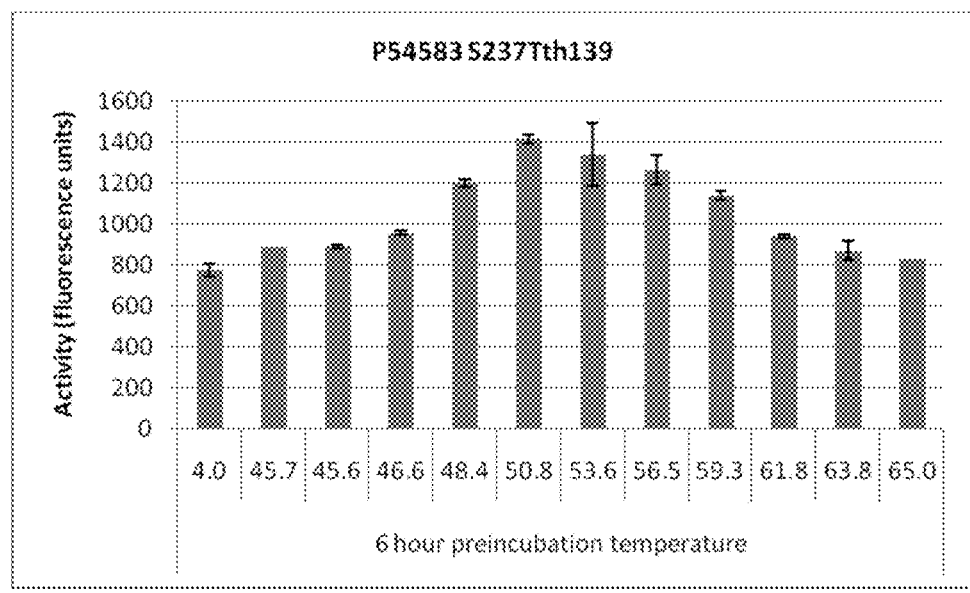
FIG. 21 illustrates enzyme activity recovered from P54583 carrying a mini-intein in the S237 position after pre-incubation at different temperatures.

Eight mini-inteins were introduced into the 5237 position of P54583. The eight mini-inteins had the sequence of SEQ ID NOS: 2009-2016, respectively. One intein was inserted per construct. The mini-inteins were introduced into the S237 position via in vivo recombination. Candidate recombinant yeast colonies were recovered in each case, and the plasmids that each carried were isolated and tested via DNA sequencing to confirm whether the gene responsible for the intein-modified endoglucanase was intact, and lacking point mutations or other changes. Once a yeast strain had been identified for each of the mini-intein-modified endoglucanases, the entire set was subjected to endoglucanase assays. Strains carrying the mTth010 mini-intein demonstrated clear endoglucanase activity. As shown in FIG. 21, this intein-modified endoglucanase also showed an optimum induction temperature near 52.5° C. Preincubation of the enzyme for 6 hours at 50.8-53.6° C. led to an increase in enzyme activity of approximately 75%. Assays were carried out at room temperature for 1 hour using the Enzchek substrate. Additional P54583-mTth010-5237 intein modified proteins that were isolated and showed improved activity levels are given as SEQ ID NOS: 1751, 1752.

Figure 22:
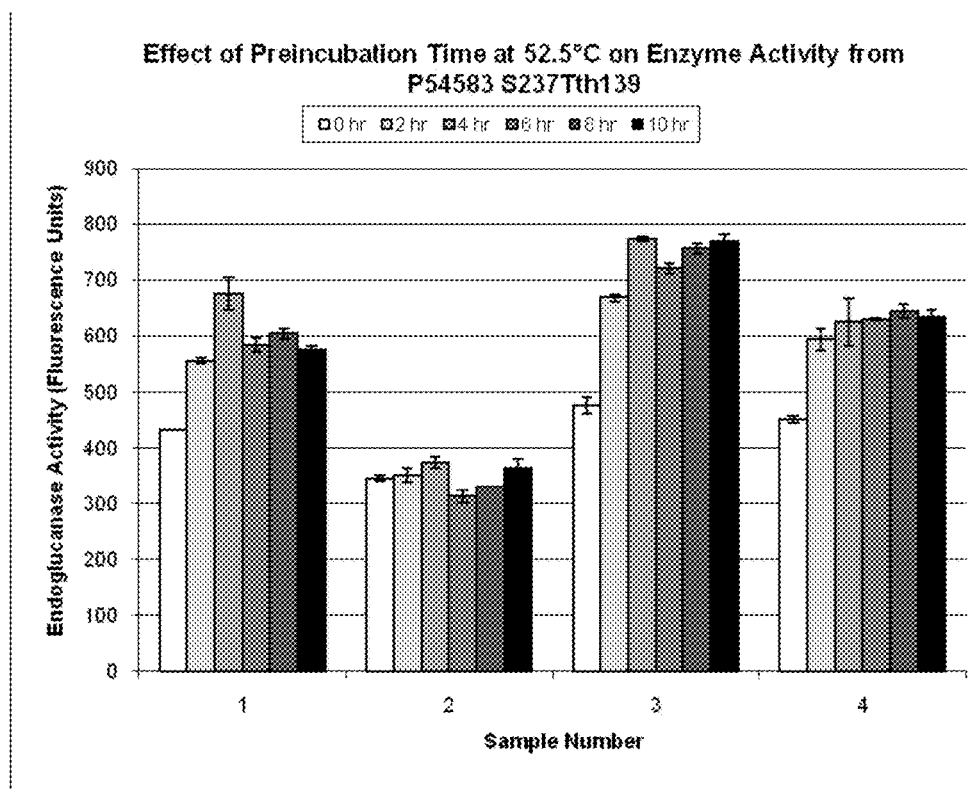
FIG. 22 illustrates pre-incubation time and intein-modified endoglucanase activation.

Having shown thmTth010at activity could be recovered from the P54583 S237MTth010 intein-modified endoglucanase by pre-incubation at approximately 52.5° C., it was then tested whether the length of this pre-incubation step influenced enzyme activity. Four separate colonies from a culture of SCBJ (pAL410 P54583noHis S237Tth139) were cultured independently in a rich medium. Aliqouts were sampled from each culture, split into multiple samples, and each split sample pre-incubated for different lengths of time at 52.5° C. as follows: 0 hours (not heated, pre-incubated only at 4° C.), 2 hours, 4 hours, 6 hours, 8 hours, or 10 hours. Following the pre-incubation step, individual split samples were stored at 4° C. until assays were carried out. Each split sample was then assayed via the Enzchek assay at room temperature. As shown in FIG. 22, three of the four cultures tested achieved their highest level of activation within 2-4 hours. Longer pre-incubation times either did not improve enzyme activation or caused a decrease in the amount of activity recovered.

Example 11—Mutagenesis and Screening of Intein-Modified Endoglucanases

Using the strategies outlined in reference to FIGS. 18A-18C, error-prone PCR was used to create collections (libraries) of mutants carrying base pair alterations in the DNA encoding the inteins and adjacent portions of the endoglucanase. Libraries were prepared that are derivatives of both full-length and mini-inteins in each of several positions in P54583, including the S56, C75, S192, and S237 positions. Yeast clones from each library were collected for preliminary analysis. Colony PCR (Using KAPA2G Robust Taq from KAPA Biosystems, Waltham Mass.) was used to amplify the portion of the endoglucanase-encoding gene that included the mutagenized intein in each case. These PCR products were then subjected to DNA sequencing to assess the frequency and nature of the mutations in the library.

Figure 23:
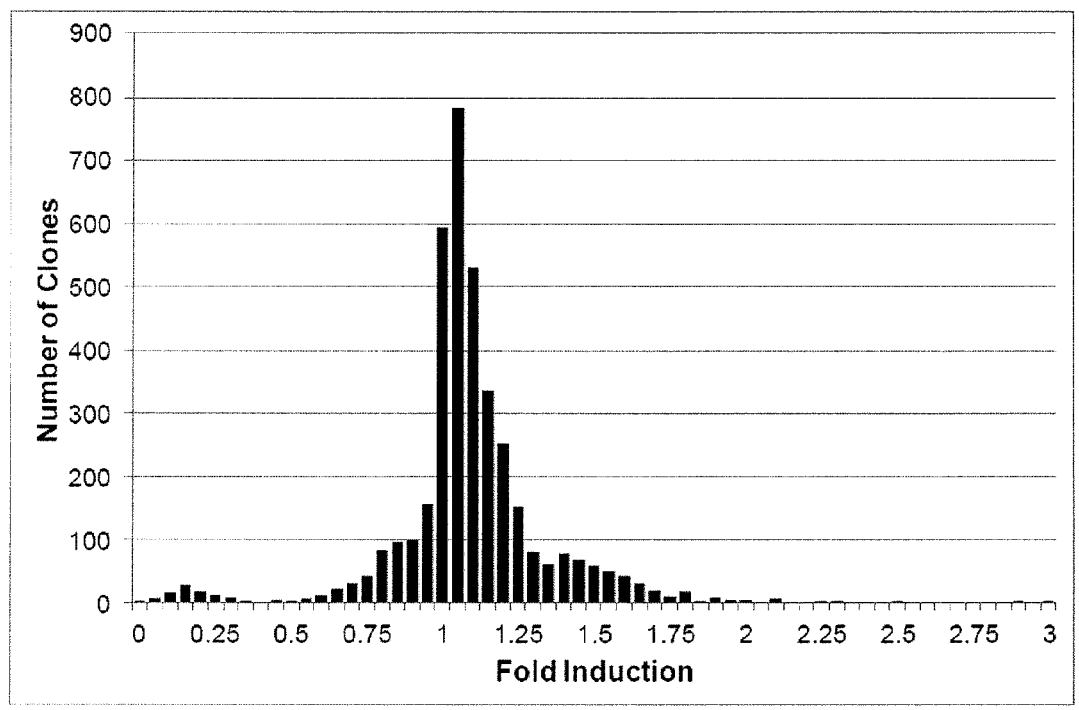
FIG. 23 illustrates high throughput endoglucanase assay results for an intein modified endoglucanase library.

Following the initial assessment of mutation frequencies, clones from an individual library were spread onto selective media (YPD agar supplemented with 100 mg/L G418) and grown at 30° C. for 2-3 days. 3760 colonies were picked from these plates, along with a number of positive [SCBJ (pAL410 P54583noHis)] and negative [(SCBJ(pAL410)] controls, and inoculated into 1 ml volumes of YPD liquid medium supplemented with 100 mg/L G418 that had been dispensed into deep, 96-well plates. These cultures were then incubated for 3 days with vigorous shaking at 30° C. Aliquots were then removed from each of the liquid cultures, divided into replicate samples, and subjected to the Enzchek assay. For each culture, a portion of the replicate samples were pre-incubated at 52.5° C. for 4 hours, while the remainder were incubated at room temperature. Afterward, all replicate samples were equilibrated to room temperature, and split into triplicate samples prior to mixing with the Enzchek substrate. After 90 minutes, the endoglucanase reaction was halted by the addition of an equal volume of 20% tris base, and total fluorescence units were measured. The degree of heat-sensitive enzyme activation was inferred from the difference in activity measured from the heated and unheated treatments for each sample. The difference in activity that each clone displayed across the two pretreatment conditions was then calculated as a fold induction where 1-fold denoted no change in activity. Degrees of heat-sensitive increase (or decrease) in enzyme activity were then binned, and the number of clones falling into each category plotted in the histogram of FIG. 23. As shown in FIG. 23, the diversity of behaviors (temperature-sensitivity) among clones from the library is centered on the behavior of the parental clone, in this case the P54583 endoglucanase carrying the MTth010 mini-intein in the S56 position, which also displayed an increase in activity of ~10% (i.e., 1.1-fold induction; cf. FIG. 23) when pre-incubated at about 52.5° C.

Figure 24:
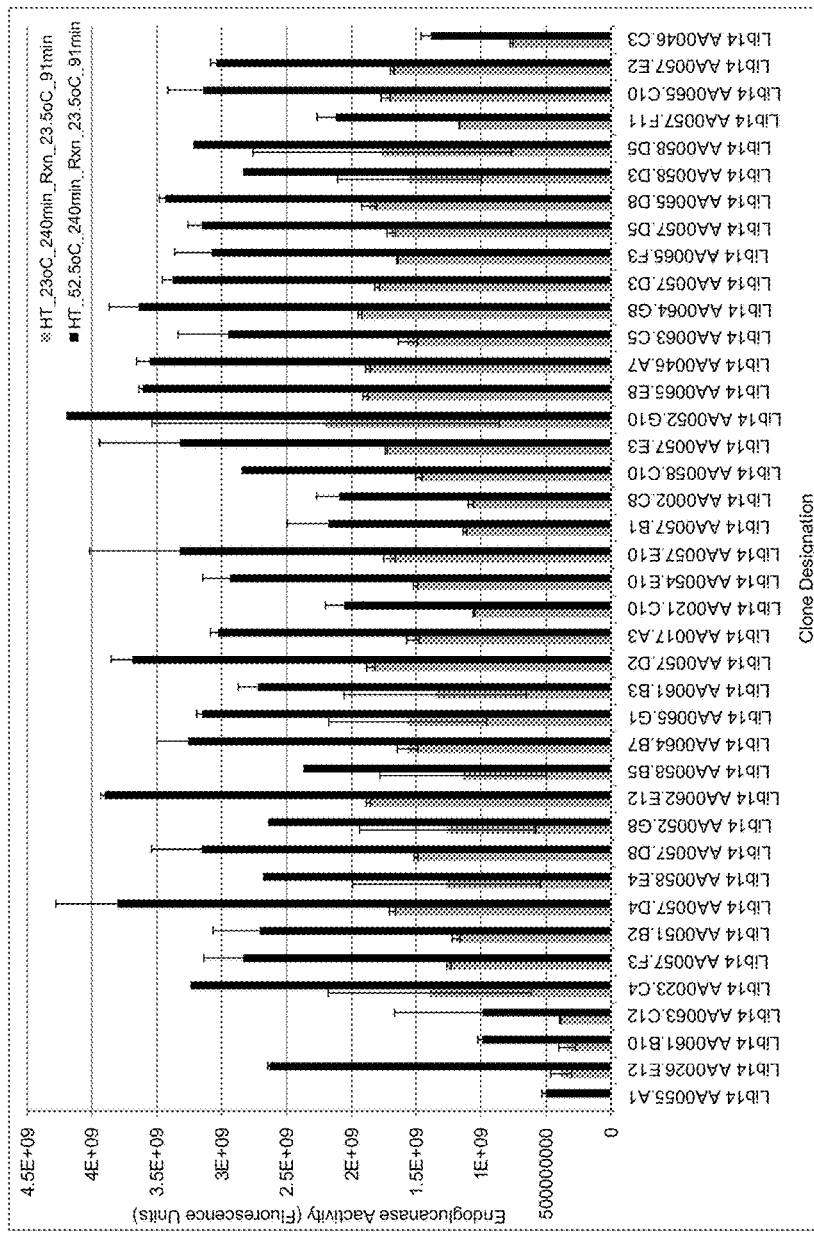
FIG. 24 illustrates of a mutagenized intein modified endoglucanase library screen.

Ranking the degree of temperature-sensitivity among these nearly 4000 clones permitted identification of candidates for further analysis. Clones from a library designated "Library 14" (Lib14, SCBJ cells carrying derivatives of pAL410 P54583 S56Tth139) were analyzed. Clones that showed the greatest difference in activity in the experiment described in reference to FIG. 23 were further analyzed, and a portion of the data is shown in the chart of FIG. 24. Selected clones include the mutant intein modified enzymes indicated in Table 9, below. The activity from room temperature-treated samples is indicated by the left bar for each mutant, and the activity from heat treated samples is indicated by the right bar for each mutant of FIG. 24. Error bars in FIG. 24 reflect the differences in activity among triplicate assays. In these assays, the wild type P54583 positive controls and the pAL410 negative controls typically displayed modest decreases in activity following pre-incubation at the elevated temperature. As such, none of these control samples appear in FIG. 24 among the 40 clones showing the greatest increase in activity.

TABLE 9

| MUTANT | SEQUENCE |
|---|---|
| AA0002.C8 | SEQ ID NO: 1745 |
| AA0021.C10 | SEQ ID NO: 1746 |
| AA0057.F3 | SEQ ID NO: 1747 |
| AA0057.D5 | SEQ ID NO: 1748 |
| AA0063.C5 | SEQ ID NO: 1749 |
| AA0064.B7 | SEQ ID NO: 1750 |

Figure 25:
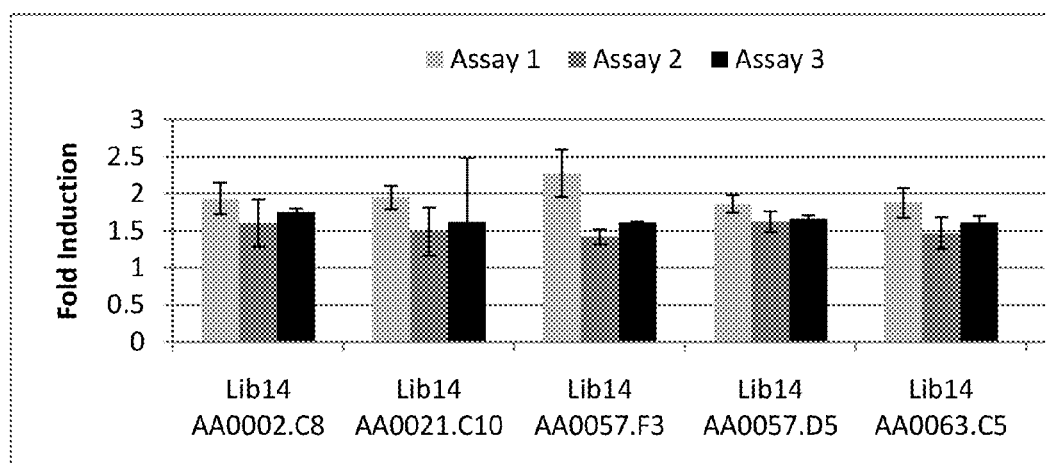
FIG. 25 illustrates repeated activity assays on candidates from a mutagenized intein modified endoglucanase library.

Individual clones were collected from the above set and colony purified. Fresh cultures (in YPD G418) were grown from 3 single colonies derived from each clone, and these cultures were subjected to the Enzchek assay for temperature-sensitivity endoglucanase activity, constituting a second assay of the above candidates. Subsequently, a colony from one of the 3 single colonies that had been used for the second assay was used to inoculate 3 separate 1 ml volumes of YPD G418, grown at 30° C., and tested via the Enzchek assay, constituting a third assay of the above candidates. In each case, the fold increase in activity was calculated, making it possible to determine the reproducibility of the performance of each clone. Such a comparison is shown in FIG. 25 for six of the clones collected from this library. In FIG. 25, Assay 1 refers to the initial result with each clone from the high-throughput screening. The data from this assay correspond to a single culture from which 6 technical replicates (3 pre-heated, 3 unheated) were generated and assayed. Data from Assay 2 reflects 3 biological samples (single cultures derived from 3 separate colonies), from which duplicate samples were prepared (one pre-heated, one unheated), which were each then split into two technical replicates prior to the assay. Assay 3 reflects results with cultures derived from single colonies purified from the initial cultures that had been examined during Assay 1. In Assay 3, the results are averages of a minimum of 12 assays (6 pre-incubated at room temperature and 6 pre-incubated at 52.5° C.), with each set of 6 corresponding to two technical replicates for each of a minimum of three biological replicates. These results suggest that the initial screen may slightly overstate the degree of change in activity that can be recovered from a given clone, although each of the candidates shown in FIG. 25 showed ≥1.5-fold induction in subsequent assays.

Portions of the DNA sequences encoding the intein-modified endoglucanases were isolated by colony PCR from several of the candidates identified in the original screening of Library 14. An examination of the sequences of the intein-coding regions from each clone presented in FIG. 25 showed that each carried a mutation that caused at least one amino acid change within the sequence of mini intein MTth010, and one of the clones also had a mutation that resulted in an amino acid change in the adjacent N-extein sequence. These mutations are listed in Table 10, below.

TABLE 10

| Original Clone Designation | Amino Acid Changes in MTth010* | Amino Acid Changes in P54583† |
|---|---|---|
| Lib14 AA0002.C8 | L66S | |
| Lib14 AA0021.C10 | P104L | |
| Lib14 AA0057.F3 | R55C | |
| Lib14 AA0057.D5 | R55C | |
| Lib14 AA0063.C5 | E27K | P21S |
| Lib14 AA0064.B7 | L86V | |

*Numbering relative to that of MTth010
†Numbering relative to the mature form of P54583 endoglucanase In the examples summarized in Table 10, only the regions in the immediate vicinity of the intein were sequenced. It is interesting to note, however, that two independent clones were recovered with the same mutation in the intein (R55C in both Lib14 AA0057.F3 and Lib14 AA0057.D5).

Figure 26:
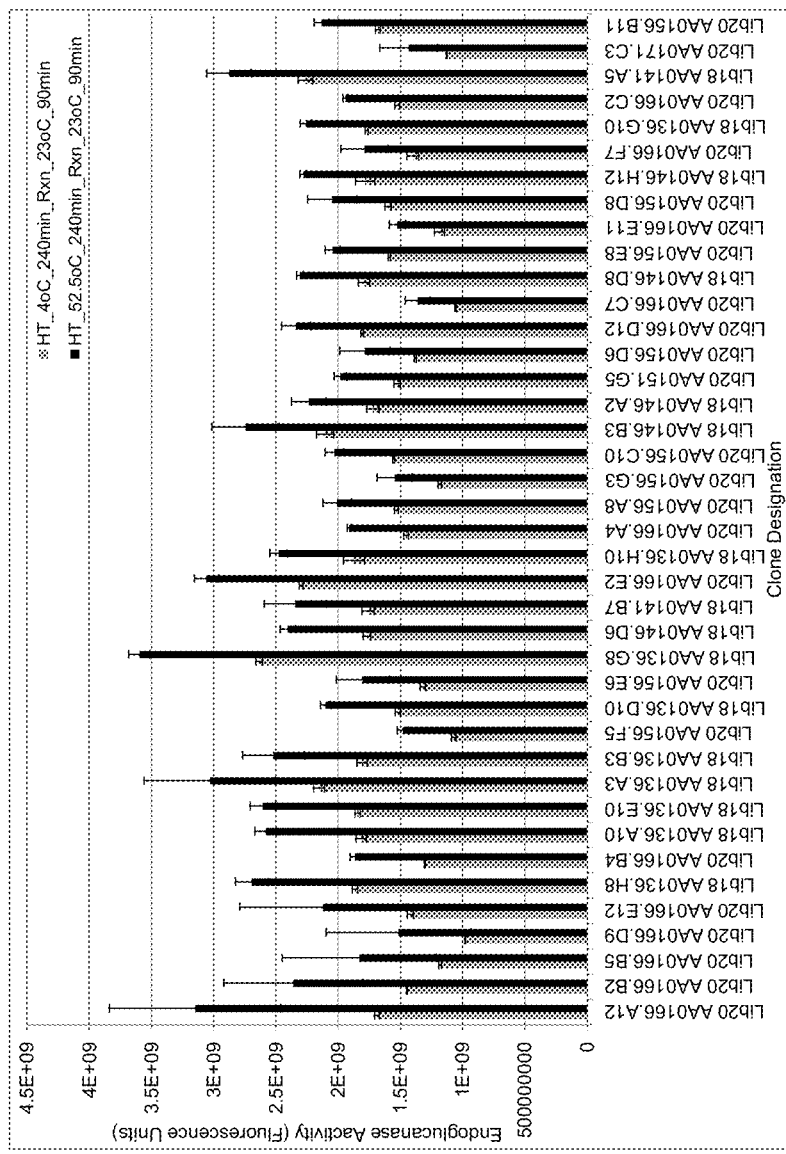
FIG. 26 illustrates heat-inducible enzyme activity from intein modified endoglucanases carrying mutations in the R51 position of the Tth intein.

Additional libraries were constructed in which a single amino acid within the full-length Tth intein was targeted for saturating mutagenesis. Previous results with intein mutagenesis in a xylanase (SwissProt accession number P77853) revealed that mutations that affected arginine 51 of the intein when Tth was inserted into certain positions of P77853 gave the intein-modified xylanase a strong temperature-sensitivity switching phenotype. To test whether a similar mutation might cause a temperature-sensitive behavior in intein-modified endoglucanases, we introduced random mutations at the R51 position of the Tth intein, where the inteins were carried in either the S56, C75, S192, or S237 positions of P54583. Libraries of yeast clones expressing intein-modified endoglucanases with these mutations were then screened with the same high-throughput Enzchek assay described above. Data were sorted to identify those clones that expressed enzymes with the strongest temperature-sensitive induction. As shown in FIG. 26, candidates arising from this screen showed modest (1.5 to 2-fold) induction in activity upon pretreatment. The majority of the best performers were derived from those clones that carried the inteins in either the S192 or the S56 positions of P54583.

Example 12—Termite Endoglucanases

An endoglucanase from *Nasutitermes takasagoensis* was modified with an intein such that the intein compromises the activity of the endoglucanase, and excision of the intein (either spontaneously or in response to a stimulus such as temperature shift) reconstitutes activity of the endoglucanase. The intein-modified endoglucanase may be used in applications that require the conditional hydrolysis of cellulosic materials and/or other polysaccharides that can be recognized as substrates by the endoglucanase. The termite-derived endoglucanase may have advantageous pH tolerance, expression, and/or higher specific activity relative to other endoglucanases. For example, a pH inducible intein could be inserted in endoglucanase.

Termites naturally metabolize a variety of lignocellulosic materials by virtue of their unique anatomy, physiology, and symbiotic microflora. As termites consume lignocellulosic materials, they mix the particulate matter with a variety of enzymes. Passing through the termite gut, the materials encounter pH changes that range from mildly acidic to strongly basic. Particles are then taken up by symbionts that populate the termite gut and are further metabolized. Exchanges of organic metabolites between the symbionts and the termite provide a means by which the termites derive indirect nutritional benefit from the ingested materials.

Not all of the digestive enzymes responsible for the breakdown of lignocellulosic materials in termites are microbial in origin. Some of the most active enzymes in the termite system are actually expressed and secreted by the termites themselves and subsequently taken up by the symbionts along with the particulate materials. In some termite species, such as *Reticulitermes speratus* or *Mastotermes darwiniensis*, endoglucanases are secreted from the salivary glands and are mixed with the woody material during mastication, after which they pass into the gut and are then taken up by the symbionts. In other species, such as *Nasutitermes takasagoensis*, the enzymes are secreted directly in the midgut.

Figure 27:
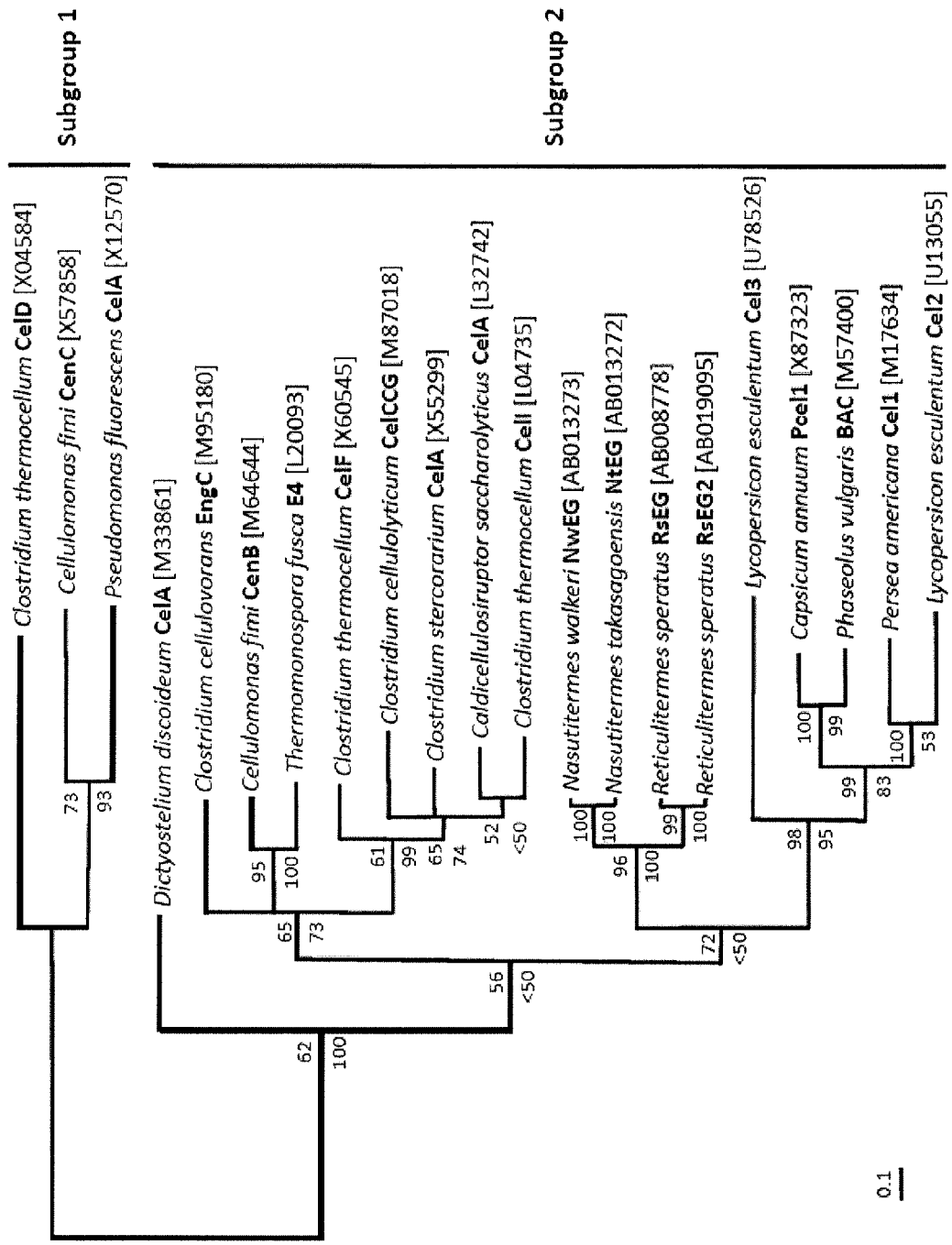
FIG. 27 illustrates a phylogenetic tree of endoglucanases.

FIG. 27 shows the phylogeny of termite endoglucanases. Amino acid sequence comparisons of the catalytic domains from a variety of glycosyl hydrolase (GH9) endoglucanases reveals considerable similarity among termite (*Nasutitermes, Reticulitermes*), microbial, and plant-derived enzymes. As shown, endoglucanases (EC 3.1.2.4) expressed by primitive and more apical termites share significant homology not only with each other, but also with bacterial and plant-derived enzyme. Unlike many members of the GH9 family of enzymes, termite endoglucanases typically lack carbohydrate binding domains, consisting solely of the catalytic domains. NtEG, an endoglucanase from *Nasutitermes takasagoensis*, can be expressed in *E. coli* as a functional enzyme. Differential cellulolytic activity of the native-form and C-terminal tagged-form of a cellulase derived from *Coptotermes formosanus* and expressed in *E. coli* has enabled the in vitro evolution of enzyme derivatives with enhanced properties such as thermostability. Random exchanges of non-conserved amino acid residues among four parental termite cellulases by family shuffling has also improved thermostability. Any of these cellulases can be modified with an intein, as outlined herein.

The NtEG endoglucanase has been shown to be structurally stable under very acidic conditions. This may reflect the fact that, as mentioned previously, termite-derived endoglucanases are exposed to a wide pH range in the gut. The major endoglucanase from *Nasutitermes takasagoensis* (NtEG) has been crystallized and it undergoes only very subtle changes in structure across pH ranges from 6.5 to 2.5. Termite-derived intein modified endoglucanases may be provided in conditions involving exposure to strong pH changes.

Example 13—Expression and Characterization of Termite Endoglucanases

A codon-optimized version of NtEG (O77044, SEQ ID NO: 2017) was prepared. The DNA sequence of NtEG as optimized for expression in plants is shown below. Included in this sequence is a region (underlined in the sequence below) that encodes an N-terminal polypeptide of about 16 amino acids that likely functions as a secretion signal when the protein is expressed in termite cells.

```
Codon optimized NtEG
                                    (SEQ ID NO: 2017)
ATGAGGGTGTTCCTTTGCCTGCTCTCGGCGCTAGCTTTGTGCCAGGCGGC

TTACGACTACAAGCAGGTGTTGCGGGACTCGCTACTATTCTATGAGGCCC

AGAGATCCGGCCGGCTCCCAGCCGACCAGAAGGTCACGTGGAGGAAGGAT

AGCGCGCTGAATGACCAGGGTGACCAGGGACAAGACTTGACCGGCGGCTA
```

-continued
```
CTTTGACGCTGGGGACTTCGTCAAGTTCGGGTTCCCCATGGCTTATACCG

CAACCGTGCTGGCATGGGGCCTCATAGATTTTGAGGCCGGCTACAGCAGT

GCCGGGGCCTTGGATGATGGACGGAAGGCTGTCAAATGGGCCACCGACTA

TTTCATAAAGGCCCACACAAGTCAAAATGAGTTCTATGGTCAGGTCGGCC

AGGGTGACGCCGATCACGCTTTCTGGGGAAGACCAGAGGATATGACGATG

GCGCGCCCGGCGTACAAGATAGACACCTCAAGGCCTGGCTCTGATCTGGC

AGGCGAGACAGCGGCTGCTCTTGCCGCTGCTTCAATCGTGTTCCGGAACG

TCGATGGCACTTACTCAAATAACCTGTTAACACACGCTCGCCAGCTATTC

GACTTCGCGAACAACTACCGGGGAAAGTATAGTGACTCTATTACTGACGC

AAGAAATTTCTACGCAAGCGCAGACTACAGAGACGAGTTGGTTTGGGCTG

CTGCGTGGTTATACAGAGCGACCAACGACAACACCTACCTCAACACTGCT

GAGTCACTGTACGATGAGTTTGGGCTACAGAACTGGGGGGGGGGCCTGAA

CTGGGATAGCAAGGTGTCTGGCGTGCAGGTGTTGTTGGCCAAGCTTACCA

ATAAGCAGGCCTACAAGGACACGGTGCAGTCTTACGTCAATTACCTAATT

AATAACCAGCAGAAGACTCCCAAGGGCCTCCTCTACATCGACATGTGGGG

CACCCTTCGCCACGCTGCCAACGCCGCATTCATCATGCTCGAAGCCGCCG

AGCTGGGCTTGTCCGCCTCCTCTTATAGACAGTTCGCGCAAACGCAAATC

GACTACGCCCTGGGCGATGGTGGCCGCTCCTTTGTGTGCGGGTTCGGGAG

TAATCCTCCTACGAGACCGCACCACAGATCCTCGTCGTGCCCGCCAGCTC

CCGCTACTTGCGACTGGAATACATTCAACTCACCTGACCCAAACTACCAC

GTCCTCTCTGGGGCCCTAGTGGGCGGACCTGATCAGAATGACAACTACGT

CGATGACCGTTCAGACTATGTTCACAACGAAGTCGCCACTGATTACAACG

CGGGTTTCCAGTCCGCGTTAGCTGCTTTGGTGGCCCTTGGTTAC
```

Figure 28:
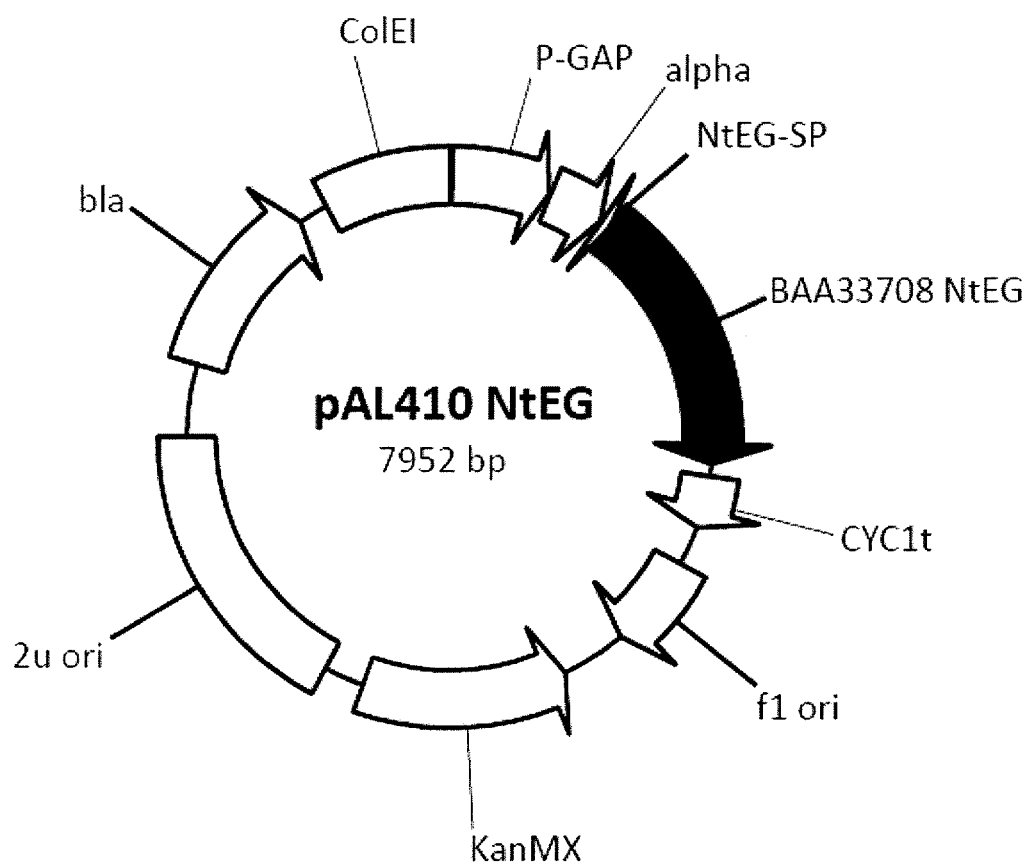
FIG. 28 illustrates a plasmid vector for expression and secreting intein modified proteins; e.g., expression an sectreting of an endoglucanase derived from termite in yeast.

A DNA fragment carrying this sequence was ligated into the *Saccharomyces cerevisiae* expression vector pAL410. The resulting construct, pAL410 NtET is illustrated in FIG. 28. In FIG. 28, P-GAP is the nominally constitutive yeast GAP promoter; alpha is the secretion signal from yeast alpha mating factor, which is translated as an N-terminal fusion to the termite-derived endoglucanase; NtEG-SP is the putative 16 amino acid signal sequence that may drive secretion of NtEG from termite cells; BAA33708 NtEG is the remainder of the coding sequence for the termite endoglucanase; CYCt is a transcriptional terminator and polyadenylation signal derived from the yeast CYC1 gene; f1 ori is the sequence for generating single-stranded plasmid derivatives; KanMX is a gene conferring resistance to G418 in yeast; 2u ori is the 2 micron origin, enabling plasmid replication in yeast cells; bla is a gene conferring ampicillin resistance in bacterial cells; and ColEI is a region that enables replication of the plasmid in *E. coli*.

It is possible that the two signal peptides, one derived from yeast and the second native to NtEG, might conflict during expression from the pAL410. To determine whether expression of NtEG might be enhanced by removing the native signal peptide, a derivative of the NtEG expression vector was prepared that differed from the original vector only in that it that lacked the 48 base pairs from the beginning of the NtEG open reading frame. These 48 base pairs encode native signal peptide. This vector (pAL410 NtEGm) was introduced into yeast cells.

Figure 29:
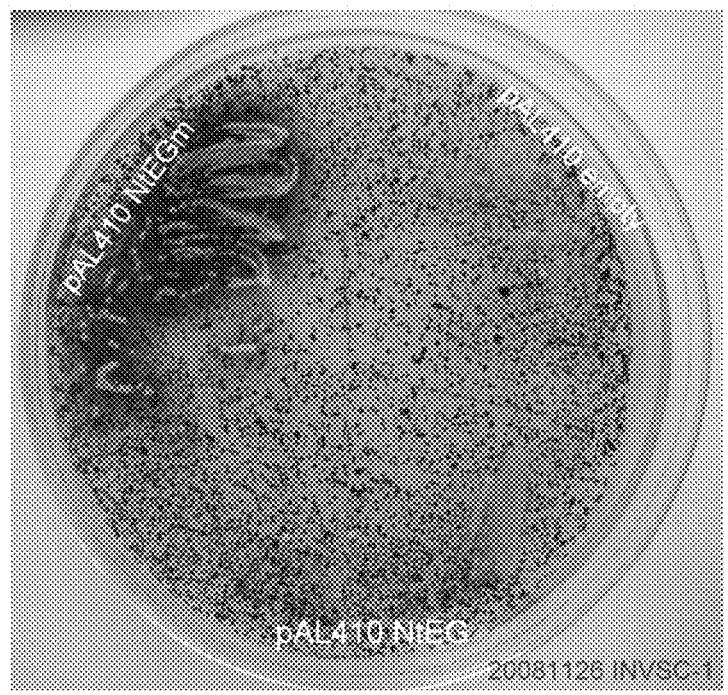
FIG. 29 illustrates yeast expressing an empty expression vector, an expression vector encoding NtEG, and an expression vector encoding a mutant NtEG lacking the native signal peptide.

Yeast cells carrying one of pAL410, pAL410 NtEG, or pAL410 NtEGm were streaked onto plates of YPD agar containing 100 mg/L G418 onto which an overlay of 1.5% agarose and 0.2% AZCL-HE-cellulose (Megazyme International Ireland Ltd) had been applied. As shown in FIG. 29, endoglucanase activity could be detected most readily in the vicinity of colonies that carried pAL410 NtEGm, indicating both that the enzyme was active and that it was being secreted from growing cells.

Figure 30:
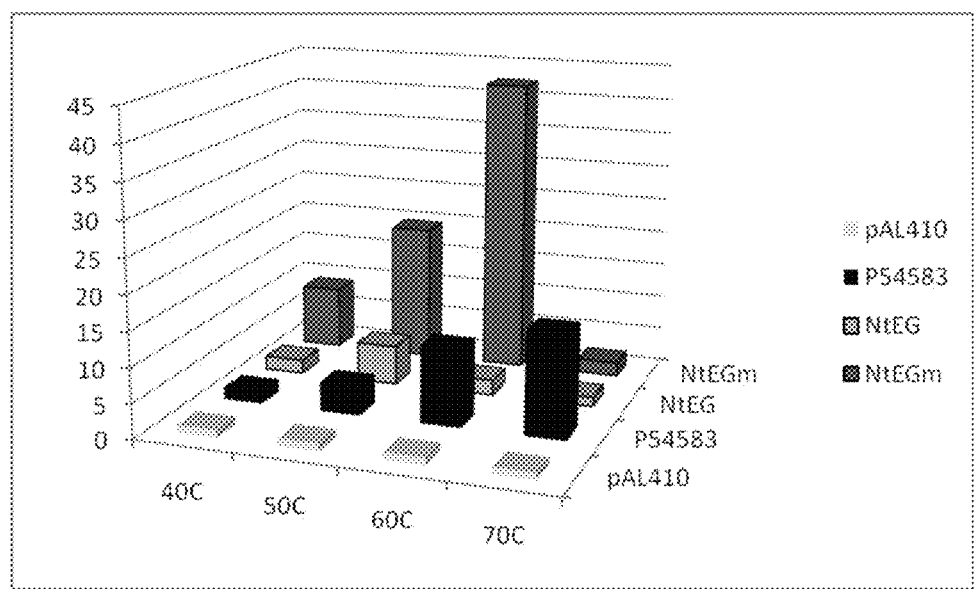
FIG. 30 illustrates endoglucanase activity of NtEG and a mutant NtEG lacking the native signal peptide over a range of temperatures.

Yeast cells carrying pAL410 NtEG, pAL410 NtEGm, or pAL410-P54583 (Ace 1 endoglucanase, see Example 7) the above plasmids, as well as a strain that carried the empty pAL410 vector as a control, were then grown in rich media, and the culture supernatants were assayed for endoglucanase activity via the Cellazyme C assay (Megazyme International Ireland Ltd), which measures release of dye (absorbance at 590 nm) from AZCL-HE-cellulose. As shown in FIG. 30, the mature form of the termite endoglucanase (NtEGm) clearly gives higher activity than does the full-length form, which retains the native signal sequence. NtEGm also shows higher activity than P54583. While both NtEGm and P54583 increase in activity as the temperature increases, NtEGm lost activity when incubated at 70° C., while P54583 activity continued to increase. These assays revealed that expression of NtEGm produced more detectable endoglucanase activity than did P54583.

Figure 31:
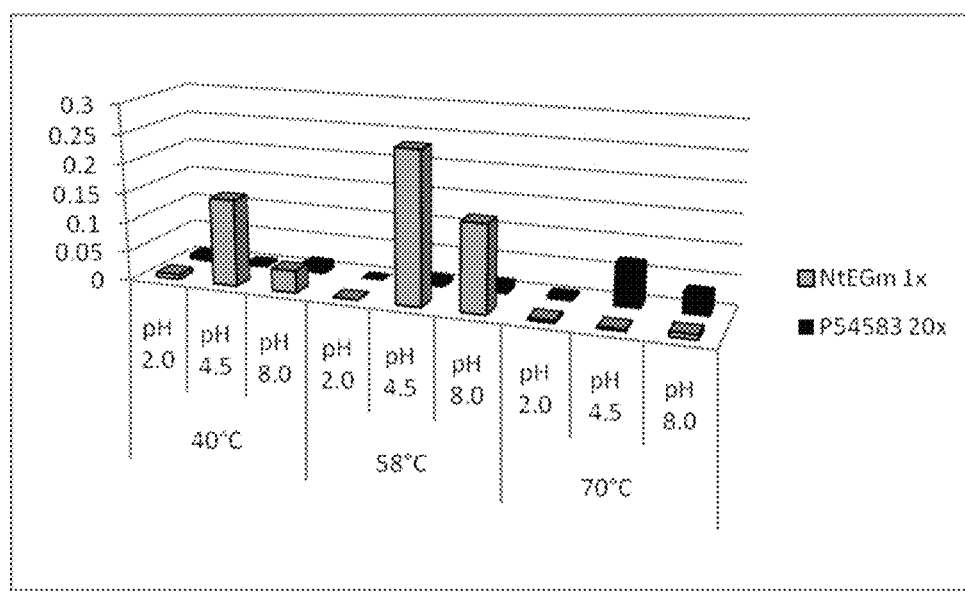
FIG. 31 illustrates endoglucanase activity of a mutant NtEG lacking the native signal peptide and P54583 a over a range of pH.

As a preliminary measure of the pH tolerance of the expressed enzymes, supernatants were collected from cultures expressing either NtEGm or P54583. Because of its lower overall activity, the supernatant from the P54583 culture was concentrated 20-fold via filtration through 10,000 molecular weight cut-off Millicon filters (Millipore, Bedford Mass.) prior to assaying. Cellazyme C assays were then carried out in buffers of different pH and at different temperatures. As shown in FIG. 31, NtEGm showed higher activity at pH 4.5 and 8.0 (as measured by absorbance at 590 nm of the released dye) than did P54583. This trend occurred when the cultures were incubated at 40° C. or at 58° C. As shown previously, though, P54583 activity outperformed that of NtEGm at 70° C. in both of the higher pH conditions.

The pH effects on enzyme stability versus pH effects on enzyme activity (catalysis) were analyzed as follows. P54583 and NtEGm were prepared from culture supernatants as above. The cultures were then exposed to buffers of different pH for 1 hour. After this treatment, buffers were exchanged with assay buffer (pH4.5) via filtration through Ultracel YM-30 regenerated cellulose filters (Millipore). Results from these assays suggest that NtEGm withstands pretreatments at pH values as high as 10.5, but is less hardy at pretreatments at pH 2 or pH 3 (data not shown).

Figure 32:
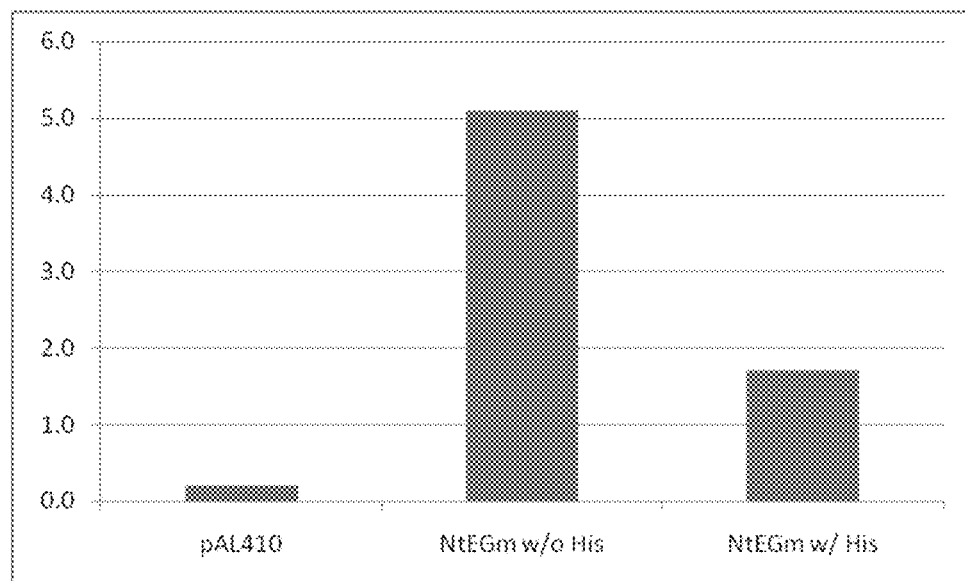
FIG. 32 illustrates endoglucanase activity of a mutant NtEG lacking the native signal peptide and with or without a His tag.

To determine whether a His tag could be added to NtEGm and whether it had any impact on activity, a version of pAL410 NtEGm was created in which 6 histidine codons were introduced immediately before the stop codon of the NtEGm coding sequence. This plasmid, pAL410 NtEGm-His, was introduced into yeast cells. Supernatants were then collected from cultures of yeast cells carrying either pAL410, pAL410NtEGm, or pAL410 NtEGmHis and assayed for endoglucanase activity as before. From these experiments (FIG. 32), it appears that the introduction of a His-tag compromises endoglucanase activity.

Example 14—Intein Modification of Termite Endoglucanases

Figure 33:
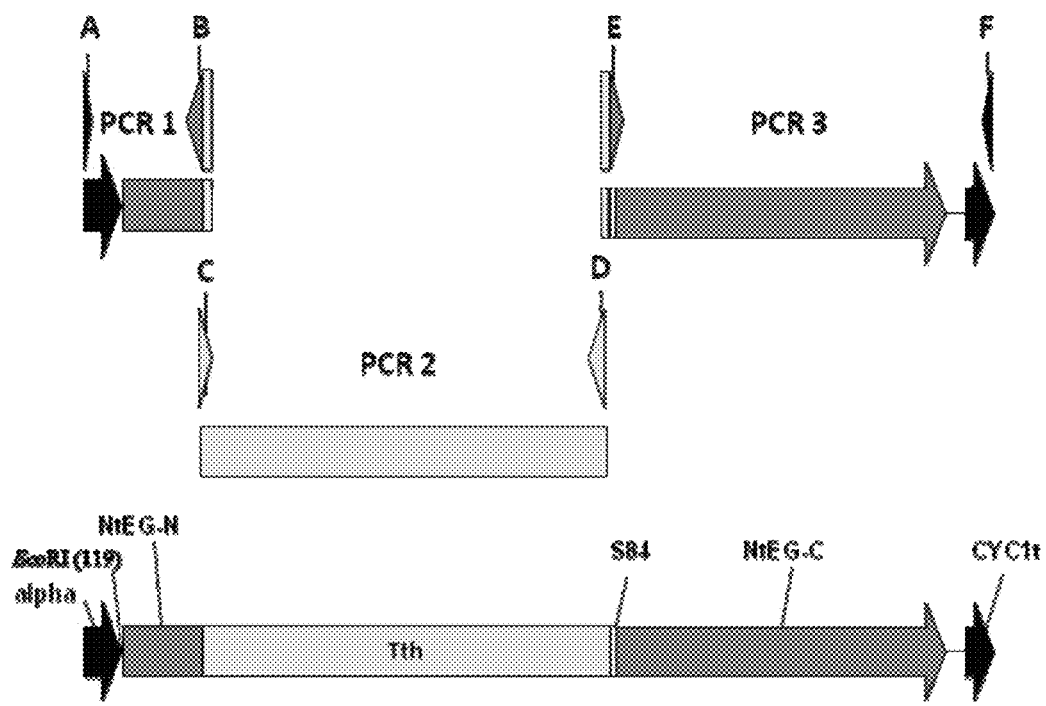
FIG. 33 illustrates a strategy for assembling genes encoding intein-modified NtEG endoglucanases.

A series of protein fusions with the Tth intein inserted into NtEG at different positions were made. The intein insertion site was determined by the method described herein and was typically adjacent to serines, threonines, or cysteines. Coding sequences for the recombinant NtEG proteins were then assembled via an SOE PCR strategy as depicted in FIG. 33 (see also example 6b). As shown in FIG. 33, primers were designed to anneal to:
  (A) the sequence encoding the alpha signal peptide in pAL410 NtEGm;
  (B) a region within the coding sequence for NtEGm that is adjacent to the insertion site (in this case, serine 84);
  (C) the 5' end of the coding sequence for the Tth intein;
  (D) the 3' end of the coding sequence for the Tth intein;
  (E) a region within the coding sequence for NtEGm that is adjacent to the insertion site (in this example, this site does not overlap that covered by primer C); and
  (F) a region within the CYC terminator sequence from pAL410 NtEGm.

PCR1 employs primers A and B to assemble a short product that includes the coding sequences for a portion of the alpha signal factor as well as the N-terminal portion of the endoglucanase (NtEG-N). The extreme 3' end of PCR product 1 includes a short segment that is homologous to the extreme 5' end of the Tth intein. PCR2 employs primers C and D to amplify the coding sequence of the Tth intein. PCR3 employs primers E and F to amplify the coding sequences for the C-terminal portion of the endoglucanase (NtEG-C), including the "C+1" amino acid (in this case serine 84) and a short segment that is homologous to the extreme 5' end of the Tth intein, as well as a portion of the CYC1 terminator (CYC1t) from pAL410. PCR products 1, 2, and 3 were then combined in a single PCR reaction; and by virtue of their homology to the ends of the Tth intein, PCR products 1 and 3 annealed to PCR product 2. DNA synthesis and amplification with the outermost primers (A and F) lead to the assembly of the full-length product as indicated at the bottom of the diagram.

To prepare any desired intein-modified NtEG derivative, PCR products must be prepared that are tailored for each intein insertion position. However, some of the components in this experimental setup are modular. For example, primers C and D can be used to prepare PCR product 2, which can then be used to assemble any of the planned recombinants. Similarly, primers A and F can be used to prepare PCR products 1 and 3, respectively, regardless of the insertion position. As such, only primers B and E are unique to a given intein insertion event. Table 11, below, lists the sequences (in 5'-3' orientation) of the oligonucleotide primers that were used to assemble each of the intein-modified NtEG endoglucanases. While primers B and E are unique to each product, each contains a region that is homologous to the terminus of the Tth intein. This constant region is underlined in each primer sequence in Table 11.

TABLE 11

Primer A   GCTGTTTTGCCATTTTCCAACAGCA (SEQ ID: 2018)

Primer C   TGCCTGGCCGAGGGCTCGCTCGTCTTGGACGCGGCTACCG (SEQ ID: 2019)

Primer D   GTTATGCACCACCAGGTCCTCGCTCACGAAGTTTGCAAAG (SEQ ID: 2020)

Primer F   CCCAAAACCTTCTCAAGCAAGGT (SEQ ID: 2021)

| Insertion Site | Primer B |
|---|---|
| S84 | TCCAAGACGAGCGAGCCCTCGGCCAGGCAGTAGCCGGCCTCAAAATCTATGA (SEQ ID: 2022) |
| T303 | TCCAAGACGAGCGAGCCCTCGGCCAGGCAGCCCCACATGTCGATGTAGAGGA (SEQ ID: 2023) |
| S325 | TCCAAGACGAGCGAGCCCTCGGCCAGGCAGGCGGACAAGCCCAGCT (SEQ ID: 2024) |
| T333 | TCCAAGACGAGCGAGCCCTCGGCCAGGCATTGCGCGAACTGTCTATAAGAGGA (SEQ ID: 2025) |
| S345 | TCCAAGACGAGCGAGCCCTCGGCCAGGCAGCGGCCACCATCGCCCA (SEQ ID: 2026) |
| C348 | TCCAAGACGAGCGAGCCCTCGGCCAGGCACACAAAGGAGCGGCCACCA (SEQ ID: 2027) |
| S352 | TCCAAGACGAGCGAGCCCTCGGCCAGGCACCCGAACCCGCACACA (SEQ ID: 2028) |
| T356 | TCCAAGACGAGCGAGCCCTCGGCCAGGCAAGGAGGATTACTCCCGA (SEQ ID: 2029) |
| S362 | TCCAAGACGAGCGAGCCCTCGGCCAGGCATCTGTGGTGCGGTCTCGT (SEQ ID: 2030) |
| S363 | TCCAAGACGAGCGAGCCCTCGGCCAGGCAGGATCTGTGGTGCGGTCTCGT (SEQ ID: 2031) |
| S364 | TCCAAGACGAGCGAGCCCTCGGCCAGGCACGAGGATCTGTGGTGCGGT (SEQ ID: 2032) |

TABLE 11 -continued

| | |
|---|---|
| T376 | TCCAAGACGAGCGAGCCCTCGGCCAGGCAATTCCAGTCGCAAGTAGCGGGA (SEQ ID: 2033) |
| S379 | TCCAAGACGAGCGAGCCCTCGGCCAGGCAGTTGAATGTATTCCAGTCGCA (SEQ ID: 2034) |
| S406 | TCCAAGACGAGCGAGCCCTCGGCCAGGCAACGGTCATCGACGTAGTTGTCA (SEQ ID: 2035) |
| T415 | TCCAAGACGAGCGAGCCCTCGGCCAGGCAGGCGACTTCGTTGTGAACA (SEQ ID: 2036) |

| Insertion Site | Primer E |
|---|---|
| S84 | AGGACCTGGTGGTGCATAACAGCAGTGCCGGGGCCTTGGA (SEQ ID: 2037) |
| T303 | AGGACCTGGTGGTGCATAACACCCTTCGCCACGCTGCCA (SEQ ID: 2038) |
| S325 | AGGACCTGGTGGTGCATAACTCCTCTTATAGACAGTTCGCGCAAACGCA (SEQ ID: 2039) |
| T333 | AGGACCTGGTGGTGCATAACACGCAAATCGACTACGCCCT (SEQ ID: 2040) |
| S345 | AGGACCTGGTGGTGCATAACTCCTTTGTGTGCGGGTTCGGGA (SEQ ID: 2041) |
| C348 | AGGACCTGGTGGTGCATAACTGCGGGTTCGGGAGTAATCCT (SEQ ID: 2042) |
| S352 | AGGACCTGGTGGTGCATAACAGTAATCCTCCTACGAGACCGCA (SEQ ID: 2043) |
| T356 | AGGACCTGGTGGTGCATAACACGAGACCGCACCACAGATCCT (SEQ ID: 2044) |
| S362 | AGGACCTGGTGGTGCATAACTCCTCGTCGTGCCCGCCA (SEQ ID: 2045) |
| S363 | AGGACCTGGTGGTGCATAACTCGTCGTGCCCGCCAGCT (SEQ ID: 2046) |
| S364 | AGGACCTGGTGGTGCATAACTCGTGCCCGCCAGCTCCCGCT (SEQ ID: 2047) |
| T376 | AGGACCTGGTGGTGCATAACACATTCAACTCACCTGACCCA (SEQ ID: 2048) |
| S379 | AGGACCTGGTGGTGCATAACTCACCTGACCCAAACTACCA (SEQ ID: 2049) |
| S406 | AGGACCTGGTGGTGCATAACTCAGACTATGTTCACAACGA (SEQ ID: 2050) |
| T415 | AGGACCTGGTGGTGCATAACACTGATTACAACGCGGGTTTCCA (SEQ ID: 2051) |

The insertion sites listed in Table 11 refer to the identity and relative position of the amino acid residue in the C+1 position of the extein. The numbering is relative to the amino acid sequence of the predicted NtEGm polypeptide, wherein 2-5 correspond to amino acids 17-20 (Ala-Tyr-Asp-Tyr), of the native, NtEG sequence (O77044) (SEQ ID NO: 112).

Figure 34:
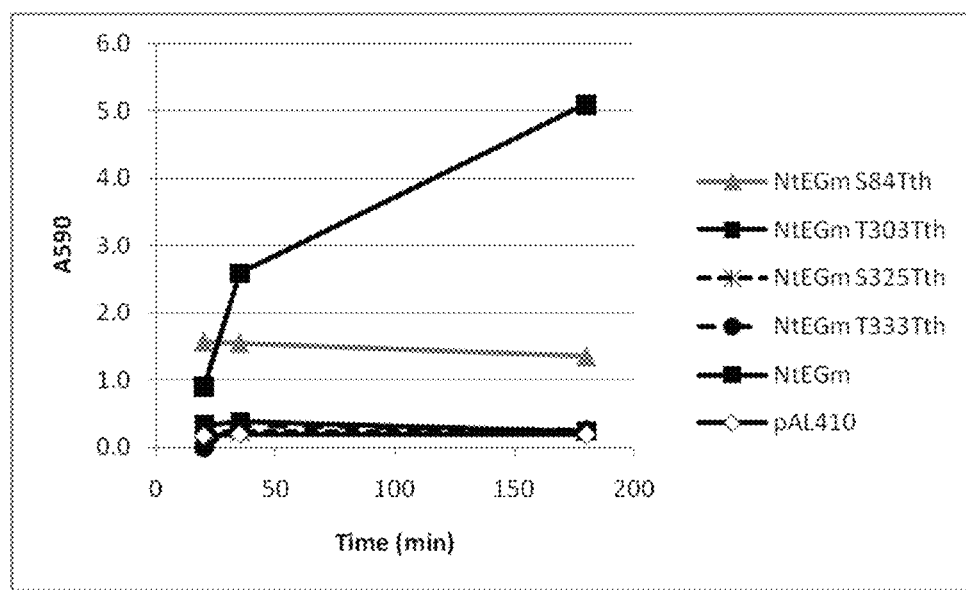
FIG. 34 illustrates a timecourse of enzyme activity from yeast cells expressing intein modified termite endoglucanases.

Using the above primers, SOE PCR reactions were carried out. A subset of these recombinant PCR products has been ligated into pCRBlunt II TOPO (Invitrogen, Carlsbad Calif.), sequenced to confirm composition, and then transferred to the pAL410 yeast expression vector. Supernatants were collected from cultures of yeast cells carrying pAL410, pAL410 NtEGm, or pAL410 NtEGm with the Tth intein inserted adjacent to serine 84, threonine 303, serine 325, or threonine 333. These supernatants were then examined in the Cellazyme C assay, and endoglucanase activity was monitored as an increase in absorbance at 590 nm (due to release of the dye from the AZCL-HE-cellulose substrate) as a function of time. FIG. 34 shows that insertion of the Tth intein into any of the four positions tested strongly reduces activity of the enzyme.

It is understood, therefore, that this invention is not limited to the particular embodiments disclosed, but is intended to cover all modifications which are within the spirit and scope of the invention as defined by the appended claims; the above description; and/or shown in the attached drawings.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10196623B2). An electronic copy of the "Sequence Listing" will also be available from the USPTO upon request and payment of the fee set forth in 37 CFR 1.19(b)(3).

What is claimed is:

1. An intein modified protein comprising a target protein and an intein inserted into the target protein at a site i) immediately prior to a cysteine, threonine, or serine residue of the target protein, ii) within ten angstroms from an active site of the target protein, and iii) within 10 amino acids of a loop-β-sheet junction or within 10 amino acids of a loop-α-helix junction of the target protein, wherein the target protein is a xylanase or a cellulase, and the intein has a sequence with at least 90% identity to a sequence selected from the group consisting of SEQ ID NOS: 3, 88, 91-96, 98, 99 and 101.

2. The intein modified protein of claim 1, wherein the site includes an insertion site cassette having amino acid positions −3, −2, −1, 0, 1, and 2 where the 0 position is the cysteine, theronine, or serine and the insertion site cassette has a −3, −2, −1, 0, 1, 2 sequence selected from the group consisting of GGKCGG (SEQ ID NO: 1513), GGKSGG (SEQ ID NO: 1514), GGKTGG (SEQ ID NO: 1515), PGATSP (SEQ ID NO: 1516), PGATVP (SEQ ID NO: 1517), GAKSLG (SEQ ID NO: 1518), PGATSL (SEQ ID NO: 1519), PGASPL (SEQ ID NO: 1520), PGATGP (SEQ ID NO: 1521), AQRSLG (SEQ ID NO:1522), NQPSIV (SEQ ID NO: 1523), NQASIV (SEQ ID NO: 1524), PNMSSA (SEQ ID NO: 1525), GNHSSG (SEQ ID NO: 1526), PSHSAY (SEQ ID NO: 1527), SLMSSC (SEQ ID NO: 1528), TNTSNY (SEQ ID NO: 1529), IDTSRN (SEQ ID NO: 1530), PSTSAY (SEQ ID NO: 1531), QIKSLG (SEQ ID NO: 1532), FETCNY (SEQ ID NO: 1533), AVLSVN (SEQ ID NO: 1534), LVYSAH (SEQ ID NO: 1535), AGYSSA (SEQ ID NO: 1536), MWGTLR (SEQ ID NO: 1537), LSASSY (SEQ ID NO: 1538), FAQTQI (SEQ ID NO: 1539), GGRSFV (SEQ ID NO: 1540), SFVCGF (SEQ ID NO: 1541), GFGSNP (SEQ ID NO: 1542), NPPTRP (SEQ ID NO: 1543), HHRSSS (SEQ ID NO: 1544), HRSSSC (SEQ ID NO: 1545), RSSSCP (SEQ ID NO: 1546), DWNTFN (SEQ ID NO: 1547), TFNSPD (SEQ ID NO: 1548), DDRSDY (SEQ ID NO: 1549), EVATDY (SEQ ID NO: 1550), (SEQ ID NO: NQVTEL 1551), SSVTFW (SEQ ID NO: 1552), LRESVW (SEQ ID NO: 1553), RFHTLV (SEQ ID NO: 1554), DLSSVT (SEQ ID NO: 1555), DNHTWL (SEQ ID NO: 1556), DYNTEV (SEQ ID NO: 1557), LDVSLY (SEQ ID NO: 1558), HYNSIV (SEQ ID NO: 1559), ADLSSV (SEQ ID NO: 1560), NIITEL (SEQ ID NO: 1561), GHQTHI (SEQ ID NO: 1562), MRNSPW (SEQ ID NO: 1563), RFHTLV (SEQ ID NO: 1564), DYNTDD (SEQ ID NO: 1565), DKYSWL (SEQ ID NO: 1566), LDMSIY (SEQ ID NO: 1567), HNQTPT (SEQ ID NO: 1568), DIKSWD (SEQ ID NO: 1569), WGISDK (SEQ ID NO: 1570), SGATDL (SEQ ID NO: 1571), YYYSWW (SEQ ID NO: 1572), SWWSDG (SEQ ID NO: 1573), NFGTYD (SEQ ID NO: 1574), GKTTRV (SEQ ID NO: 1575), NAPSID (SEQ ID NO: 1576), GTQTFD (SEQ ID NO: 1577), QYWSVR (SEQ ID NO: 1578), IVATEG (SEQ ID NO: 1579), GYFSSG (SEQ ID NO: 1580), NGNSYL (SEQ ID NO: 1581), YGWTRN (SEQ ID NO: 1582), YDPSSG (SEQ ID NO: 1583), LGKTTR (SEQ ID NO: 1584), YFSSGY (SEQ ID NO: 1585), IDHTDS (SEQ ID NO: 1586), SWSTNE (SEQ ID NO: 1587), HTDSWS (SEQ ID NO: 1588), NEITIN (SEQ ID NO: 1589), DSWSTN (SEQ ID NO: 1590), LDQSYV (SEQ ID NO: 1591), EDPTIT (SEQ ID NO: 1592), SYVTGY (SEQ ID NO: 1593), PWGSNS (SEQ ID NO: 1594), GSNSFI (SEQ ID NO: 1595), TPGSGG (SEQ ID NO: 1596), TNYSHP (SEQ ID NO: 1597), DGMSYL (SEQ ID NO: 1598), PQKCYI (SEQ ID NO: 1599), DLISLM (SEQ ID NO: 1600), LMSSCM (SEQ ID NO: 1601), AGSSQA (SEQ ID NO: 1602), AGHSAW (SEQ ID NO: 1603), GIATNT (SEQ ID NO: 1604), ATNTSN (SEQ ID NO: 1605), CDPSGR (SEQ ID NO: 1606), PQGTWF (SEQ ID NO: 1607), VIDTSR (SEQ ID NO: 1608), QGLTSL (SEQ ID NO: 1609), SGQSAL (SEQ ID NO: 1610), NGDSYW (SEQ ID NO: 1611), SGDTGG (SEQ ID NO: 1612), GVQSYN (SEQ ID NO: 1613), LVYSAH (SEQ ID NO: 1614), EFGTTL (SEQ ID NO: 1615), FQWTFW (SEQ ID NO: 1616), TFWSWN (SEQ ID NO: 1617), NPDSGD (SEQ ID NO: 1618), GYQSSG (SEQ ID NO: 1619), IVESWG (SEQ ID NO: 1620), GWSTNP (SEQ ID NO: 1621), NLGTID (SEQ ID NO: 1622), TGNTTM (SEQ ID NO: 1623), NGNSYL (SEQ ID NO: 1624), YGWSTN (SEQ ID NO: 1625), YQSSGS (SEQ ID NO: 1626), SNASGT (SEQ ID NO: 1627), and DGGTYD (SEQ ID NO: 1628).

3. The intein modified protein of claim 1, wherein the intein modified protein has a switching phenotype and switching is inducible upon exposure to temperatures of 48° C. or higher.

4. The intein modified protein of claim 1, wherein the target protein is a xylanase having a sequence with at least 90% identity with a sequence selected from the group consisting of SEQ ID NOS: 104-108.

5. The intein modified protein of claim 1, wherein intein modified protein includes a sequence having at least 90% identity to one selected from the group consisting of SEQ ID NOS: 1701-1703 and 1711.

6. The intein modified protein of claim 1, wherein the target protein is a cellulase having a sequence with at least 90% identity with a sequence selected from the group consisting of SEQ ID NOS: 109-112.

7. The intein modified protein of claim 1, wherein the intein modified protein has a sequence with at least 90% identity to one selected from the group consisting of SEQ ID NOS: 1719, 1732, 1744, 1751, and 1752.

8. The intein modified protein of claim 1, wherein the intein modified protein has a sequence having at least 90% identity to an amino acid sequence selected from the group consisting of SEQ ID NOS: 1629-1691, 1696, 1697, 1699-1712, 1713-1718, 1720-1731, 1733-1738, 1743, 1744, 1751, 1752, 1767, 1770, 1771, and 1774-1784.

9. An intein modified protein having at least 90% identity to an amino acid sequence selected from the group consisting of SEQ ID NOS: 1692-1695, 1698, 1719, 1732, 1739-1742, 1745-1750, 1753-1766, 1768, 1769, 1772-1773.

10. A transgenic plant including an expression construct encoding an intein modified protein comprising a target protein and an intein inserted into the target protein at a site i) immediately prior to a cysteine, threonine, or serine residue of the target protein, ii) within ten angstroms from an active site of the target protein, and iii) within 10 amino acids of a loop-α-sheet junction or within 10 amino acids of a loop-β-helix junction of the target protein, wherein the target protein is a xylanase or a cellulase, and the intein has a sequence with at least 90% identity to a sequence selected from the group consisting of SEQ ID NOS: 3, 88, 91-96, 98, 99 and 101.

11. The transgenic plant of claim 10, wherein the site includes an insertion site cassette having amino acid positions −3, −2, −1, 0, 1, and 2 where the 0 position is the cystein, theronine, or serine and the insertion site cassette has a −3, −2, −1, 0, 1, 2 sequence selected from the group consisting of GGKCGG (SEQ ID NO: 1513), GGKSGG (SEQ ID NO: 1514), GGKTGG (SEQ ID NO: 1515), PGATSP (SEQ ID NO: 1516), PGATVP (SEQ ID NO: 1517), GAKSLG (SEQ ID NO: 1518), PGATSL (SEQ ID NO: 1519), PGASPL (SEQ ID NO: 1520), PGATGP (SEQ ID NO: 1521), AQRSLG (SEQ ID NO:1522), NQPSIV (SEQ ID NO: 1523), NQASIV (SEQ ID NO: 1524), PNMSSA (SEQ ID NO: 1525), GNHSSG (SEQ ID NO: 1526), PSHSAY (SEQ ID NO: 1527), SLMSSC (SEQ ID NO: 1528), TNTSNY (SEQ ID NO: 1529), IDTSRN (SEQ ID NO: 1530), PSTSAY (SEQ ID NO: 1531), QIKSLG (SEQ ID NO: 1532), FETCNY (SEQ ID NO: 1533), AVLSVN (SEQ ID NO: 1534), LVYSAH (SEQ ID NO: 1535), AGYSSA (SEQ ID NO: 1536), MWGTLR (SEQ ID NO: 1537), LSASSY (SEQ ID NO: 1538), FAQTQI (SEQ ID NO: 1539), GGRSFV (SEQ ID NO: 1540), SFVCGF (SEQ ID NO: 1541), GFGSNP (SEQ ID NO: 1542), NPP-TRP (SEQ ID NO: 1543), HHRSSS (SEQ ID NO: 1544), HRSSSC (SEQ ID NO: 1545), RSSSCP (SEQ ID NO: 1546), DWNTFN (SEQ ID NO: 1547), TFNSPD (SEQ ID NO: 1548), DDRSDY (SEQ ID NO: 1549), EVATDY (SEQ ID NO: 1550), (SEQ ID NO: NQVTEL 1551), SSVTFW (SEQ ID NO: 1552), LRESVW (SEQ ID NO: 1553), RFHTLV (SEQ ID NO: 1554), DLSSVT (SEQ ID NO: 1555), DNHTWL (SEQ ID NO: 1556), DYNTEV (SEQ ID NO: 1557), LDVSLY (SEQ ID NO: 1558), HYNSIV (SEQ ID NO: 1559), ADLSSV (SEQ ID NO: 1560), NIITEL (SEQ ID NO: 1561), GHQTHI (SEQ ID NO: 1562), MRNSPW (SEQ ID NO: 1563), RFHTLV (SEQ ID NO: 1564), DYNTDD (SEQ ID NO: 1565), DKYSWL (SEQ ID NO: 1566), LDMSIY (SEQ ID NO: 1567), HNQTPT (SEQ ID NO: 1568), DIKSWD (SEQ ID NO: 1569), WGISDK (SEQ ID NO: 1570), SGATDL (SEQ ID NO: 1571), YYYSWW (SEQ ID NO: 1572), SWWSDG (SEQ ID NO: 1573), NFGTYD (SEQ ID NO: 1574), GKTTRV (SEQ ID NO: 1575), NAPSID (SEQ ID NO: 1576), GTQTFD (SEQ ID NO: 1577), QYWSVR (SEQ ID NO: 1578), IVATEG (SEQ ID NO: 1579), GYFSSG (SEQ ID NO: 1580), NGNSYL (SEQ ID NO: 1581), YGWTRN (SEQ ID NO: 1582), YDPSSG (SEQ ID NO: 1583), LGKTTR (SEQ ID NO: 1584), YFSSGY (SEQ ID NO: 1585), IDHTDS (SEQ ID NO: 1586), SWSTNE (SEQ ID NO: 1587), HTDSWS (SEQ ID NO: 1588), NEITIN (SEQ ID NO: 1589), DSWSTN (SEQ ID NO: 1590), LDQSYV (SEQ ID NO: 1591), EDP-TIT (SEQ ID NO: 1592), SYVTGY (SEQ ID NO: 1593), PWGSNS (SEQ ID NO: 1594), GSNSFI (SEQ ID NO: 1595), TPGSGG (SEQ ID NO: 1596), TNYSHP (SEQ ID NO: 1597), DGMSYL (SEQ ID NO: 1598), PQKCYI (SEQ ID NO: 1599), DLISLM (SEQ ID NO: 1600), LMSSCM (SEQ ID NO: 1601), AGSSQA (SEQ ID NO: 1602), AGHSAW (SEQ ID NO: 1603), GIATNT (SEQ ID NO: 1604), ATNTSN (SEQ ID NO: 1605), CDPSGR (SEQ ID NO: 1606), PQGTWF (SEQ ID NO: 1607), VIDTSR (SEQ ID NO: 1608), QGLTSL (SEQ ID NO: 1609), SGQSAL (SEQ ID NO: 1610), NGDSYW (SEQ ID NO: 1611), SGDTGG (SEQ ID NO: 1612), GVQSYN (SEQ ID NO: 1613), LVYSAH (SEQ ID NO: 1614), EFGTTL (SEQ ID NO: 1615), FQWTFW (SEQ ID NO: 1616), TFWSWN (SEQ ID NO: 1617), NPDSGD (SEQ ID NO: 1618), GYQSSG (SEQ ID NO: 1619), IVESWG (SEQ ID NO: 1620), GWSTNP (SEQ ID NO: 1621), NLGTID (SEQ ID NO: 1622), TGNTTM (SEQ ID NO: 1623), NGNSYL (SEQ ID NO: 1624), YGWSTN (SEQ ID NO: 1625), YQSSGS (SEQ ID NO: 1626), SNASGT (SEQ ID NO: 1627), and DGGTYD (SEQ ID NO: 1628).

12. The transgenic plant of claim 10, wherein the intein modified protein has a switching phenotype and switching is inducible upon exposure to temperatures of 48° C. or higher.

13. The transgenic plant of claim 10, wherein the target protein is a xylanase having a sequence with at least 90% identity with a sequence selected from the group consisting of SEQ ID NOS: 104-108.

14. The transgenic plant of claim 10, wherein the intein modified protein includes a sequence having at least 90% identity to one selected from the group consisting of SEQ ID NOS: 1701-1703 and 1711.

15. The transgenic plant of claim 10, wherein the target protein is a cellulase having a sequence with at least 90% identity with a sequence selected from the group consisting of SEQ ID NOS: 109-112.

16. The transgenic plant of claim 10, wherein the intein modified protein has a sequence with at least 90% identity to one selected from the group of SEQ ID NOS: 1719, 1732, 1744, 1751, and 1752.

17. The transgenic plant of claim 10, wherein the intein modified protein has a sequence having at least 90% identity to an amino acid sequence selected from the group consisting of SEQ ID NOS: 1629-1691, 1696, 1697, 1699-1712, 1713-1718, 1720-1731, 1733-1738, 1743, 1744, 1751, 1752, 1767, 1770, 1771, and 1774-1784.

* * * * *